US009708630B1

(12) United States Patent
Pfleger et al.

(10) Patent No.: US 9,708,630 B1
(45) Date of Patent: Jul. 18, 2017

(54) CELLS AND METHODS FOR PRODUCING FATTY ALCOHOLS

(71) Applicant: WISCONSIN ALUMNI RESEARCH FOUNDATION, Madison, WI (US)

(72) Inventors: Brian F. Pfleger, Madison, WI (US); J. Tyler Youngquist, Medina, OH (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 178 days.

(21) Appl. No.: 14/509,408

(22) Filed: Oct. 8, 2014

Related U.S. Application Data

(60) Provisional application No. 61/888,199, filed on Oct. 8, 2013.

(51) Int. Cl.
  *C12P 7/04* (2006.01)
  *C12N 1/21* (2006.01)
  *C12N 9/00* (2006.01)
  *C12N 9/02* (2006.01)

(52) U.S. Cl.
  CPC .............. *C12P 7/04* (2013.01); *C12N 9/0008* (2013.01); *C12N 9/93* (2013.01); *C12Y 102/0105* (2013.01); *C12Y 602/01003* (2013.01)

(58) Field of Classification Search
  CPC ........... C12N 9/93; C12N 9/0008; C12P 7/04; C12Y 602/01003; C12Y 102/0105
  See application file for complete search history.

(56) References Cited

U.S. PATENT DOCUMENTS

| | | | |
|---|---|---|---|
| 4,837,148 | A | 6/1989 | Cregg |
| 4,929,555 | A | 5/1990 | Cregg et al. |
| 5,077,214 | A | 12/1991 | Guarino et al. |
| 5,679,543 | A | 10/1997 | Lawlis |
| 5,955,329 | A | 9/1999 | Yuan et al. |
| 7,786,355 | B2 | 8/2010 | Aquin et al. |
| 8,216,815 | B2 | 7/2012 | McDaniel et al. |
| 2011/0165637 | A1 | 7/2011 | Pfleger et al. |

FOREIGN PATENT DOCUMENTS

WO    WO 96/00787    1/1996

OTHER PUBLICATIONS

Sousa et al., Microbiology 148(Pt5):1291-1303, 2002.*
Campbell et al., Molecular Microbiology 47(3):793-805, 2003.*
Abdel-Hamid et al., (2001), Pyruvate oxidase contributes to the aerobic growth efficiency of *Escherichia coli*. *Microbiology* (Reading, England) 147, 1483-98.
Agnew et al., (2012), Engineering *Escherichia coli* for production of C12-C14 polyhydroxyalkanoate from glucose. *Metab. Eng.* 14, 705-13.
Akhtar et al., (2013), Carboxylic acid reductase is a versatile enzyme for the conversion of fatty acids into fuels and chemical commodities. *Proc. Natl. Acad. Sci. U.S.A.* 110, 87-92.
Amann et al., (1988), Tightly regulated tac promoter vectors useful for the expression of unfused and fused proteins in *Escherichia coli*. *Gene*, 69, 301-315.
Arora et al., (2005), Promiscuous fatty acyl CoA ligases produce acyl-CoA and acyl-SNAC precursors for polyketide biosynthesis. *J. Am. Chem. Soc.* 127, 9388-9.
Baba et al., (2006), Construction of *Escherichia coli* K-12 in-frame, single-gene knockout mutants: the Keio collection. *Mol. Syst. Biol.* 2, 2006.0008.
Ballesteros et al., (2001), Bacterial senescence: protein oxidation in non-proliferating cells is dictated by the accuracy of the ribosomes. *The Eur. Mol. Biol. Organ. J.* 20,5280-5289.
Becker et al., (1997), Regulatory O2 tensions for the synthesis of fermentation products in *Escherichia coli* and relation to aerobic respiration. *Arch. Microbiol.* 168, 290-296.
Cheng et al., (2004), Mammalian wax biosynthesis. I. Identification of two fatty acyl-Coenzyme A reductases with different substrate specificities and tissue distributions. *J. Biol. Chem.* 279, 37789-97.
Dellomonaco et al., (2011), Engineered reversal of the β-oxidation cycle for the synthesis of fuels and chemicals. *Nature* 476, 355-9.
Dellomonaco et al., (2010), The path to next generation biofuels: successes and challenges in the era of synthetic biology. *Microb. Cell Fact.* 9, 3.
Dirusso et al., (1992), Characterization of FadR , a Global Transcriptional Regulator of Fatty Acid Metabolism in *Escherichia coli*. *J. Biol. Chem.* 267, 8685-8691.
Doan et al., (2009), Functional expression of five Arabidopsis fatty acyl-CoA reductase genes in *Escherichia coli*. *J. Plant Physiol.* 166, 787-796.
Dueber et al., (2009), Synthetic protein scaffolds provide modular control over metabolic flux. *Nat. Biotechnol.* 27, 753-9.
Frank et al., (2013), Bacterial microcompartments moving into a synthetic biological world. *J. Biotechnol.* 163, 273-9.
Gibson et al., (2009), Enzymatic assembly of DNA molecules up to several hundred kilobases. *Nat. Methods* 6, 343-345.
Hellenbrand et al., (2011), Fatty acyl-CoA reductases of birds. *BMC Biochem.* 12, 64.
Hofvander et al., (2011), A prokaryotic acyl-CoA reductase performing reduction of fatty acyl-CoA to fatty alcohol. *FEBS Lett.* 585, 3538-43.
Kamedas et al., (1981), Purification and Characterization of Acyl Coenzyme A Synthetase from *Escherichia coli*. *J. Biol. Chem.* 256, 5702-5707.
Keasling et al., (2012), Synthetic biology and the development of tools for metabolic engineering. *Metab. Eng.* 14, 189-95.

(Continued)

*Primary Examiner* — Delia Ramirez
(74) *Attorney, Agent, or Firm* — Daniel A. Blasiole; Joseph T. Leone; DeWitt Ross & Stevens, S.C.

(57) ABSTRACT

Recombinant cells and methods for improved yield of fatty alcohols. The recombinant cells harbor a recombinant thioesterase gene, a recombinant acyl-CoA synthetase gene, and a recombinant acyl-CoA reductase gene. In addition, a gene product from one or more of an acyl-CoA dehydrogenase gene, an enoyl-CoA hydratase gene, a 3-hydroxyacyl-CoA dehydrogenase gene, and a 3-ketoacyl-CoA thiolase gene in the recombinant cells is functionally deleted. Culturing the recombinant cells produces fatty alcohols at high yields.

17 Claims, 9 Drawing Sheets

(56) References Cited

OTHER PUBLICATIONS

Kobayashi et al., (2006), Growth phase-dependent expression of drug exporters in *Escherichia coli* and its contribution to drug tolerance. *J. Bacteriol.* 188, 5693-703.

Lennen et al., (2010), A process for microbial hydrocarbon synthesis: Overproduction of fatty acids in *Escherichia coli* and catalytic conversion to alkanes. *Biotechnol. Bioeng.* 106, 193-202.

Lennen et al., (2012), Engineering *Escherichia coli* to synthesize free fatty acids. *Trends Biotechnol.* 30, 659-67.

Lennen et al., (2013), Microbial production of fatty acid-derived fuels and chemicals. *Curr. Opin. Biotechnol.* 1-10.

Liénard et al., (2010), Evolution of multicomponent pheromone signals in small ermine moths involves a single fatty-acyl reductase gene. *Proc. Natl. Acad. Sci. U.S.A.* 107, 10955-60.

Liu et al., (2013), Fatty alcohol production in engineered *E. coli* expressing Marinobacter fatty acyl-CoA reductases, *Appl. Microbiol Biotechnol*, 97:7061-8071.

Matheson, (1996), Surfactants raw materials: classification, synthesis, and uses. In: Spitz, L. (Ed.), Soaps and Detergents: A Theoretical and Practical Review, AOCS, Champaign, IL, pp. 288-303.

Mudge et al., (2008), Fatty Alcohols: Anthropogenic and Natural Occurrence in the Environment. The Royal Society of Chemistry, Cambridge, UK Book Not Provided.

Neidhardt et al., (1974), Culture Medium for Enterobacteria. *J. Bacteriol.* 119, 736-747.

Pfleger, (2013), Metabolic engineering of bacteria for production of specialty chemicals, University of Wisconsin Madison presentation.

Ranganathan et al., (2012), An integrated computational and experimental study for overproducing fatty acids in *Escherichia coli*. *Metab. Eng.* 14, 687-704.

Reiser et al., (1997), Isolation of mutants of Acinetobacter calcoaceticus deficient in wax ester synthesis and complementation of one mutation with a gene encoding a fatty acyl coenzyme a reductase. *J. Bacteriol.* 179, 2969-2975.

Rowland et al., (2012), Plant fatty acyl reductases: enzymes generating fatty alcohols for protective layers with potential for industrial applications. *Plant Science* 193-194, 28-38.

Rupilius et al., (2006), The Changing World of Oleochemicals. *Palm Oil Developments* 44, 15-28.

Sampson et al., (2008), Microcompartments for B12-dependent 1,2-propanediol degradation provide protection from DNA and cellular damage by a reactive metabolic intermediate. *J. Bacteriol.* 190, 2966-71.

Steen et al., (2010), Microbial production of fatty-acid-derived fuels and chemicals from plant biomass. *Nature* 463, 559-562 We Have This One.

Teerawanichpan et al., (2010), Fatty acyl-CoA reductase and wax synthase from Euglena gracilis in the biosynthesis of medium-chain wax esters. *Lipids* 45, 263-273.

Tseng et al., (1996), Effect of Microaerophilic Cell Growth Conditions on Expression of the Aerobic (cyoABCDE and cydAB) and Anaerobic Pathway Genes in *Escherichia coli*. *Microbiology* 178, 1094-1098.

Voelker et al., (1994), Alteration of the specificity and regulation of Alteration of the Specificity and Regulation of Fatty Acid Synthesis of *Escherichia coli* by Expression of a Plant Medium-Chain Acyl-Acyl Carrier Protein Thioesterase. *J. Bacteriol.* 176(23), 7320-7327.

Wang et al., (2012), Development of a new strategy for production of medium-chain-length polyhydroxyalkanoates by recombinant *Escherichia coli* via inexpensive non-fatty acid feedstocks. *Appl. Environ. Microbiol.* 78, 519-27.

Willis et al., (2011) Characterization of a fatty acyl-CoA reductase from Marinobacter aquaeolei VT8: a bacterial enzyme catalyzing the reduction of fatty acyl-CoA to fatty alcohol. *Biochemistry* 50, 10550-8.

Xu et al., (2013), Modular optimization of multi-gene pathways for fatty acids production in *E. coli*. *Nat. Commun.* 4, 1409.

Youngquist et al., (2012), Kinetic modeling of free fatty acid production in *Escherichia coli* based on continuous cultivation of a plasmid free strain. *Biotechnol. Bioeng.* 109, 1518-27.

Youngquist et al., (2013), Free fatty acid production in *Escherichia coli* under phosphate-limited conditions. *Appl. Microbiol. Biotechnol.* 97(11):5149-59.

Youngquist et al., (2013) Production of medium chain length fatty alcohols from glucose in *Escherichia coli*. *Metab Eng.* 20:177-86.

Yu et al., (2000), An efficient recombination system for chromosome engineering in *Escherichia coli*. *Proc. Natl. Acad. Sci. U.S.A.* 97, 5978-5983.

Yuan et al. (1999), Engineering plant thioesterases for altered substrate specificity. U.S. Pat. No. 5,955,329.

Zha et al., (2009), Improving cellular malonyl-CoA level in *Escherichia coli* via metabolic engineering. *Metab. Eng.* 11, 192-198.

Zhang et al., (2012), Enhancing fatty acid production by the expression of the regulatory transcription factor FadR. *Metab. Eng.* 14, 653-60.

Zheng et al., (2012), Optimization of fatty alcohol biosynthesis pathway for selectively enhanced production of C12/14 and C16/18 fatty alcohols in engineered *Escherichia coli*. *Microb. Cell Fact.* 11, 65.

* cited by examiner

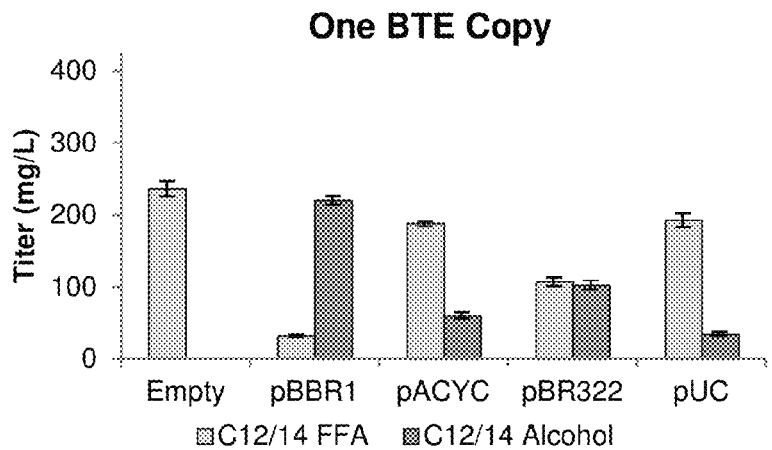
FIG. 4A
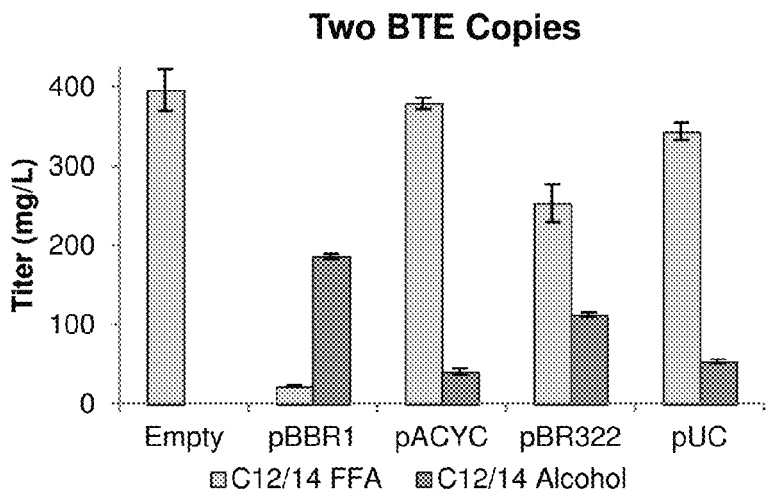
FIG. 4B
Copy Number Relative to OmpA
| | pBBR1 Uninduced | pBBR1 Induced | pACYC Induced | pBR322 Induced | pUC Induced |
|---|---|---|---|---|---|
| Antibiotic | kan | kan | cm | amp | amp |
| $OD_{600}$ 0.4 | 2.91 ± 0.23 | 1.74 ± 0.25 | 7.26 ± 1.33 | 14.52 ± 1.93 | 56.4 ± 19.9 |
| 24 hour | 8.33 ± 1.43 | 2.10 ± 0.27 | 8.31 ± 1.13 | 1.72 ± 0.24 | 6.32 ± 0.71 |
FIG. 4C

SEQUENCE LISTING

<160> NUMBER OF SEQ ID NOS: 40

<210> SEQ ID NO 1
<211> LENGTH: 2445
<212> TYPE: DNA
<213> ORGANISM: Escherichia coli

<400> SEQUENCE: 1

```
atgatgattt tgagtattct cgctacggtt gtcctgctcg gcgcgttgtt ctatcaccgc      60
gtgagcttat ttatcagcag tctgattttg ctcgcctgga cagccgccct cggcgttgct     120
ggtctgtggt cggcgtgggt actggtgcct ctggccatta tcctcgtgcc atttaacttt     180
gcgcctatgc gtaagtcgat gatttccgcg ccggtatttc gcggtttccg taaggtgatg     240
ccgccgatgt cgcgcactga gaaagaagcg attgatgcgg gcaccacctg gtgggagggc     300
gacttgttcc agggcaagcc ggactggaaa aagctgcata actatccgca gccgcgcctg     360
accgccgaag agcaagcgtt tctcgacggc ccggtagaag aagcctgccg gatggcgaat     420
gatttccaga tcacccatga gctggcggat ctgccgccgg agttgtgggc gtaccttaaa     480
gagcatcgtt tcttcgcgat gatcatcaaa aaagagtacg gcgggctgga gttctcggct     540
tatgcccagt ctcgcgtgct gcaaaaactc tccggcgtga gcgggatcct ggcgattacc     600
gtcggcgtgc caaactcatt aggcccgggc gaactgttgc aacattacgg cactgacgag     660
cagaaagatc actatctgcc gcgtctggcg cgtggtcagg agatcccctg ctttgcactg     720
accagcccgg aagcgggttc cgatgcgggc gcgattccgg acaccgggat tgtctgcatg     780
ggcgaatggc agggccagca ggtgctgggg atgcgtctga cctggaacaa cgctacatt      840
acgctggcac cgattgcgac cgtgcttggg ctggcgttta aactctccga cccggaaaaa     900
ttactcggcg gtgcagaaga tttaggcatt acctgtgcgc tgatcccaac caccacgccg     960
ggcgtggaaa ttggtcgtcg ccacttcccg ctgaacgtac cgttccagaa cggaccgacg    1020
cgcggtaaag atgtcttcgt gccgatcgat tacatcatcg gcgggccgaa aatggccggg    1080
caaggctggc ggatgctggt ggagtgcctc tcggtaggcc gcggcatcac cctgccttcc    1140
aactcaaccg cgcgcgtgaa atcggtagcg ctggcaaccg cgcgcgtatg ctcacattcgc    1200
cgtcagttca aaatctctat tggtaagatg gaagggattg aagagccgct ggcgcgtatt    1260
gccggtaatg cctacgtgat ggatgctgcg gcatcgctga ttacctacgg cattatgctc    1320
ggcgaaaaac ctgccgtgct gtcggctatc gttaagtatc actgtaccca ccgcgggcag    1380
cagtcgatta ttgatgcgat ggatattacc ggcggtaaag cattatgct cgggcaaagc    1440
aacttcctgg cgcgtgctta ccagggcgca ccgattgcca tcaccgttga aggggctaac    1500
attctgaccc gcagcatgat gatcttcgga caaggagcga ttcgttgcca tccgtacgtg    1560
ctggaagaga tggaagcggc gaagaacaat gacgtcaacg cgttcgataa actgttgttc    1620
aaacatatcg gtcacgtcgg tagcaacaaa gttcgcagct tctggctggg cctgacgcgc    1680
ggtttaacca gcagcacgcc aaccggcgat gccactaaac gctactatca gcacctgaac    1740
cgcctgagcg ccaacctcgc cctgctttct gatgtctcga tggcagtgct gggcggcagc    1800
ctgaaacgtc gcgagcgcat ctcggcccgt ctgggggata ttttaagcca gctctacctc    1860
gcctctgccg tgctgaagcg ttatgacgac gaaggccgta atgaagccga cctgccgctg    1920
gtgcactggg gcgtacaaga tgcgctgtat caggctgaac aggcgatgga tgatttactg    1980
caaaacttcc cgaaccgcgt ggttgccggg ctgctgaatg tggtgatctt cccgaccgga    2040
cgtcattatc tggcaccttc tgacaagctg atcataaag tggcgaagat tttacaagtg    2100
ccgaacgcca cccgttcccg cattggtcgc ggtcagtacc tgacgccgag cgagcataat    2160
ccggttggct tgctggaaga ggcgctggtg gatgtgattg ccgccgaccc aattcatcag    2220
cggatctgta aagagctggg taaaaacctg ccgtttaccc gtctggatga actggcgcac    2280
aacgcgctgg tgaaggggct gattgataaa gatgaagccg ctattctggt gaaagctgaa    2340
```

```
gaaagccgtc tgcgcagtat taacgttgat gactttgatc cggaagagct ggcgacgaag    2400
ccggtaaagt tgccggagaa agtgcggaaa gttgaagccg cgtaa                    2445
```

<210> SEQ ID NO 2
<211> LENGTH: 814
<212> TYPE: PRT
<213> ORGANISM: Escherichia coli

<400> SEQUENCE: 2

```
Met Met Ile Leu Ser Ile Leu Ala Thr Val Leu Leu Gly Ala Leu
1               5                   10                  15

Phe Tyr His Arg Val Ser Leu Phe Ile Ser Ser Leu Ile Leu Ala
                20                  25                  30

Trp Thr Ala Ala Leu Gly Val Ala Gly Leu Trp Ser Ala Trp Val Leu
            35                  40                  45

Val Pro Leu Ala Ile Ile Leu Val Pro Phe Asn Phe Ala Pro Met Arg
    50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asp Ala Gly Thr Thr
                85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Gln Ala Phe Leu
        115                 120                 125

Asp Gly Pro Val Glu Glu Ala Cys Arg Met Ala Asn Asp Phe Gln Ile
    130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
    210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Gln Val Leu Gly Met Arg
            260                 265                 270

Leu Thr Trp Asn Lys Arg Tyr Ile Thr Leu Ala Pro Ile Ala Thr Val
        275                 280                 285

Leu Gly Leu Ala Phe Lys Leu Ser Asp Pro Glu Lys Leu Leu Gly Gly
    290                 295                 300

Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
            340                 345                 350
```

-continued

```
Ile Gly Gly Pro Lys Met Ala Gly Gln Gly Trp Arg Met Leu Val Glu
        355                 360                 365
Cys Leu Ser Val Gly Arg Gly Ile Thr Leu Pro Ser Asn Ser Thr Gly
370                 375                 380
Gly Val Lys Ser Val Ala Leu Ala Thr Gly Ala Tyr Ala His Ile Arg
385                 390                 395                 400
Arg Gln Phe Lys Ile Ser Ile Gly Lys Met Glu Gly Ile Glu Glu Pro
                405                 410                 415
Leu Ala Arg Ile Ala Gly Asn Ala Tyr Val Met Asp Ala Ala Ala Ser
            420                 425                 430
Leu Ile Thr Tyr Gly Ile Met Leu Gly Glu Lys Pro Ala Val Leu Ser
        435                 440                 445
Ala Ile Val Lys Tyr His Cys Thr His Arg Gly Gln Gln Ser Ile Ile
    450                 455                 460
Asp Ala Met Asp Ile Thr Gly Gly Lys Gly Ile Met Leu Gly Gln Ser
465                 470                 475                 480
Asn Phe Leu Ala Arg Ala Tyr Gln Gly Ala Pro Ile Ala Ile Thr Val
                485                 490                 495
Glu Gly Ala Asn Ile Leu Thr Arg Ser Met Met Ile Phe Gly Gln Gly
            500                 505                 510
Ala Ile Arg Cys His Pro Tyr Val Leu Glu Glu Met Glu Ala Ala Lys
        515                 520                 525
Asn Asn Asp Val Asn Ala Phe Asp Lys Leu Leu Phe Lys His Ile Gly
    530                 535                 540
His Val Gly Ser Asn Lys Val Arg Ser Phe Trp Leu Gly Leu Thr Arg
545                 550                 555                 560
Gly Leu Thr Ser Thr Pro Thr Gly Asp Ala Thr Lys Arg Tyr Tyr
                565                 570                 575
Gln His Leu Asn Arg Leu Ser Ala Asn Leu Ala Leu Leu Ser Asp Val
            580                 585                 590
Ser Met Ala Val Leu Gly Gly Ser Leu Lys Arg Arg Glu Arg Ile Ser
        595                 600                 605
Ala Arg Leu Gly Asp Ile Leu Ser Gln Leu Tyr Leu Ala Ser Ala Val
    610                 615                 620
Leu Lys Arg Tyr Asp Asp Glu Gly Arg Asn Glu Ala Asp Leu Pro Leu
625                 630                 635                 640
Val His Trp Gly Val Gln Asp Ala Leu Tyr Gln Ala Glu Gln Ala Met
                645                 650                 655
Asp Asp Leu Leu Gln Asn Phe Pro Asn Arg Val Val Ala Gly Leu Leu
            660                 665                 670
Asn Val Val Ile Phe Pro Thr Gly Arg His Tyr Leu Ala Pro Ser Asp
        675                 680                 685
Lys Leu Asp His Lys Val Ala Lys Ile Leu Gln Val Pro Asn Ala Thr
    690                 695                 700
Arg Ser Arg Ile Gly Arg Gly Gln Tyr Leu Thr Pro Ser Glu His Asn
705                 710                 715                 720
Pro Val Gly Leu Leu Glu Glu Ala Leu Val Asp Val Ile Ala Ala Asp
                725                 730                 735
Pro Ile His Gln Arg Ile Cys Lys Glu Leu Gly Lys Asn Leu Pro Phe
            740                 745                 750
Thr Arg Leu Asp Glu Leu Ala His Asn Ala Leu Val Lys Gly Leu Ile
        755                 760                 765
Asp Lys Asp Glu Ala Ala Ile Leu Val Lys Ala Glu Glu Ser Arg Leu
```

|   |   |   |   |   |   |   |   |   |   |   |   |   |   |   |
|---|---|---|---|---|---|---|---|---|---|---|---|---|---|---|
| | | | 770 | | | | 775 | | | | 780 | | | |
| Arg | Ser | Ile | Asn | Val | Asp | Asp | Phe | Asp | Pro | Glu | Glu | Leu | Ala | Thr | Lys |
| 785 | | | | 790 | | | | 795 | | | | 800 |
| Pro | Val | Lys | Leu | Pro | Glu | Lys | Val | Arg | Lys | Val | Glu | Ala | Ala |
| | | | | 805 | | | | 810 |

<210> SEQ ID NO 3
<211> LENGTH: 2190
<212> TYPE: DNA
<213> ORGANISM: Escherichia coli

<400> SEQUENCE: 3

| | | | | | |
|---|---|---|---|---|---|
| atgctttaca | aaggcgacac | cctgtacctt | gactggctgg | aagatggcat | tgccgaactg | 60 |
| gtatttgatg | ccccaggttc | agttaataaa | ctcgacactg | cgaccgtcgc | cagcctcggc | 120 |
| gaggccatcg | gcgtgctgga | acagcaatca | gatctaaaag | gctgctgct | gcgttcgaac | 180 |
| aaagcagcct | ttatcgtcgg | tgctgatatc | accgaatttt | tgtccctgtt | cctcgttcct | 240 |
| gaagaacagt | taagtcagtg | gctgcacttt | gccaatagcg | tgtttaatcg | cctggaagat | 300 |
| ctgccggtgc | cgaccattgc | tgccgtcaat | ggctatgcgc | tgggcggtgg | ctgcgaatgc | 360 |
| gtgctggcga | ccgattatcg | tctggcgacg | ccggatctgc | gcatcggtct | gccggaaacc | 420 |
| aaactgggca | tcatgcctgg | cttttggcggt | tctgtacgta | tgccacgtat | gctgggcgct | 480 |
| gacagtgcgc | tggaaatcat | gccgccggt | aaagatgtcg | cgcgcgatca | ggcgctgaaa | 540 |
| atcggtctgg | tggatggcgt | agtcaaagca | gaaaaactgg | ttgaaggcgc | aaaggcggtt | 600 |
| ttacgccagg | ccattaacgg | cgacctcgac | tggaaagcaa | aacgtcagcc | gaagctggaa | 660 |
| ccactaaaac | tgagcaagat | tgaagccacc | atgagcttca | ccatcgctaa | agggatggtc | 720 |
| gcacaaacag | cggggaaaca | ttatccggcc | cccatcaccg | cagtaaaaac | cattgaagct | 780 |
| gcggcccgtt | ttggtcgtga | agaagcctta | aacctggaaa | caaaagtttt | tgtcccgctg | 840 |
| gcgcatacca | cgaagcccg | cgcactggtc | ggcattttcc | ttaacgatca | atatgtaaaa | 900 |
| ggcaaagcga | agaaactcac | caaagacgtt | gaaaccccga | acaggccgc | ggtgctgggt | 960 |
| gcaggcatta | tgggcggcgg | catcgcttac | cagtctgcgt | ggaaaggcgt | gccggttgtc | 1020 |
| atgaaagata | tcaacgacaa | gtcgttaacc | ctcggcatga | ccgaagccgc | gaaactgctg | 1080 |
| aacaagcagc | ttgagcgcgg | caagatcgat | ggtctgaaac | tggctggcgt | gatctccaca | 1140 |
| atccacccaa | cgctcgacta | cgccggattt | gaccgcgtgg | atattgtggt | agaagcggtt | 1200 |
| gttgaaaacc | cgaaagtgaa | aaaagccgta | ctggcagaaa | ccgaacaaaa | agtacgccag | 1260 |
| gataccgtgc | tggcgtctaa | cacttcaacc | attcctatca | gcgaactggc | caacgcgctg | 1320 |
| gaacgcccgg | aaaacttctg | cgggatgcac | ttctttaacc | cggtccaccg | aatgccgttg | 1380 |
| gtagaaatta | ttcgcggcga | aaaagctcc | gacgaaacca | tcgcgaaagt | tgtcgcctgg | 1440 |
| gcgagcaaga | tggcaagac | gccgattgtg | gttaacgact | gccccggctt | ctttgttaac | 1500 |
| cgcgtgctgt | tcccgtattt | cgccggtttc | agccagctgc | tgcgcgacgg | cgcggatttc | 1560 |
| cgcaagatcg | acaaagtgat | ggaaaaacag | tttggctggc | cgatgggccc | ggcatatctg | 1620 |
| ctggacgttg | tgggcattga | taccgcgcat | cacgctcagg | ctgtcatggc | agcaggcttc | 1680 |
| ccgcagcgga | tgcagaaaga | ttaccgcgat | gccatcgacg | cgctgtttga | tgccaaccgc | 1740 |
| tttggtcaga | gaacggcct | cggtttctgg | cgttataaag | aagacagcaa | aggtaagccg | 1800 |
| aagaaagaag | aagacgccgc | cgttgaagac | ctgctggcag | aagtgagcca | gccgaagcgc | 1860 |
| gatttcagcg | aagaagagat | tatcgcccgc | atgatgatcc | cgatggtcaa | cgaagtggtg | 1920 |

-continued

```
cgctgtctgg aggaaggcat tatcgccact ccggcggaag cggatatggc gctggtctac    1980
ggcctgggct ccctccgtt ccacggcggc cgttccgct ggctggacac cctcggtagc     2040
gcaaaatacc tcgatatggc acagcaatat cagcacctcg cccgctgta tgaagtgccg    2100 gaaggtctgc gtaataaagc gcgtcataac gaaccgtact atcctccggt tgagccagcc    2160
cgtccggttg cgacctgaa aacggcttaa                                      2190
```

<210> SEQ ID NO 4
<211> LENGTH: 729
<212> TYPE: PRT
<213> ORGANISM: Escherichia coli

<400> SEQUENCE: 4

```
Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
                20                  25                  30

Thr Ala Thr Val Ala Ser Leu Gly Glu Ala Ile Gly Val Leu Glu Gln
            35                  40                  45

Gln Ser Asp Leu Lys Gly Leu Leu Arg Ser Asn Lys Ala Ala Phe
        50                  55                  60

Ile Val Gly Ala Asp Ile Thr Glu Phe Leu Ser Leu Phe Leu Val Pro
65                  70                  75                  80

Glu Glu Gln Leu Ser Gln Trp Leu His Phe Ala Asn Ser Val Phe Asn
                85                  90                  95

Arg Leu Glu Asp Leu Pro Val Pro Thr Ile Ala Ala Val Asn Gly Tyr
                100                 105                 110

Ala Leu Gly Gly Gly Cys Glu Cys Val Leu Ala Thr Asp Tyr Arg Leu
            115                 120                 125

Ala Thr Pro Asp Leu Arg Ile Gly Leu Pro Glu Thr Lys Leu Gly Ile
        130                 135                 140

Met Pro Gly Phe Gly Gly Ser Val Arg Met Pro Arg Met Leu Gly Ala
145                 150                 155                 160

Asp Ser Ala Leu Glu Ile Ile Ala Ala Gly Lys Asp Val Gly Ala Asp
                165                 170                 175

Gln Ala Leu Lys Ile Gly Leu Val Asp Gly Val Val Lys Ala Glu Lys
                180                 185                 190

Leu Val Glu Gly Ala Lys Ala Val Leu Arg Gln Ala Ile Asn Gly Asp
            195                 200                 205

Leu Asp Trp Lys Ala Lys Arg Gln Pro Lys Leu Glu Pro Leu Lys Leu
        210                 215                 220

Ser Lys Ile Glu Ala Thr Met Ser Phe Thr Ile Ala Lys Gly Met Val
225                 230                 235                 240

Ala Gln Thr Ala Gly Lys His Tyr Pro Ala Pro Ile Thr Ala Val Lys
                245                 250                 255

Thr Ile Glu Ala Ala Ala Arg Phe Gly Arg Glu Ala Leu Asn Leu
                260                 265                 270

Glu Asn Lys Ser Phe Val Pro Leu Ala His Thr Asn Glu Ala Arg Ala
            275                 280                 285

Leu Val Gly Ile Phe Leu Asn Asp Gln Tyr Val Lys Gly Lys Ala Lys
        290                 295                 300

Lys Leu Thr Lys Asp Val Glu Thr Pro Lys Gln Ala Ala Val Leu Gly
305                 310                 315                 320
```

-continued

```
Ala Gly Ile Met Gly Gly Ile Ala Tyr Gln Ser Ala Trp Lys Gly
            325                 330                 335

Val Pro Val Val Met Lys Asp Ile Asn Asp Lys Ser Leu Thr Leu Gly
            340                 345                 350

Met Thr Glu Ala Ala Lys Leu Leu Asn Lys Gln Leu Glu Arg Gly Lys
            355                 360                 365

Ile Asp Gly Leu Lys Leu Ala Gly Val Ile Ser Thr Ile His Pro Thr
370                 375                 380

Leu Asp Tyr Ala Gly Phe Asp Arg Val Asp Ile Val Val Glu Ala Val
385                 390                 395                 400

Val Glu Asn Pro Lys Val Lys Lys Ala Val Leu Ala Glu Thr Glu Gln
            405                 410                 415

Lys Val Arg Gln Asp Thr Val Leu Ala Ser Asn Thr Ser Thr Ile Pro
            420                 425                 430

Ile Ser Glu Leu Ala Asn Ala Leu Glu Arg Pro Glu Asn Phe Cys Gly
            435                 440                 445

Met His Phe Phe Asn Pro Val His Arg Met Pro Leu Val Glu Ile Ile
            450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Val Asn Asp Cys Pro Gly
            485                 490                 495

Phe Phe Val Asn Arg Val Leu Phe Pro Tyr Phe Ala Gly Phe Ser Gln
            500                 505                 510

Leu Leu Arg Asp Gly Ala Asp Phe Arg Lys Ile Asp Lys Val Met Glu
            515                 520                 525

Lys Gln Phe Gly Trp Pro Met Gly Pro Ala Tyr Leu Leu Asp Val Val
            530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
            565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Glu Asp Ala Ala Val
            595                 600                 605

Glu Asp Leu Leu Ala Glu Val Ser Gln Pro Lys Arg Asp Phe Ser Glu
            610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
            645                 650                 655

Ala Leu Val Tyr Gly Leu Gly Phe Pro Pro Phe His Gly Gly Ala Phe
            660                 665                 670

Arg Trp Leu Asp Thr Leu Gly Ser Ala Lys Tyr Leu Asp Met Ala Gln
            675                 680                 685

Gln Tyr Gln His Leu Gly Pro Leu Tyr Glu Val Pro Glu Gly Leu Arg
            690                 695                 700

Asn Lys Ala Arg His Asn Glu Pro Tyr Tyr Pro Val Glu Pro Ala
705                 710                 715                 720

Arg Pro Val Gly Asp Leu Lys Thr Ala
            725
```

<210> SEQ ID NO 5
<211> LENGTH: 2145
<212> TYPE: DNA
<213> ORGANISM: Escherichia coli

<400> SEQUENCE: 5

| | | | | | |
|---|---|---|---|---|---|
| atggaaatga | catcagcgtt | taccottaat | gttcgtctgg | acaacattgc | cgttatcacc | 60 |
| atcgacgtac | cgggtgagaa | atgaatacc | ctgaaggcgg | agtttgcctc | gcaggtgcgc | 120 |
| gccattatta | agcaactccg | tgaaaacaaa | gagttgcgag | gcgtggtgtt | tgtctccgct | 180 |
| aaaccggaca | acttcattgc | tggcgcagac | atcaacatga | tcggcaactg | caaaacggcg | 240 |
| caagaagcgg | aagctctggc | gcggcagggc | caacagttga | tggcggagat | tcatgctttg | 300 |
| cccattcagg | ttatcgcggc | tattcatggc | gcttgcctgg | gtggtgggct | ggagttggcg | 360 |
| ctggcgtgcc | acgtcgcgt | ttgtactgac | gatcctaaaa | cggtgctcgg | tttgcctgaa | 420 |
| gtacaacttg | gattgttacc | cggttcaggc | ggcacccagc | gtttaccgcg | tctgataggc | 480 |
| gtcagcacag | cattagagat | gatcctcacc | ggaaaacaac | ttcgggcgaa | acaggcatta | 540 |
| aagctggggc | tggtggatga | cgttgttccg | cactccattc | tgctggaagc | cgctgttgag | 600 |
| ctggcaaaga | aggagcgccc | atcttcccgc | cctctacctg | tacgcgagcg | tattctggcg | 660 |
| gggccgttag | gtcgtgcgct | gctgttcaaa | atggtcggca | agaaaacaga | cacaaaaact | 720 |
| caaggcaatt | atccggcgac | agaacgcatc | ctggaggttg | ttgaaacggg | attagcgcag | 780 |
| ggcaccagca | gcggttatga | cgccgaagct | cgggcgtttg | gcgaactggc | gatgacgcca | 840 |
| caatcgcagg | cgctgcgtag | tatcttttt | gccagtacgg | acgtgaagaa | agatcccggc | 900 |
| agtgatgcgc | cgcctgcgcc | attaaacagc | gtggggattt | taggtggtgg | cttgatgggc | 960 |
| ggcggtattg | cttatgtcac | tgcttgtaaa | gcggggattc | cggtcagaat | taaagatatc | 1020 |
| aaccocgcagg | gcataaatca | tgcgctgaag | tacagttggg | atcagctgga | gggcaaagtt | 1080 |
| cgccgtcgtc | atctcaaagc | cagcgaacgt | gacaaacagc | tggcattaat | ctccggaacg | 1140 |
| acggactatc | gcggctttgc | ccatcgcgat | ctgattattg | aagcggtgtt | tgaaaatctc | 1200 |
| gaattgaaac | aacagatggt | ggcggaagtt | gagcaaaatt | gcgccgctca | taccatcttt | 1260 |
| gcttcgaata | cgtcatcttt | accgattggt | gatatcgccg | ctcacgccac | gcgacctgag | 1320 |
| caagttatcg | gcctgcattt | cttcagtccg | gtggaaaaaa | tgccgctggt | ggagattatt | 1380 |
| cctcatgcgg | ggacatcggc | gcaaaccatc | gctaccacga | taaaactggc | gaaaaaacag | 1440 |
| ggtaaaacgc | caattgtcgt | gcgtgacaaa | ccggttttt | acgtcaatcg | catcttagcg | 1500 |
| ccttacatta | atgaagctat | ccgcatgttg | acccaaggtg | aacgggtaga | gcacattgat | 1560 |
| gccgcgctag | tgaaatttgg | ttttccggta | ggcccaatcc | aacttttgga | tgaggtagga | 1620 |
| atcgacaccg | ggactaaaat | tattcctgta | ctggaagccg | cttatggaga | acgttttagc | 1680 |
| gcgcctgcaa | atgttgtttc | ttcaattttg | aacgacgatc | gcaaaggcag | aaaaaatggc | 1740 |
| cggggtttct | atctttatgg | tcagaaaggg | cgtaaaagca | aaaaacaggt | cgatcccgcc | 1800 |
| atttacccgc | tgattggcac | acaagggcag | gggcgaatct | ccgcaccgca | ggttgctgaa | 1860 |
| cggtgtgtga | tgttgatgct | gaatgaagca | gtacgttgtg | ttgatgagca | ggttatccgt | 1920 |
| agcgtgcgtg | acggggatat | tggcgcggta | tttggcattg | gttttccgcc | atttctcggt | 1980 |
| ggaccgttcc | gctatatcga | ttctctcggc | gcgggcgaag | tggttgcaat | aatgcaacga | 2040 |
| cttgccacgc | agtatggttc | ccgttttacc | ccttgcgagc | gtttggtcga | gatgggcgcg | 2100 |
| cgtggggaaa | gtttttggaa | aacaactgca | actgacctgc | aataa | | 2145 |

<210> SEQ ID NO 6
<211> LENGTH: 714
<212> TYPE: PRT
<213> ORGANISM: Escherichia coli

<400> SEQUENCE: 6

```
Met Glu Met Thr Ser Ala Phe Thr Leu Asn Val Arg Leu Asp Asn Ile
1               5                   10                  15

Ala Val Ile Thr Ile Asp Val Pro Gly Glu Lys Met Asn Thr Leu Lys
            20                  25                  30

Ala Glu Phe Ala Ser Gln Val Arg Ala Ile Ile Lys Gln Leu Arg Glu
        35                  40                  45

Asn Lys Glu Leu Arg Gly Val Val Phe Val Ser Ala Lys Pro Asp Asn
50                  55                  60

Phe Ile Ala Gly Ala Asp Ile Asn Met Ile Gly Asn Cys Lys Thr Ala
65                  70                  75                  80

Gln Glu Ala Glu Ala Leu Ala Arg Gln Gly Gln Gln Leu Met Ala Glu
                85                  90                  95

Ile His Ala Leu Pro Ile Gln Val Ile Ala Ala Ile His Gly Ala Cys
            100                 105                 110

Leu Gly Gly Gly Leu Glu Leu Ala Leu Ala Cys His Gly Arg Val Cys
        115                 120                 125

Thr Asp Asp Pro Lys Thr Val Leu Gly Leu Pro Glu Val Gln Leu Gly
130                 135                 140

Leu Leu Pro Gly Ser Gly Gly Thr Gln Arg Leu Pro Arg Leu Ile Gly
145                 150                 155                 160

Val Ser Thr Ala Leu Glu Met Ile Leu Thr Gly Lys Gln Leu Arg Ala
                165                 170                 175

Lys Gln Ala Leu Lys Leu Gly Leu Val Asp Asp Val Val Pro His Ser
            180                 185                 190

Ile Leu Leu Glu Ala Ala Val Glu Leu Ala Lys Lys Glu Arg Pro Ser
        195                 200                 205

Ser Arg Pro Leu Pro Val Arg Glu Arg Ile Leu Ala Gly Pro Leu Gly
210                 215                 220

Arg Ala Leu Leu Phe Lys Met Val Gly Lys Lys Thr Glu His Lys Thr
225                 230                 235                 240

Gln Gly Asn Tyr Pro Ala Thr Glu Arg Ile Leu Glu Val Val Glu Thr
                245                 250                 255

Gly Leu Ala Gln Gly Thr Ser Ser Gly Tyr Asp Ala Glu Ala Arg Ala
            260                 265                 270

Phe Gly Glu Leu Ala Met Thr Pro Gln Ser Gln Ala Leu Arg Ser Ile
        275                 280                 285

Phe Phe Ala Ser Thr Asp Val Lys Lys Asp Pro Gly Ser Asp Ala Pro
290                 295                 300

Pro Ala Pro Leu Asn Ser Val Gly Ile Leu Gly Gly Gly Leu Met Gly
305                 310                 315                 320

Gly Gly Ile Ala Tyr Val Thr Ala Cys Lys Ala Gly Ile Pro Val Arg
                325                 330                 335

Ile Lys Asp Ile Asn Pro Gln Gly Ile Asn His Ala Leu Lys Tyr Ser
            340                 345                 350

Trp Asp Gln Leu Glu Gly Lys Val Arg Arg His Leu Lys Ala Ser
        355                 360                 365

Glu Arg Asp Lys Gln Leu Ala Leu Ile Ser Gly Thr Thr Asp Tyr Arg
370                 375                 380
```

Gly Phe Ala His Arg Asp Leu Ile Ile Glu Ala Val Phe Glu Asn Leu
385                 390                 395                 400

Glu Leu Lys Gln Gln Met Val Ala Glu Val Glu Gln Asn Cys Ala Ala
            405                 410                 415

His Thr Ile Phe Ala Ser Asn Thr Ser Ser Leu Pro Ile Gly Asp Ile
        420                 425                 430

Ala Ala His Ala Thr Arg Pro Glu Gln Val Ile Gly Leu His Phe Phe
    435                 440                 445

Ser Pro Val Glu Lys Met Pro Leu Val Glu Ile Ile Pro His Ala Gly
450                 455                 460

Thr Ser Ala Gln Thr Ile Ala Thr Thr Val Lys Leu Ala Lys Lys Gln
465                 470                 475                 480

Gly Lys Thr Pro Ile Val Val Arg Asp Lys Ala Gly Phe Tyr Val Asn
                485                 490                 495

Arg Ile Leu Ala Pro Tyr Ile Asn Glu Ala Ile Arg Met Leu Thr Gln
            500                 505                 510

Gly Glu Arg Val Glu His Ile Asp Ala Ala Leu Val Lys Phe Gly Phe
        515                 520                 525

Pro Val Gly Pro Ile Gln Leu Leu Asp Glu Val Gly Ile Asp Thr Gly
    530                 535                 540

Thr Lys Ile Ile Pro Val Leu Glu Ala Ala Tyr Gly Glu Arg Phe Ser
545                 550                 555                 560

Ala Pro Ala Asn Val Val Ser Ser Ile Leu Asn Asp Asp Arg Lys Gly
                565                 570                 575

Arg Lys Asn Gly Arg Gly Phe Tyr Leu Tyr Gly Gln Lys Gly Arg Lys
            580                 585                 590

Ser Lys Lys Gln Val Asp Pro Ala Ile Tyr Pro Leu Ile Gly Thr Gln
        595                 600                 605

Gly Gln Gly Arg Ile Ser Ala Pro Gln Val Ala Glu Arg Cys Val Met
    610                 615                 620

Leu Met Leu Asn Glu Ala Val Arg Cys Val Asp Glu Gln Val Ile Arg
625                 630                 635                 640

Ser Val Arg Asp Gly Asp Ile Gly Ala Val Phe Gly Ile Gly Phe Pro
                645                 650                 655

Pro Phe Leu Gly Gly Pro Phe Arg Tyr Ile Asp Ser Leu Gly Ala Gly
            660                 665                 670

Glu Val Val Ala Ile Met Gln Arg Leu Ala Thr Gln Tyr Gly Ser Arg
        675                 680                 685

Phe Thr Pro Cys Glu Arg Leu Val Glu Met Gly Ala Arg Gly Glu Ser
    690                 695                 700

Phe Trp Lys Thr Thr Ala Thr Asp Leu Gln
705                 710

<210> SEQ ID NO 7
<211> LENGTH: 1164
<212> TYPE: DNA
<213> ORGANISM: Escherichia coli

<400> SEQUENCE: 7
atggaacagg ttgtcattgt cgatgcaatt cgcaccccga tgggccgttc gaagggcggt      60
gcttttcgta acgtgcgtgc agaagatctc tccgctcatt taatgcgtag cctgctggcg     120
cgtaaccccg gcctggaagc ggcggccctc gacgatattt actggggttg tgtgcagcag     180
acgctggagc agggttttaa tatcgcccgt aacgcggcgc tgctggcaga agtaccacac     240

```
tctgtcccgg cggttaccgt taatcgcttg tgtggttcat ccatgcaggc actgcatgac      300
gcagcacgaa tgatcatgac tggcgatgcg caggcatgtc tggttggcgg cgtggagcat      360
atgggccatg tgccgatgag tcacggcgtc gatttttcacc ccggcctgag ccgcaatgtc     420
gccaaagcgg cgggcatgat gggcttaacg gcagaaatgc tggcgcgtat gcacggtatc      480
agccgtgaaa tgcaggatgc ctttgccgcg cggtcacacg cccgcgcctg gccgccacg       540 cagtcggccg catttaaaaa tgaaatcatc ccgaccggtg gtcacgatgc cgacggcgtc      600
ctgaagcagt ttaattacga cgaagtgatt cgcccggaaa ccaccgtgga agccctcgcc      660
acgctgcgtc cggcgtttga tccagtaaac ggtatggtaa cggcgggcac atcttctgca      720
ctttccgatg gcgcagctgc catgctggtg atgagtgaaa gccgcgccca tgaattaggt      780
cttaagccgc gcgctcgtgt gcgttcgatg gcggtcgttg gttgtgaccc atcgattatg      840
ggttacggcc cggttccggc ctcgaaactg gcgctgaaaa agcggggct ttctgccagc       900 gatatcggcg tgtttgaaat gaacgaagcc tttgccgcgc agatcctgcc atgtattaaa      960
gatctgggac taattgagca gattgacgag aagatcaacc tcaacggtgg cgcgatcgcg     1020
ctgggtcatc cgctgggttg ttccggtgcg cgtatcagca ccacgctgct gaatctgatg     1080
gaacgcaaag acgttcagtt tggtctggcg acgatgtgta tcggtctggg tcagggtatt     1140
gcgacggtgt ttgagcgggt ttaa                                             1164

<210> SEQ ID NO 8
<211> LENGTH: 387
<212> TYPE: PRT
<213> ORGANISM: Escherichia coli

<400> SEQUENCE: 8

Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Val Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Val Gly Gly Val Glu His Met Gly His Val Pro Met Ser His
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Ala Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205
```

Val Ile Arg Pro Glu Thr Thr Val Glu Ala Leu Ala Thr Leu Arg Pro
    210                 215                 220

Ala Phe Asp Pro Val Asn Gly Met Val Thr Ala Gly Thr Ser Ser Ala
225                 230                 235                 240

Leu Ser Asp Gly Ala Ala Met Leu Val Met Ser Glu Ser Arg Ala
            245                 250                 255

His Glu Leu Gly Leu Lys Pro Arg Ala Arg Val Arg Ser Met Ala Val
            260                 265                 270

Val Gly Cys Asp Pro Ser Ile Met Gly Tyr Gly Pro Val Pro Ala Ser
        275                 280                 285

Lys Leu Ala Leu Lys Lys Ala Gly Leu Ser Ala Ser Asp Ile Gly Val
        290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
            355                 360                 365

Leu Ala Thr Met Cys Ile Gly Leu Gly Gln Gly Ile Ala Thr Val Phe
        370                 375                 380

Glu Arg Val
385

<210> SEQ ID NO 9
<211> LENGTH: 1311
<212> TYPE: DNA
<213> ORGANISM: Escherichia coli

<400> SEQUENCE: 9
atgggtcagg ttttaccgct ggttacccgc cagggcgatc gtatcgccat tgttagcggt      60
ttacgtacgc cttttgcccg tcaggcgacg gcttttcatg gcattcccgc ggttgattta     120
gggaagatgg tggtaggcga actgctggca cgcagcgaga tccccgccga agtgattgaa     180
caactggtct ttggtcaggt cgtacaaatg cctgaagccc caacattgc gcgtgaaatt      240 gttctcggta cgggaatgaa tgtacatacc gatgcttaca cgtcagccg cgcttgcgct      300 accagtttcc aggcagttgc aaacgtcgca gaaagcctga tggcgggaac tattcgagcg     360
gggattgccg gtgggcaga ttcctcttcg gtattgccaa ttggcgtcag taaaaaactg      420
gcgcgcgtgc tggttgatgt caacaaagct cgtaccatga ccagcgact gaaactcttc     480 tctcgcctgc gtttgcgcga cttaatgccc gtaccacctg cggtagcaga atattctacc    540
ggcttgcgga tgggcgacac cgcagagcaa atggcgaaaa cctacggcat cacccgagaa    600
cagcaagatg cattagcgca ccgttcgcat cagcgtgccg ctcaggcatg gtcagacgga    660
aaactcaaag aagaggtgat gactgccttt atccctcctt ataaacaacc gcttgtcgaa    720
gacaacaata ttcgcggtaa ttcctcgctt gccgattacg caaagctgcg cccggcgttt    780
gatcgcaaac acgaacggt aacggcggca acagtacgc cgctgaccga tggcgcggca     840
gcggtgatcc tgatgactga atcccgggcg aaagaattag gctggtgcc gctggggtat     900 ctgcgcagct acgcatttac tgcgattgat gtctggcagg acatgttgct cggtccagcc    960
tggtcaacac cgctggcgct ggagcgtgcc ggtttgacga tgagcgatct gacattgatc   1020

-continued

```
gatatgcacg aagcctttgc agctcagacg ctggcgaata ttcagttgct gggtagtgaa    1080
cgttttgctc gtgaagcact ggggcgtgca catgccactg gcgaagtgga cgatagcaaa    1140
tttaacgtgc ttggcggttc gattgcttac gggcatccct tcgcggcgac cggcgcgcgg    1200
atgattaccc agacattgca tgaacttcgc cgtcgcggcg gtggatttgg tttagttacc    1260
gcctgtgctg ccggtgggct tggcgcggca atggttctgg aggcggaata a             1311
```

<210> SEQ ID NO 10
<211> LENGTH: 436
<212> TYPE: PRT
<213> ORGANISM: Escherichia coli

<400> SEQUENCE: 10

```
Met Gly Gln Val Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Ala Val Asp Leu Gly Lys Met Val Val Gly Glu Leu
        35                  40                  45

Leu Ala Arg Ser Glu Ile Pro Ala Glu Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Lys Leu Ala Arg Val Leu
    130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ser Asp Gly Lys Leu Lys Glu
    210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Ala Ala Val Ile Leu Met Thr Glu Ser
        275                 280                 285

Arg Ala Lys Glu Leu Gly Leu Val Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Asp
```

|  |  |  | 325 |  |  |  | 330 |  |  |  | 335 |  |
| --- | --- | --- | --- | --- | --- | --- | --- | --- | --- | --- | --- | --- |
| Leu | Thr | Leu | Ile | Asp | Met | His | Glu | Ala | Phe | Ala | Ala | Gln | Thr | Leu | Ala |
|  |  |  | 340 |  |  |  | 345 |  |  |  | 350 |  |

Asn Ile Gln Leu Leu Gly Ser Glu Arg Phe Ala Arg Glu Ala Leu Gly
        355                 360                 365

Arg Ala His Ala Thr Gly Glu Val Asp Asp Ser Lys Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Gly Gly Phe
            405                 410                 415

Gly Leu Val Thr Ala Cys Ala Ala Gly Gly Leu Gly Ala Ala Met Val
            420                 425                 430

Leu Glu Ala Glu
        435

<210> SEQ ID NO 11
<211> LENGTH: 1686
<212> TYPE: DNA
<213> ORGANISM: Escherichia coli

<400> SEQUENCE: 11
ttgaagaagg tttggcttaa ccgttatccc gcggacgttc cgacggagat caaccctgac      60
cgttatcaat ctctggtaga tatgtttgag cagtcggtcg cgcgctacgc cgatcaacct     120
gcgtttgtga atatggggga ggtaatgacc ttccgcaagc tggaagaacg cagtcgcgcg     180
tttgccgctt atttgcaaca agggttgggg ctgaagaaag gcgatcgcgt tgcgttgatg     240
atgcctaatt tattgcaata tccggtggcg ctgtttggca ttttgcgtgc cgggatgatc     300
gtcgtaaacg ttaacccgtt gtataccccg cgtgagcttg agcatcagct taacgatagc     360
ggcgcatcgg cgattgttat cgtgtctaac tttgctcaca cactggaaaa agtggttgat     420
aaaaccgccg ttcagcacgt aattctgacc cgtatgggcg atcagctatc tacggcaaaa     480
ggcacggtag tcaatttcgt tgttaaatac atcaagcgtt tggtgccgaa ataccatctg     540
ccagatgcca tttcatttcg tagcgcactg cataacggct accggatgca gtacgtcaaa     600
cccgaactgg tgccggaaga tttagctttt ctgcaataca ccggcggcac cactggtgtg     660
gcgaaaggcg cgatgctgac tcaccgcaat atgctggcga acctggaaca ggttaacgcg     720
acctatggtc cgctgttgca tccgggcaaa gagctggtgg tgacggcgct gccgctgtat     780
cacattttg ccctgaccat taactgcctg ctgtttatcg aactgggtgg cagaacctg      840
cttatcacta acccgcgcga tattccaggg ttggtaaaag agttagcgaa atatccgttt     900
accgctatca cgggcgttaa caccttgttc aatgcgttgc tgaacaataa agagttccag     960
cagctggatt tctccagtct gcatctttcc gcaggcggtg ggatgccagt gcagcaagtg    1020
gtggcagagc gttgggtgaa actgaccgga cagtatctgc tggaaggcta tggccttacc    1080
gagtgtgcgc cgctggtcag cgttaaccca tatgatattg attatcatag tggtagcatc    1140
ggtttgccgg tgccgtcgac ggaagccaaa ctggtggatg atgatgataa tgaagtacca    1200
ccaggtcaac cgggtgagct ttgtgtcaaa ggaccgcagg tgatgctggg ttactggcag    1260
cgtcccgatg ctaccgatga aatcatcaaa aatggctggt acacaccgg cgacatcgcg     1320
gtaatggatg aagaaggatt cctgcgcatt gtcgatcgta aaaagacat gattctggtt     1380
tccggtttta acgtctatcc caacgagatt gaagatgtcg tcatgcagca tcctggcgta    1440

-continued

```
caggaagtcg cggctgttgg cgtaccttcc ggctccagtg gtgaagcggt gaaatcttc      1500 gtagtgaaaa aagatccatc gcttaccgaa gagtcactgg tgactttttg ccgccgtcag     1560
ctcacgggat acaaagtacc gaagctggtg gagtttcgtg atgagttacc gaaatctaac    1620
gtcggaaaaa ttttgcgacg agaattacgt gacgaagcgc gcggcaaagt ggacaataaa    1680
gcctga                                                                1686
```

```
<210> SEQ ID NO 12
<211> LENGTH: 561
<212> TYPE: PRT
<213> ORGANISM: Escherichia coli

<400> SEQUENCE: 12

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
    130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
```

|     |     | 325 |     |     |     | 330 |     |     |     | 335 |     |
| --- | --- | --- | --- | --- | --- | --- | --- | --- | --- | --- | --- |

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
            355                 360                 365

Asn Pro Tyr Asp Ile Asp Tyr His Ser Gly Ser Ile Gly Leu Pro Val
            370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                    405                 410                 415

Gly Tyr Trp Gln Arg Pro Asp Ala Thr Asp Glu Ile Ile Lys Asn Gly
                    420                 425                 430

Trp Leu His Thr Gly Asp Ile Ala Val Met Asp Glu Glu Gly Phe Leu
                    435                 440                 445

Arg Ile Val Asp Arg Lys Lys Asp Met Ile Leu Val Ser Gly Phe Asn
                    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                    485                 490                 495

Val Lys Ile Phe Val Val Lys Lys Asp Pro Ser Leu Thr Glu Glu Ser
                    500                 505                 510

Leu Val Thr Phe Cys Arg Arg Gln Leu Thr Gly Tyr Lys Val Pro Lys
                    515                 520                 525

Leu Val Glu Phe Arg Asp Glu Leu Pro Lys Ser Asn Val Gly Lys Ile
                    530                 535                 540

Leu Arg Arg Glu Leu Arg Asp Glu Ala Arg Gly Lys Val Asp Asn Lys
545                 550                 555                 560

Ala

<210> SEQ ID NO 13
<211> LENGTH: 1683
<212> TYPE: DNA
<213> ORGANISM: Pseudomonas putida

<400> SEQUENCE: 13

```
atgttgcaga cacgcatcat caagcccgcc gagggcgcct atgcctatcc attgctgatc      60
aagcgcctgc tgatgtccgg cagccgctat gaaaagaccc gggaaatcgt ctaccgcgac     120
cagatgcggc tgacgtatcc acagctcaac gagcgcattg cccgcctggc caacgtgctg     180
accgaggccg ggtcaaggc cggtgacacc gtggcggtga tggactggga cagccatcgc     240
tacctggaat gcatgttcgc catcccgatg atcggcgctg tggtgcacac catcaacgtg     300
cgcctgtcgc ccgagcagat cctctacacc atgaaccatg ccgaagaccg cgtggtgctg     360
gtcaacagcg acttcgtcgg cctgtaccag gccatcgccg gcagctgac cactgtcgac     420
aagaccctgc tactgaccga tggcccggac aagactgccg aactgcccgg tctggtcggc     480
gagtatgagc agctgctggc tgctgccagc ccgcgctacg acttcccgga tttcgacgag     540
aattcggtgg ccactaccct ctacaccact ggcaccaccg gtaaccccaa gggcgtgtat     600
ttcagtcacc gccagctggt gctgcacacc ctggccgagg cctcggtcac cggcagtatc     660
gacagcgtgc gcctgctggg cagcaacgat gtgtacatgc ccatcacccc gatgttccac     720
gtgcatgcct ggggcatccc ctacgctgcc accatgctcg gcatgaagca ggtgtaccca     780
```

```
gggcgctacg agccggacat gctggtcaag ctttggcgtg aagagaaggt cactttctcc      840
cactgcgtgc cgaccatcct gcagatgctg ctcaactgcc cgaacgccca ggggcaggac      900
ttcggcggct ggaagatcat catcggcggc agctcgctca accgttcgct gtaccaggcc      960
gccctggcgc gcggcatcca gctgaccgcc gcgtatggca tgtcggaaac ctgcccgctg     1020
atctccgcgg cacacctgaa cgatgaactg caggccggca gcgaggatga gcgcgtcact     1080
taccgtatca aggccggtgt gccggtgccg ttggtcgaag cggccatcgt cgacggcgaa     1140
ggcaacttcc tgcccgccga tggtgaaacc cagggcgagc tggtactgcg tgcgccgtgg     1200
ctgaccatgg gctacttcaa ggagccggag aagagcgagg agctgtggca gggcggctgg     1260
ctgcacaccg gtgacgtcgc caccctcgac ggcatgggct acatcgacat ccgcgaccgc     1320
atcaaggatg tgatcaagac cggtggcgag tgggtttcct cgctcgacct ggaagacctg     1380
atcagccgcc acccggccgt gcgcgaagtg gcggtggtgg ggtggccga cccgcagtgg     1440 ggtgagcgcc cgtttgccct gctggtggca cgtgacggcc acgatatcga cgccaaggcg     1500
ctgaaggaac acctcaagcc attcgtcgag caaggtcata tcaacaagtg ggcgattcca     1560
agccagatcg cccttgttac tgaaattccc aagaccagtg tcggcaagct cgacaagaaa     1620
cgcattcgcc aggacatcgt ccagtggcag gccagcaaca gcgcgttcct ttccacgttg     1680
taa                                                                   1683
```

<210> SEQ ID NO 14
<211> LENGTH: 560
<212> TYPE: PRT
<213> ORGANISM: Pseudomonas putida

<400> SEQUENCE: 14

```
Met Leu Gln Thr Arg Ile Ile Lys Pro Ala Glu Gly Ala Tyr Ala Tyr
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Gln Met Arg Leu Thr Tyr Pro Gln
        35                  40                  45

Leu Asn Glu Arg Ile Ala Arg Leu Ala Asn Val Leu Thr Glu Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val His
            85                  90                  95

Thr Ile Asn Val Arg Leu Ser Pro Glu Gln Ile Leu Tyr Thr Met Asn
            100                 105                 110

His Ala Glu Asp Arg Val Val Leu Val Asn Ser Asp Phe Val Gly Leu
        115                 120                 125

Tyr Gln Ala Ile Ala Gly Gln Leu Thr Thr Val Asp Lys Thr Leu Leu
    130                 135                 140

Leu Thr Asp Gly Pro Asp Lys Thr Ala Glu Leu Pro Gly Leu Val Gly
145                 150                 155                 160

Glu Tyr Glu Gln Leu Leu Ala Ala Ala Ser Pro Arg Tyr Asp Phe Pro
            165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205
```

His Thr Leu Ala Glu Ala Ser Val Thr Gly Ser Ile Asp Ser Val Arg
    210                 215                 220

Leu Leu Gly Ser Asn Asp Val Tyr Met Pro Ile Thr Pro Met Phe His
225                 230                 235                 240

Val His Ala Trp Gly Ile Pro Tyr Ala Ala Thr Met Leu Gly Met Lys
                    245                 250                 255

Gln Val Tyr Pro Gly Arg Tyr Glu Pro Asp Met Leu Val Lys Leu Trp
                260                 265                 270

Arg Glu Glu Lys Val Thr Phe Ser His Cys Val Pro Thr Ile Leu Gln
            275                 280                 285

Met Leu Leu Asn Cys Pro Asn Ala Gln Gly Gln Asp Phe Gly Gly Trp
        290                 295                 300

Lys Ile Ile Ile Gly Gly Ser Ser Leu Asn Arg Ser Leu Tyr Gln Ala
305                 310                 315                 320

Ala Leu Ala Arg Gly Ile Gln Leu Thr Ala Ala Tyr Gly Met Ser Glu
                325                 330                 335

Thr Cys Pro Leu Ile Ser Ala Ala His Leu Asn Asp Glu Leu Gln Ala
                340                 345                 350

Gly Ser Glu Asp Glu Arg Val Thr Tyr Arg Ile Lys Ala Gly Val Pro
            355                 360                 365

Val Pro Leu Val Glu Ala Ala Ile Val Asp Gly Glu Gly Asn Phe Leu
        370                 375                 380

Pro Ala Asp Gly Glu Thr Gln Gly Glu Leu Val Leu Arg Ala Pro Trp
385                 390                 395                 400

Leu Thr Met Gly Tyr Phe Lys Glu Pro Glu Lys Ser Glu Glu Leu Trp
                405                 410                 415

Gln Gly Gly Trp Leu His Thr Gly Asp Val Ala Thr Leu Asp Gly Met
                420                 425                 430

Gly Tyr Ile Asp Ile Arg Asp Arg Ile Lys Asp Val Ile Lys Thr Gly
            435                 440                 445

Gly Glu Trp Val Ser Ser Leu Asp Leu Glu Asp Leu Ile Ser Arg His
        450                 455                 460

Pro Ala Val Arg Glu Val Ala Val Val Gly Val Ala Asp Pro Gln Trp
465                 470                 475                 480

Gly Glu Arg Pro Phe Ala Leu Leu Val Ala Arg Asp Gly His Asp Ile
                485                 490                 495

Asp Ala Lys Ala Leu Lys Glu His Leu Lys Pro Phe Val Glu Gln Gly
                500                 505                 510

His Ile Asn Lys Trp Ala Ile Pro Ser Gln Ile Ala Leu Val Thr Glu
            515                 520                 525

Ile Pro Lys Thr Ser Val Gly Lys Leu Asp Lys Lys Arg Ile Arg Gln
        530                 535                 540

Asp Ile Val Gln Trp Gln Ala Ser Asn Ser Ala Phe Leu Ser Thr Leu
545                 550                 555                 560

<210> SEQ ID NO 15
<211> LENGTH: 1986
<212> TYPE: DNA
<213> ORGANISM: Marinobacter hydrocarbonoclasticus

<400> SEQUENCE: 15
atgaattatt tcctgacagg cggcaccggt tttatcggtc gttttctggt tgagaaactc    60
ttggcgcgcg gcggcaccgt gtatgttctg gttcgcgagc agtcccagga caagctggag   120

```
cggctccggg agcgctgggg tgcagacgac aagcaagtga aggctgtgat cggcgacctc      180
accagcaaaa accttggtat tgacgcgaaa acgctgaaat cactgaaagg aaatatcgac      240
cacgtattcc atcttgccgc ggtctacgac atgggcgcag acgaagaagc ccaggccgcc      300
accaatatcg aaggcaccag gcggctgtt caggccgccg aagccatggg cgccaagcat       360
ttccatcatg tgtcatccat cgcggcagcg ggtctgttca agggtatctt ccgggaggat      420
atgttcgaag aagccgagaa gcttgatcat ccttacctgc gcaccaagca cgaatccgaa      480
aaagttgtgc gtgaagaatg caaggttccg ttccgcatct accgccctgg tatggtcatt      540
ggccattcgg aaaccggcga atggacaag gttgacgggc cctattactt cttcaagatg       600
attcagaaga tccgtcatgc gttgccccag tgggtaccca ccatcggtat tgaaggtggc      660
cggctgaaca ttgtgccggt ggatttcgtg gtcgatgcac tggatcacat tgcccatctg     720
gaaggcgaag atggcaactg tttccatctg gtggactccg atccgtataa ggtgggtgag     780
atcctcaata ttttctgcga ggccggccat gcccccccgca tgggtatgcg catcgattcc    840
cggatgttcg gttttattcc gccgtttatt cgccagagca tcaagaatct gcctccggtc     900
aagcgcatta ctggtgcgct tctggatgac atgggcattc cgccctcggt gatgtccttc     960
attaattacc cgacccgttt tgatacccgg agctggagc gggttctgaa gggcacagac     1020
attgaggtgc gcgtctgcc gtcctatgcc ccggttatct gggactactg ggagcgcaat    1080 ctggaccccgg acctgttcaa ggaccgcacc ctcaagggca cggttgaagg taaggtttgc    1140
gtggtcaccg gcgcgacctc gggtattggc ctggcaacgg cagagaagct ggcagaggcc    1200
ggtgccattc tggtcattgg tgcgcgcacc aaggaaactc tggatgaagt ggcggccagt    1260
ctggaggcca agggtggcaa cgtgcatgcg taccagtgcg acttttcgga catggacgac    1320
tgcgaccgct ttgtgaagac ggtgctggat aatcacggcc acgtggatgt actggtgaat    1380
aacgcgggtc gctccatccg ccgctcgctg gcgttgtctt ttgaccggtt ccacgatttt    1440
gagcggacca tgcagctgaa ctactttggc tccgttcggc tgatcatggg ctttgcgcca    1500
gccatgctgg agcgtcgccg cgggcacgtg gtgaatattt cttccatcgg ggtacttacc    1560
aacgctccgc gtttctcggc ctatgtctcc tcgaaatccg cactggacgc gttcagccgc    1620
tgtgccgctg cagaatggtc ggatcgcaac gtgaccttca ccaccatcaa catgccgttg    1680
gtgaaaacgc cgatgatcgc gcccaccaag atctacgatt ccgtgccgac gctgacgccg    1740
gatgaagccg cccagatggt ggcggatgcg attgtgtacc ggcccaagcg cattgccacc    1800
cgtcttggcg tgttcgcgca ggttctgcat gcgctggcac cgaagatggg tgagatcatt    1860
atgaacactg gctaccggat gttcccggat tctccagcag ccgctggcag caagtccggc    1920
gaaaagccga agtctctac cgagcaggtg gcctttgcgg cgattatgcg ggggatatac    1980
tggtaa                                                                1986
```

<210> SEQ ID NO 16
<211> LENGTH: 661
<212> TYPE: PRT
<213> ORGANISM: Marinobacter hydrocarbonoclasticus

<400> SEQUENCE: 16

```
Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
```

-continued

```
                35                  40                  45
Asp Asp Lys Gln Val Lys Ala Val Ile Gly Asp Leu Thr Ser Lys Asn
 50                  55                  60
Leu Gly Ile Asp Ala Lys Thr Leu Lys Ser Leu Lys Gly Asn Ile Asp
 65                  70                  75                  80
His Val Phe His Leu Ala Val Tyr Asp Met Gly Ala Asp Glu Glu
                 85                  90                  95
Ala Gln Ala Ala Thr Asn Ile Glu Gly Thr Arg Ala Ala Val Gln Ala
                100                 105                 110
Ala Glu Ala Met Gly Ala Lys His Phe His His Val Ser Ser Ile Ala
                115                 120                 125
Ala Ala Gly Leu Phe Lys Gly Ile Phe Arg Glu Asp Met Phe Glu Glu
                130                 135                 140
Ala Glu Lys Leu Asp His Pro Tyr Leu Arg Thr Lys His Glu Ser Glu
145                 150                 155                 160
Lys Val Val Arg Glu Glu Cys Lys Val Pro Phe Arg Ile Tyr Arg Pro
                165                 170                 175
Gly Met Val Ile Gly His Ser Glu Thr Gly Glu Met Asp Lys Val Asp
                180                 185                 190
Gly Pro Tyr Tyr Phe Phe Lys Met Ile Gln Lys Ile Arg His Ala Leu
                195                 200                 205
Pro Gln Trp Val Pro Thr Ile Gly Ile Glu Gly Arg Leu Asn Ile
210                 215                 220
Val Pro Val Asp Phe Val Val Asp Ala Leu Asp His Ile Ala His Leu
225                 230                 235                 240
Glu Gly Glu Asp Gly Asn Cys Phe His Leu Val Asp Ser Asp Pro Tyr
                245                 250                 255
Lys Val Gly Glu Ile Leu Asn Ile Phe Cys Glu Ala Gly His Ala Pro
                260                 265                 270
Arg Met Gly Met Arg Ile Asp Ser Arg Met Phe Gly Phe Ile Pro Pro
                275                 280                 285
Phe Ile Arg Gln Ser Ile Lys Asn Leu Pro Pro Val Lys Arg Ile Thr
290                 295                 300
Gly Ala Leu Leu Asp Asp Met Gly Ile Pro Pro Ser Val Met Ser Phe
305                 310                 315                 320
Ile Asn Tyr Pro Thr Arg Phe Asp Thr Arg Glu Leu Glu Arg Val Leu
                325                 330                 335
Lys Gly Thr Asp Ile Glu Val Pro Arg Leu Pro Ser Tyr Ala Pro Val
                340                 345                 350
Ile Trp Asp Tyr Trp Glu Arg Asn Leu Asp Pro Asp Leu Phe Lys Asp
                355                 360                 365
Arg Thr Leu Lys Gly Thr Val Glu Gly Lys Val Cys Val Val Thr Gly
                370                 375                 380
Ala Thr Ser Gly Ile Gly Leu Ala Thr Ala Glu Lys Leu Ala Glu Ala
385                 390                 395                 400
Gly Ala Ile Leu Val Ile Gly Ala Arg Thr Lys Glu Thr Leu Asp Glu
                405                 410                 415
Val Ala Ala Ser Leu Glu Ala Lys Gly Gly Asn Val His Ala Tyr Gln
                420                 425                 430
Cys Asp Phe Ser Asp Met Asp Asp Cys Asp Arg Phe Val Lys Thr Val
                435                 440                 445
Leu Asp Asn His Gly His Val Asp Val Leu Val Asn Asn Ala Gly Arg
450                 455                 460
```

```
Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
            485                 490                 495

Gly Phe Ala Pro Ala Met Leu Glu Arg Arg Gly His Val Val Asn
                500                 505                 510

Ile Ser Ser Ile Gly Val Leu Thr Asn Ala Pro Arg Phe Ser Ala Tyr
                515                 520                 525

Val Ser Ser Lys Ser Ala Leu Asp Ala Phe Ser Arg Cys Ala Ala Ala
530                 535                 540

Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
                580                 585                 590

Tyr Arg Pro Lys Arg Ile Ala Thr Arg Leu Gly Val Phe Ala Gln Val
            595                 600                 605

Leu His Ala Leu Ala Pro Lys Met Gly Glu Ile Ile Met Asn Thr Gly
            610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660

<210> SEQ ID NO 17
<211> LENGTH: 930
<212> TYPE: DNA
<213> ORGANISM: Umbellularia californica
<220> FEATURE:
<221> NAME/KEY: CDS
<222> LOCATION: (21)..(923)

<400> SEQUENCE: 17
cccgggagga ggattataaa atg act cta gag tgg aaa ccg aaa cca aaa ctg      53
                     Met Thr Leu Glu Trp Lys Pro Lys Pro Lys Leu
                      1               5                  10 cct caa ctg ctg gat gat cac ttc ggt ctg cac ggt ctg gtg ttt cgt      101
Pro Gln Leu Leu Asp Asp His Phe Gly Leu His Gly Leu Val Phe Arg
            15                  20                  25 cgt act ttc gca att cgt tct tat gaa gtg ggt cca gat cgt tct acc      149
Arg Thr Phe Ala Ile Arg Ser Tyr Glu Val Gly Pro Asp Arg Ser Thr
        30                  35                  40 tcc atc ctg gcc gtc atg aac cac atg cag gaa gcc acc ctg aat cac      197
Ser Ile Leu Ala Val Met Asn His Met Gln Glu Ala Thr Leu Asn His
    45                  50                  55 gcg aaa tct gtt ggt atc ctg ggt gat ggt ttc ggc act act ctg gaa      245
Ala Lys Ser Val Gly Ile Leu Gly Asp Gly Phe Gly Thr Thr Leu Glu
60                  65                  70                  75 atg tct aaa cgt gac ctg atg tgg gta gtg cgt cgc acc cac gta gca      293
Met Ser Lys Arg Asp Leu Met Trp Val Val Arg Arg Thr His Val Ala
                80                  85                  90 gta gag cgc tac cct act tgg ggt gac act gtg gaa gtc gag tgt tgg      341
Val Glu Arg Tyr Pro Thr Trp Gly Asp Thr Val Glu Val Glu Cys Trp
            95                  100                 105
```

```
att ggc gcg tcc ggt aac aat ggt atg cgt cgc gat ttt ctg gtc cgt    389
Ile Gly Ala Ser Gly Asn Asn Gly Met Arg Arg Asp Phe Leu Val Arg
        110                 115                 120 gac tgt aaa acg ggc gaa atc ctg acg cgt tgc acc tcc ctg agc gtt    437
Asp Cys Lys Thr Gly Glu Ile Leu Thr Arg Cys Thr Ser Leu Ser Val
125                 130                 135 ctg atg aac acc cgc act cgt cgc ctg tct acc atc ccg gac gaa gtg    485
Leu Met Asn Thr Arg Thr Arg Arg Leu Ser Thr Ile Pro Asp Glu Val
140                 145                 150                 155 cgc ggt gag atc ggt cct gct ttc atc gat aac gtg gca gtt aaa gac    533
Arg Gly Glu Ile Gly Pro Ala Phe Ile Asp Asn Val Ala Val Lys Asp
                160                 165                 170 gac gaa atc aag aaa ctg caa aaa ctg aac gac tcc acc gcg gac tac    581
Asp Glu Ile Lys Lys Leu Gln Lys Leu Asn Asp Ser Thr Ala Asp Tyr
            175                 180                 185 atc cag ggc ggt ctg act ccg cgc tgg aac gac ctg gat gtt aat cag    629
Ile Gln Gly Gly Leu Thr Pro Arg Trp Asn Asp Leu Asp Val Asn Gln
        190                 195                 200 cat gtg aac aac ctg aaa tac gtt gct tgg gtc ttc gag act gtg ccg    677
His Val Asn Asn Leu Lys Tyr Val Ala Trp Val Phe Glu Thr Val Pro
205                 210                 215 gac agc att ttc gaa agc cat cac att tcc tct ttt act ctg gag tac    725
Asp Ser Ile Phe Glu Ser His His Ile Ser Ser Phe Thr Leu Glu Tyr
220                 225                 230                 235 cgt cgc gaa tgt act cgc gac tcc gtt ctg cgc agc ctg acc acc gta    773
Arg Arg Glu Cys Thr Arg Asp Ser Val Leu Arg Ser Leu Thr Thr Val
                240                 245                 250 agc ggc ggt tct agc gag gca ggt ctg gtc tgc gac cat ctg ctg caa    821
Ser Gly Gly Ser Ser Glu Ala Gly Leu Val Cys Asp His Leu Leu Gln
            255                 260                 265 ctg gaa ggc ggc tcc gaa gtc ctg cgt gcg cgt acg gag tgg cgt cca    869
Leu Glu Gly Gly Ser Glu Val Leu Arg Ala Arg Thr Glu Trp Arg Pro
        270                 275                 280 aag ctg acg gat tct ttc cgc ggc atc tcc gta att ccg gcg gaa cct    917
Lys Leu Thr Asp Ser Phe Arg Gly Ile Ser Val Ile Pro Ala Glu Pro
285                 290                 295 cgt gtt taagctt                                                    930
Arg Val
300

<210> SEQ ID NO 18
<211> LENGTH: 301
<212> TYPE: PRT
<213> ORGANISM: Umbellularia californica

<400> SEQUENCE: 18

Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
                20                  25                  30

Arg Ser Tyr Glu Val Gly Pro Asp Arg Ser Thr Ser Ile Leu Ala Val
            35                  40                  45

Met Asn His Met Gln Glu Ala Thr Leu Asn His Ala Lys Ser Val Gly
        50                  55                  60

Ile Leu Gly Asp Gly Phe Gly Thr Thr Leu Glu Met Ser Lys Arg Asp
65                  70                  75                  80

Leu Met Trp Val Val Arg Arg Thr His Val Ala Val Glu Arg Tyr Pro
                85                  90                  95

Thr Trp Gly Asp Thr Val Glu Val Glu Cys Trp Ile Gly Ala Ser Gly
```

```
              100                 105                 110
Asn Asn Gly Met Arg Asp Phe Leu Val Arg Asp Cys Lys Thr Gly
            115                 120                 125

Glu Ile Leu Thr Arg Cys Thr Ser Leu Ser Val Leu Met Asn Thr Arg
            130                 135                 140

Thr Arg Arg Leu Ser Thr Ile Pro Asp Glu Val Arg Gly Glu Ile Gly
145                 150                 155                 160

Pro Ala Phe Ile Asp Asn Val Ala Val Lys Asp Asp Glu Ile Lys Lys
                165                 170                 175

Leu Gln Lys Leu Asn Asp Ser Thr Ala Asp Tyr Ile Gln Gly Gly Leu
                180                 185                 190

Thr Pro Arg Trp Asn Asp Leu Asp Val Asn Gln His Val Asn Asn Leu
                195                 200                 205

Lys Tyr Val Ala Trp Val Phe Glu Thr Val Pro Asp Ser Ile Phe Glu
                210                 215                 220

Ser His His Ile Ser Ser Phe Thr Leu Glu Tyr Arg Arg Glu Cys Thr
225                 230                 235                 240

Arg Asp Ser Val Leu Arg Ser Leu Thr Thr Val Ser Gly Gly Ser Ser
                245                 250                 255

Glu Ala Gly Leu Val Cys Asp His Leu Leu Gln Leu Glu Gly Gly Ser
                260                 265                 270

Glu Val Leu Arg Ala Arg Thr Glu Trp Arg Pro Lys Leu Thr Asp Ser
                275                 280                 285

Phe Arg Gly Ile Ser Val Ile Pro Ala Glu Pro Arg Val
                290                 295                 300

<210> SEQ ID NO 19
<211> LENGTH: 456
<212> TYPE: DNA
<213> ORGANISM: Escherichia coli

<400> SEQUENCE: 19
ttgactacta acactcatac tctgcagatt gaagagattt tagaacttct gccgcaccgt        60
ttcccgttct tactggtgga tcgcgtgctg gattttgaag aaggtcgttt tctgcgcgca       120
gtaaaaaatg tctctgtcaa tgagccattc ttccagggcc atttccctgg aaaaccgatt       180
ttcccgggtg tgctgattct ggaagcaatg cacaggcaa caggtattct ggcgtttaaa        240
agcgtaggaa aactggaacc gggtgagctg tactacttcg ctggtattga cgaagcgcgc      300
ttcaagcgcc cggtcgtgcc tggcgatcaa atgatcatgg aagtcacttt cgaaaaaacg      360
cgccgcggcc tgacccgttt taaagggtt gctctggtcg atggtaaagt agtttgcgaa       420
gcaacgatga tgtgtgctcg tagccgggag gcctga                                456

<210> SEQ ID NO 20
<211> LENGTH: 151
<212> TYPE: PRT
<213> ORGANISM: Escherichia coli

<400> SEQUENCE: 20

Met Thr Thr Asn Thr His Thr Leu Gln Ile Glu Glu Ile Leu Glu Leu
1               5                   10                  15

Leu Pro His Arg Phe Pro Phe Leu Leu Val Asp Arg Val Leu Asp Phe
                20                  25                  30

Glu Glu Gly Arg Phe Leu Arg Ala Val Lys Asn Val Ser Val Asn Glu
            35                  40                  45
```

```
Pro Phe Phe Gln Gly His Phe Pro Gly Lys Pro Ile Phe Pro Gly Val
    50                  55                  60

Leu Ile Leu Glu Ala Met Ala Gln Ala Thr Gly Ile Leu Ala Phe Lys
65                  70                  75                  80

Ser Val Gly Lys Leu Glu Pro Gly Glu Leu Tyr Tyr Phe Ala Gly Ile
                85                  90                  95

Asp Glu Ala Arg Phe Lys Arg Pro Val Val Pro Gly Asp Gln Met Ile
            100                 105                 110

Met Glu Val Thr Phe Glu Lys Thr Arg Arg Gly Leu Thr Arg Phe Lys
        115                 120                 125

Gly Val Ala Leu Val Asp Gly Lys Val Val Cys Glu Ala Thr Met Met
    130                 135                 140

Cys Ala Arg Ser Arg Glu Ala
145                 150

<210> SEQ ID NO 21
<211> LENGTH: 720
<212> TYPE: DNA
<213> ORGANISM: Escherichia coli

<400> SEQUENCE: 21
atggtcatta aggcgcaaag cccggcgggt ttcgcggaag agtacattat tgaaagtatc      60
tggaataacc gcttccctcc cgggactatt tgcccgcag aacgtgaact ttcagaatta     120
attggcgtaa cgcgtactac gttacgtgaa gtgttacagc gtctggcacg agatggctgg    180
ttgaccattc aacatggcaa gccgacgaag gtgaataatt tctgggaaac ttccggttta    240
aatatccttg aaacactggc gcgactggat cacgaaagtg tgccgcagct tattgataat    300
ttgctgtcgg tgcgtaccaa tatttccact atttttattc gcaccgcgtt tcgtcagcat    360
cccgataaag cgcaggaagt gctggctacc gctaatgaag tggccgatca cgccgatgcc    420
tttgccgagc tggattacaa catattccgc ggcctggcgt ttgcttccgg caacccgatt    480
tacggtctga ttcttaacgg gatgaaaggg ctgtatacgc gtattggtcg tcactatttc    540
gccaatccgg aagcgcgcag tctggcgctg gcttctacc acaaactgtc ggcgttgtgc    600
agtgaaggcg cgcacgatca ggtgtacgaa acagtgcgtc gctatgggca tgagagtggc    660
gagatttggc accggatgca gaaaaatctg ccgggtgatt tagccattca ggggcgataa    720

<210> SEQ ID NO 22
<211> LENGTH: 239
<212> TYPE: PRT
<213> ORGANISM: Escherichia coli

<400> SEQUENCE: 22

Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95
```

-continued

```
Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160

Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
225                 230                 235

<210> SEQ ID NO 23
<211> LENGTH: 50
<212> TYPE: DNA
<213> ORGANISM: Artificial Sequence
<220> FEATURE:
<223> OTHER INFORMATION: Synthesized

<400> SEQUENCE: 23
gaaaggtttt gcaccattcg atggtgtcgg tgcctaatga gtgagctaac            50

<210> SEQ ID NO 24
<211> LENGTH: 50
<212> TYPE: DNA
<213> ORGANISM: Artificial Sequence
<220> FEATURE:
<223> OTHER INFORMATION: Synthesized

<400> SEQUENCE: 24
gaaaggtttt gcaccattcg atggtgtcgg tgcctaatga gtgagctaac            50

<210> SEQ ID NO 25
<211> LENGTH: 22
<212> TYPE: DNA
<213> ORGANISM: Artificial Sequence
<220> FEATURE:
<223> OTHER INFORMATION: Synthesized

<400> SEQUENCE: 25
atcgaatggt gcaaaacctt tc                                          22

<210> SEQ ID NO 26
<211> LENGTH: 20
<212> TYPE: DNA
<213> ORGANISM: Artificial Sequence
<220> FEATURE:
<223> OTHER INFORMATION: Synthesized

<400> SEQUENCE: 26
gaaacgcaaa aaggccatcc                                             20

<210> SEQ ID NO 27
<211> LENGTH: 37
<212> TYPE: DNA
```

<210> SEQ ID NO 27
<211> LENGTH: 37
<212> TYPE: DNA
<213> ORGANISM: Artificial Sequence
<220> FEATURE:
<223> OTHER INFORMATION: Synthesized

<400> SEQUENCE: 27
acacaggaaa cagaccatca ccaacaagga ccatagc        37

<210> SEQ ID NO 28
<211> LENGTH: 39
<212> TYPE: DNA
<213> ORGANISM: Artificial Sequence
<220> FEATURE:
<223> OTHER INFORMATION: Synthesized

<400> SEQUENCE: 28
tcatccgcca aaacagctta tcagtgatgg tgatgatgg     39

<210> SEQ ID NO 29
<211> LENGTH: 53
<212> TYPE: DNA
<213> ORGANISM: Artificial Sequence
<220> FEATURE:
<223> OTHER INFORMATION: Escherichia coli and synthesized sequence

<400> SEQUENCE: 29
gaaaagagct cggtaccagg aggtataaga attgaagaag gtttggctta acc     53

<210> SEQ ID NO 30
<211> LENGTH: 43
<212> TYPE: DNA
<213> ORGANISM: Artificial Sequence
<220> FEATURE:
<223> OTHER INFORMATION: Escherichia coli and synthesized sequence

<400> SEQUENCE: 30
gaaaagtcga ctctagatta tcaggcttta ttgtccactt tgc     43

<210> SEQ ID NO 31
<211> LENGTH: 66
<212> TYPE: DNA
<213> ORGANISM: Artificial Sequence
<220> FEATURE:
<223> OTHER INFORMATION: Synthesized

<400> SEQUENCE: 31
atgttaatca taaatgtcgg tgtcatcatg cgctacgctc ggcatgcgtt cctattccga     60
agttcc     66

<210> SEQ ID NO 32
<211> LENGTH: 62
<212> TYPE: DNA
<213> ORGANISM: Artificial Sequence
<220> FEATURE:
<223> OTHER INFORMATION: Synthesized

<400> SEQUENCE: 32
agcgcaaagc tgcggatgat gacgagatta ctgctgctgt tacatccgcc aaaacagcca     60
ag     62

<210> SEQ ID NO 33
<211> LENGTH: 52
<212> TYPE: DNA
<213> ORGANISM: Artificial Sequence
<220> FEATURE:
<223> OTHER INFORMATION: Pseudomonas putida KT2440 and synthesized sequences

<400> SEQUENCE: 33
gagaaagagc tcggtaccag gaggtaaaat aatgttgcag acacgcatca tc                    52

<210> SEQ ID NO 34
<211> LENGTH: 59
<212> TYPE: DNA
<213> ORGANISM: Artificial Sequence
<220> FEATURE:
<223> OTHER INFORMATION: Pseudomonas putida KT2440 and synthesized
      sequences

<400> SEQUENCE: 34
gaaaagcctg caggtctaga ttagtgatgg tgatggtgat gcaacgtgga aaggaacgc             59

<210> SEQ ID NO 35
<211> LENGTH: 19
<212> TYPE: DNA
<213> ORGANISM: Artificial Sequence
<220> FEATURE:
<223> OTHER INFORMATION: Synthesized

<400> SEQUENCE: 35
atggtctgtt tcctgtgtg                                                         19

<210> SEQ ID NO 36
<211> LENGTH: 18
<212> TYPE: DNA
<213> ORGANISM: Artificial Sequence
<220> FEATURE:
<223> OTHER INFORMATION: Synthesized

<400> SEQUENCE: 36
gctgttttgg cggatgag                                                          18

<210> SEQ ID NO 37
<211> LENGTH: 18
<212> TYPE: DNA
<213> ORGANISM: Marinobacter hydrocarbonoclasticus

<400> SEQUENCE: 37
ctatgtctcc tcgaaatc                                                          18

<210> SEQ ID NO 38
<211> LENGTH: 18
<212> TYPE: DNA
<213> ORGANISM: Marinobacter hydrocarbonoclasticus

<400> SEQUENCE: 38
gaatcgtaga tcttggtg                                                          18

<210> SEQ ID NO 39
<211> LENGTH: 20
<212> TYPE: DNA
<213> ORGANISM: Escherichia coli

<400> SEQUENCE: 39
tgttgagtac gcgatcactc                                                        20

<210> SEQ ID NO 40
<211> LENGTH: 17
<212> TYPE: DNA
<213> ORGANISM: Escherichia coli

```
<400> SEQUENCE: 40
gttgtccgga cgagtgc                                                    17
```

CELLS AND METHODS FOR PRODUCING FATTY ALCOHOLS

CROSS-REFERENCE TO RELATED APPLICATIONS

This application claims priority under 35 USC §119(e) to U.S. Provisional Patent Application 61/888,199 filed Oct. 8, 2013, the entirety of which is incorporated herein by reference.

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The present invention is directed to cells and methods for producing fatty alcohols from an unrelated carbon source, such as carbohydrates.

BACKGROUND

The finite nature of fossil fuels, as well as rising prices and environmental concerns, has spurred research to develop chemical production alternatives that are more sustainable. One such alternative is to use engineered microorganisms to convert renewable growth substrates (e.g. sugars) to metabolic products of interest. Using modern genetic techniques and synthetic biology approaches, microorganisms have been engineered to produce a wide variety of chemicals from renewable starting materials (Keasling 2012; Dellomonaco et al., 2010). Metabolic engineering offers the ability to tailor the flow of carbon to desired compounds and leverage the advantages of enzymatic biocatalysts (e.g. specificity, precision, complexity). If economic and productivity targets can be met, engineered microbes could play a large role in replacing the fraction of petroleum used to produce the chemical building blocks that enable current lifestyles.

In recent years, significant effort has focused on producing hydrophobic compounds via fatty acid biosynthesis for use as liquid transportation fuels or commodity chemicals (Lennen and Pfleger 2013). Aliphatic compounds such as fatty alcohols also have applications as detergents, emulsifiers, lubricants, and cosmetics. While fatty alcohols normally make up about 3-5 percent of the final formulation of these products, some such as solid anti-perspirants contain up to 25% fatty alcohols (Mudge et al., 2008). As of 2006, over 1.3 million tons of fatty alcohols were used worldwide each year (Mudge et al., 2008). As a whole, the industry represents over a 3 billion dollar market (Rupilius and Ahmad, 2006). Currently, fatty alcohols are produced either through processing natural fats and oils (oleochemicals) or from petrochemicals (e.g. crude oil, natural gas). In the oleochemical route, fatty acids or fatty acid methyl esters are released from triglycerides and hydrogenated to form fatty alcohols (Matheson 1996). In one common petrochemical route, paraffins are separated from kerosene, then converted to olefins, before being converted to fatty alcohols. As both processes require either modifications to biodiesel or petrochemical fuel stocks, microbial production of fatty alcohols from renewable sugars is a promising alternative.

Fatty alcohols can be generated by microorganisms endogenously (FIG. 1A) via reduction of fatty aldehydes that are made via reduction of acyl-thioesters (coenzyme A or acyl-carrier protein) (Reiser and Somerville 1997). Alternatively, fatty acids have been shown to be directly converted to fatty aldehydes via the action of a carboxylic acid reductase (Akhtar et al., 2013). Genes encoding long chain acyl-CoA reductase activity have been isolated from many organisms including bacteria (Reiser and Somerville 1997), insects (Liénard et al., 2010), birds (Hellenbrand et al., 2011), mammals (Cheng and Russell 2004), and protists (Teerawanichpan and Qiu, 2010). Many of these enzymes are used to synthesize fatty alcohols as precursors to wax esters. Three exemplary classes of reductases include reductases from soil bacteria (Reiser and Somerville, 1997; Steen et al., 2010), reductases from plants such as *Arabidopsis* or *Simmondsia* (Doan et al., 2009; Rowland and Domergue, 2012), and reductases found in marine bacteria (Willis et al., 2011; Hofvander et al., 2011). These classes differ in their ability to catalyze multiple reactions and in their substrate preference. Reductases similar to those found in *Acinetobacter* contain only the domain to catalyze conversion of acyl-thioesters to fatty aldehydes. Conversely, reductases from plants can catalyze both reductions, but generally do not have broad substrate specificity, preferring the dominant long acyl chains found in lipids. Reductases from marine bacteria catalyze both reductions and are active on a wide range of chain lengths.

While fatty acids have been produced with yields of greater than 0.2 g fatty acid per gram carbon source consumed (Dellomonaco et al., 2011; Zhang et al., 2012), the highest reported yields of fatty alcohols have been at least five fold lower. The work of Steen et al. (Steen et al., 2010) demonstrated that fatty alcohols can be produced with titers of around 60 mg/L fatty alcohol and yields of less than 0.005 g fatty alcohol/g carbon source. Further metabolic engineering and fermentation efforts have increased the titer to ~450 mg/L, but with no significant improvement in yield (Zheng et al., 2012). Alternative strategies have led to slightly higher fatty alcohol yields from a defined carbon source. One strategy reached ~350 mg/L with a yield of 0.04 g fatty alcohol/g carbon source (Akhtar et al., 2013). Another strategy achieved between 0.04 and 0.055 g fatty alcohol/g carbon source consumed (Dellomonaco et al., 2011). However, greater titers and yields are required if microorganism-based production of fatty alcohols is to replace fossil fuel-based production.

SUMMARY OF THE INVENTION

The present invention is directed recombinant cells and methods for improved yield of fatty alcohols such as 1-dodecanol and 1-tetradecanol from an unrelated carbon source (e.g. glucose). An exemplary cell of the invention comprises a bacterium such as *E. coli* that overexpresses the BTE thioesterase from *Umbellularia californica*, native FadD from *E. coli*, and the acyl-CoA reductase (MAACR) from *Marinobacter aquaeolei* VT8 in a ΔfadE genetic background. Exemplary methods of the invention include culturing such a strain in a bioreactor in the presence of a carbon source such as glucose, which is capable of generating a titer of over 1.65 g/L fatty alcohol (1.55 g/L C12-14 alcohol) and a yield of over 0.13 g fatty alcohol/g consumed glucose (0.12 g C12-14 fatty alcohol/g consumed glucose).

More generally, one aspect of the invention is directed to a recombinant cell for producing fatty alcohol. The recombinant cell comprises a recombinant thioesterase gene, a recombinant acyl-CoA synthetase gene, and a recombinant acyl-CoA reductase gene. A gene product from a gene selected from the group consisting of an acyl-CoA dehydrogenase gene, an enoyl-CoA hydratase gene, a 3-hydroxyacyl-CoA dehydrogenase gene, and a 3-ketoacyl-CoA thiolase gene is functionally deleted in the cell.

The acyl-CoA synthetase gene may encode SEQ ID NO:12 or a homolog at least about 90% identical thereto. The acyl-CoA synthetase gene may be expressed to a level greater than about 2-fold a level of expression of a native acyl-CoA synthetase gene in a corresponding cell and less than about 75-fold the level of expression of the native acyl-CoA synthase gene in the corresponding cell. The acyl-CoA synthetase gene may be included in the cell in exponential phase in an amount of from about 1 to about 5 copies per copy of genomic DNA.

The recombinant acyl-CoA reductase gene may encode an enzyme having both acyl-CoA reductase activity and aldehyde reductase activity. The acyl-CoA reductase gene may encode SEQ ID NO:16 or a sequence at least 90% identical thereto. The acyl-CoA reductase gene may be included in the cell in exponential phase in an amount of from about 1 to about 10 copies per copy of genomic DNA.

The acyl-CoA reductase gene and the acyl-CoA synthetase gene may be included in the cell at a copy ratio of from about 5:1 to about 1:1.

A relative level of expression of the recombinant acyl-CoA reductase gene with respect to level of expression of the recombinant acyl-CoA synthetase gene may be the same as that obtained by providing the recombinant acyl-CoA reductase gene with respect to the recombinant acyl-CoA synthetase gene in a copy ratio of from about 5:1 to about 1:1 when the recombinant acyl-CoA reductase gene and the recombinant acyl-CoA synthetase gene each comprises a promoter that confers a level of expression per gene copy within about +/−10% of a level of expression of the other promoter.

The recombinant cell may further comprises a recombinant aldehyde reductase gene.

The acyl-CoA dehydrogenase gene product may be functionally deleted. The acyl-CoA dehydrogenase gene may be fadE and a gene product of fadE may be functionally deleted.

A gene product from a gene selected from the group consisting of the enoyl-CoA hydratase gene, the 3-hydroxyacyl-CoA dehydrogenase gene, and the 3-ketoacyl-CoA thiolase gene may be functionally deleted. Gene products of fadA and fadI; fadB and fadJ; or fadA, fadI, fadB and fadJ may be functionally deleted.

The thioesterase gene may encode SEQ ID NO:18 or a sequence about 80% identical thereto.

The recombinant cell may be a microbial cell, such as a bacterial cell.

Another aspect of the invention comprises a method of producing fatty alcohol. The method comprises culturing a recombinant cell as described above or otherwise herein. The method may comprise culturing the recombinant cell in a medium comprising a carbohydrate and no more than about 1 g L$^{-1}$ dissolved, exogenous free fatty acid or salt thereof. The culturing may comprise adding carbohydrate in a fed-batch manner. The culturing may comprise culturing the recombinant cell in a mixture of aqueous fermentation broth and organic solvent. The culturing may be performed at least until the cell reaches a titer of fatty alcohol of at least about 1.25 g/L.

The objects and advantages of the invention will appear more fully from the following detailed description of the preferred embodiment of the invention made in conjunction with the accompanying drawings.

BRIEF DESCRIPTION OF THE DRAWINGS

FIG. 1A shows that to produce 1-dodecanol, β-oxidation is preferably blocked (ΔfadE), and ACS (FadD) activity is preferably increased from native levels. FIG. 1C shows that expression of MAACR results in production of 1-hexadecanol in each strain.

FIGS. 4A and 4B show combined titers of 1-dodecanol and 1-tetradecanol as well as residual dodecanoic and tetradecanoic acid from E. coli MHS03 (ΔfadE::trcBTE Φ(P$_{Trc}$-fadD)) (FIG. 4A) and E. coli TY30 (ΔfadE::trcBTE ΔfadAB::trcBTE Φ(P$_{Trc}$-fadD)) (FIG. 4B) harboring MAACR on four different copy number vectors. The MHS03 strain carried one BTE copy, and the TY30 strain carried two BTE copies. The Empty plasmid was ptrc99a. FIG. 4C depicts the plasmid copy number determined by qPCR (relative to ompA) for the plasmids used in FIGS. 4A and B and shows that the plasmid copy number increases from left to right as shown in each of FIGS. 4A and B. Plasmids conferring resistance to ampicillin were present in fewer copies after 24 hours, likely due to the loss of ampicillin over time. In all but the lowest copy number plasmid, high titers of FFA were observed. The highest alcohol titers were achieved when MAACR was expressed on a low copy vector, independent of the number of copies of BTE. Error bars represent standard deviation of biological triplicate shake flask cultures.

FIG. 6B depicts the titer of fatty alcohol produced as a function of time. "Media" data points show the titer of fatty alcohol in media without a dodecane overlayer. "Media+scraping" data points show the titer of fatty alcohol in the media without a dodecane overlayer in addition to the fatty alcohol scraped from deposits on the bioreactor wall. "OL" data points refer to the titer of fatty alcohol in fermentations conducted in the presence of a dodecane overlayer. FIG. 6C depicts the relative quantity of metabolic products, as percentage of fed carbon, showing large percentages of metabolized carbon going to $CO_2$, acetate, biomass, and fatty alcohols. FIG. 6D depicts the off-gas [$CO_2$] and suggests that a metabolic steady state is achieved ~30 h post induction. FIG. 6E depicts the percent of fatty alcohol species in the media of *E. coli* cultured with (Media+Dodecane OL) and without (Media) a dodecane overlayer and shows that co-culturing with a dodecane overlayer increases the amount of fatty alcohol found outside the cell.

DETAILED DESCRIPTION OF THE INVENTION

Figure 1A:
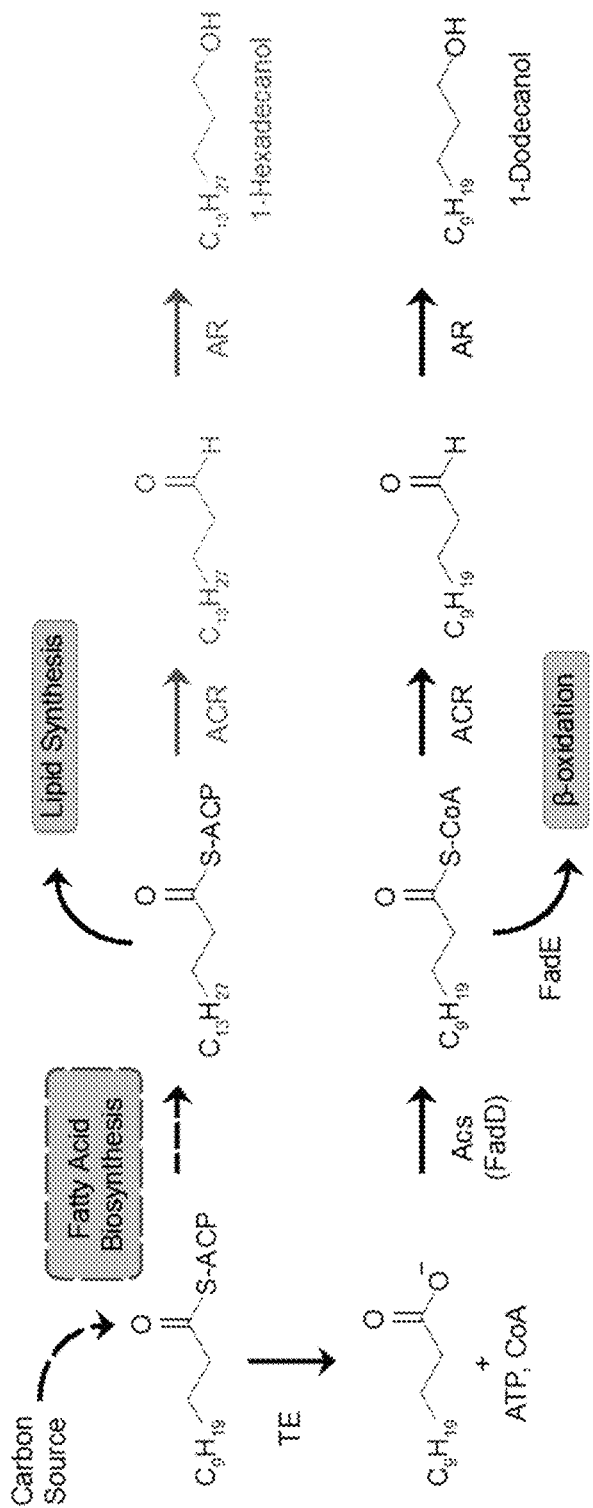
FIG. 1A depicts a schematic of metabolic pathways that lead to fatty alcohols. Fatty acid biosynthesis generates acyl-acyl-carrier proteins (acyl-ACP) that are the substrates for lipid synthesis, thioesterases (TE) and acyl-CoA reductases (ACR). The fatty aldehydes produced by ACR can be reduced to primary alcohols by aldehyde reductases (AR). Expression of ACR/AR pairs leads to the formation of fatty alcohols that match the predominant acyl-ACP species (i.e., 16 carbons in E. coli). Alternatively, medium chain length alcohols can be produced by using an acyl-ACP thioesterase to produce a smaller fatty acid. Free fatty acids are then converted to acyl-CoA thioesters, by acyl-CoA synthetases (AS) and subsequently reduced by ACR to aldehydes and by AR to alcohols.
Figure 1B:
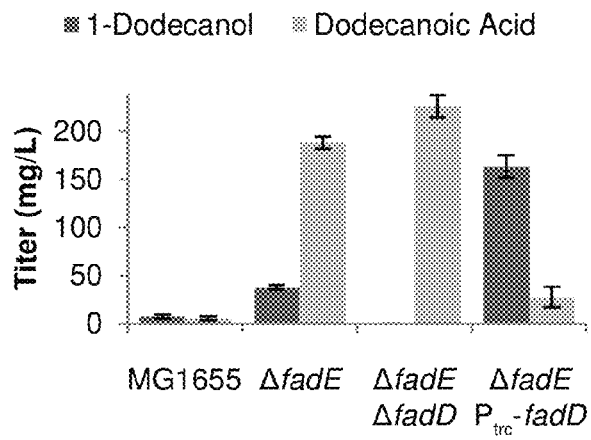
FIGS. 1B-C show conversion of exogenously fed dodecanoic acid to 1-dodecanol (FIG. 1B) or 1-hexadecanol (FIG. 1C) by E. coli strains harboring ptrc99a-MAACR (MAACR contains both ACR and AR activities) in control, ΔfadE, ΔfadE/ΔfadD, or ΔfadE/P$_{trc}$-fadD genetic backgrounds.
Figure 1C:
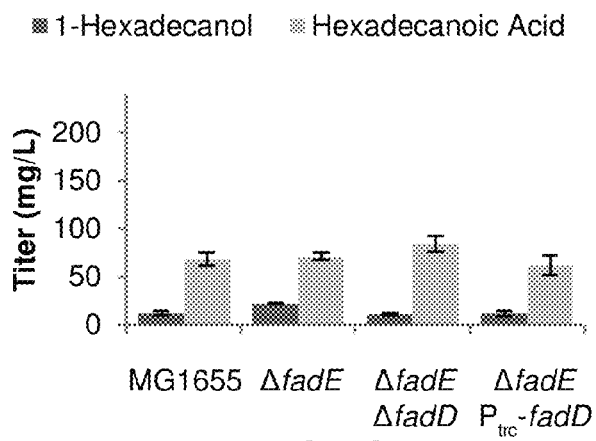
Figure 1D:
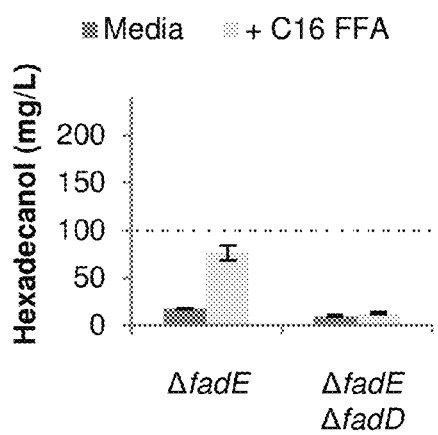
FIG. 1D shows conversion of exogenously fed hexadecanoic acid to hexadecanol by E. coli strains harboring ptrc99a-MAACR in ΔfadE and ΔfadE/ΔfadD genetic backgrounds. Cultures of ΔfadE pMAACR supplemented with 100 mg/L hexadecanoic acid generated 76 mg/L of hexadecanol after 24 hours, whereas cultures of ΔfadE ΔfadD pMAACR generated 10-15 mg/L of hexadecanol, equivalent to unsupplemented ΔfadE pMAACR cultures.

The following abbreviations are used herein:
ACL—acyl CoA ligase;
ACP—acyl carrier protein;
ACR—acyl CoA reductase;
BTE—California Bay Laurel (*Umbellularia californica*) Thioesterase;
Cx—fatty acid or alcohol species containing x number of carbon atoms;
CDW—Cell dry weight;
CoA—Coenzyme A;
$DO_2$—Dissolved oxygen;
EC—Enzyme Commission
ECGSC—*Escherichia coli* Genetic Stock Center—Yale University;
FAME—Fatty Acid Methyl Ester;
GC/MS—Gas Chromatography Mass Spectrometry;
LB—Lysogeny Broth;
MAACR—*Marinobacter aquaeolei* VT8 ACR
PBS—Phosphate Buffered Saline; and
PCR—Polymerase Chain Reaction.

The present invention is directed to cells and methods for producing fatty alcohols having a defined monomeric composition at a high yield from an unrelated carbon source. The invention involves genetically modifying cells to feed carbon substrates having a defined carbon length into the early steps of the β-oxidation pathway and then diverting the substrates toward fatty alcohol synthesis by shutting down or reducing the efficiency of downstream steps in the β-oxidation pathway while increasing acyl-CoA reductase and aldehyde reductase activity.

One aspect of the invention is a recombinant (i.e., genetically modified) cell that is capable of producing fatty alcohols. The cell of the present invention may be any type of cell that is capable of producing fatty alcohols, either naturally or by virtue of genetic engineering. Examples of suitable cells include but are not limited to bacterial cells, yeast cells, fungal cells, insect cells, mammalian cells, and plant cells. Examples of suitable bacterial cells include gram-positive bacteria such as strains of *Bacillus*, (e.g., *B. brevis* or *B. subtilis*), *Pseudomonas*, or *Streptomyces*, or gram-negative bacteria, such as strains of *E. coli* or *Aeromonas hydrophila*. Particularly desirable cells for expression in this regard include bacteria that do not produce lipopolysaccharide and are endotoxin free. Examples of suitable yeast cells include strains of *Saccharomyces*, such as *S. cerevisiae*; *Schizosaccharomyces*; *Kluyveromyces*; *Pichia*, such as *P. pastoris* or *P. methlanolica*; *Hansenula*, such as H. *Polymorpha*; *Yarrowia*; or *Candida*. Examples of suitable filamentous fungal cells include strains of *Aspergillus*, e.g., *A. oryzae*, *A. niger*, or *A. nidulans*; *Fusarium* or *Trichoderma*. Examples of suitable insect cells include a *Lepidoptora* cell line, such as *Spodoptera frugiperda* (Sf9 or Sf21) or *Trichoplusioa ni* cells ("HIGH FIVE"-brand insect cells, Invitrogen, Carlsbad, Calif.) (U.S. Pat. No. 5,077,214). Examples of suitable mammalian cells include Chinese hamster ovary (CHO) cell lines, e.g., CHO-K1 (ATCC CCL-61); green monkey cell lines, e.g., COS-1 (ATCC CRL-1650) and COS-7 (ATCC CRL-1651); mouse cells, e.g., NS/O; baby hamster kidney (BHK) cell lines, e.g., ATCC CRL-1632 or ATCC CCL-10; and human cells, e.g., HEK 293 (ATCC CRL-1573). Examples of suitable plant cells include those of oilseed crops, including rapeseed, canola, sunflower, soybean, cottonseed, and safflower plants, and cells from other plants such as *Arabidopsis thaliana*. Some of the foregoing cell types are capable of naturally producing fatty alcohols, such as certain microorganisms. The other cell types are capable of producing fatty alcohols through genetic modification. Preferred cells are microorganisms, such as yeast and bacteria. A preferred bacterium is *E. coli*.

The recombinant cell of the invention preferably has one or more genes in the β-oxidation pathway functionally deleted to inhibit consumption of substrates for fatty alcohol production. "Functional deletion" or its grammatical equivalents refers to any modification to a microorganism that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. In some versions of the invention, functionally deleting a gene product or homolog thereof means that the gene is mutated to an extent that a corresponding gene product is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, or other variations to a coding sequence or a sequence controlling the transcription or translation of a coding sequence; placing a coding sequence under the control of a less active promoter; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, $4^{th}$ ed., Cold Spring Harbor Laboratory Press (2012) and Sambrook et al., *Molecular Cloning: A Laboratory Manual*, $3^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small-molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of the gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding cell. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding cell. As used herein, "corresponding cell" refers to a cell of the same species having the same or substantially same genetic and proteomic composition as a cell of the invention, with the exception of genetic and proteomic differences resulting from the manipulations described herein for the cells of the invention.

In some versions of the invention, a gene product of an acyl-CoA dehydrogenase gene in the recombinant cell is functionally deleted. Acyl-CoA dehydrogenases include enzymes classified under EC number 1.3.99.-. Acyl-CoA dehydrogenases catalyze the initial step in each cycle of fatty acid β-oxidation by introducing a trans double-bond between C2 and C3 of the acyl-CoA thioester substrate. An example of an acyl-CoA dehydrogenase gene in bacteria includes fadE (SEQ ID NO:1 (coding sequence) and SEQ ID NO:2 (protein); GenBank NC_000913.2 at 240859-243303 (complement)). An example of an acyl-CoA dehydrogenase gene in yeast is POX1 (FOX1) (GenBank Z72727.1 at 654-2900). An example of an acyl-CoA dehydrogenase gene in filamentous fungal cells is scdA (GenBank AN0824.2). Examples of acyl-CoA dehydrogenase genes in mammalian cells include the various ACAD genes (e.g., KEGG 33, 35, 37, 28976, 80724, 84129, etc.). An example of an acyl-CoA dehydrogenase gene in plants includes MFP2 (KEGG AT3G06860). Homologs of the above-mentioned acyl-CoA dehydrogenase genes suitable for use in the present invention can be determined by many known methods, one of which is described below. In preferred versions of the invention, the acyl-CoA dehydrogenase gene product that is functionally deleted has a sequence comprising SEQ ID NO:2 or a sequence homologous thereto, such as sequences 70%, 75%, 80%, 85%, 90%, 95%, 97%, 98%, 99%, or more identical thereto.

In some versions of the invention, a gene product of an enoyl-CoA hydratase gene in the recombinant cell is functionally deleted. Enoyl-CoA hydratases include enzymes classified under Enzyme Commission (EC) number 4.2.1.17. Enoyl-CoA hydratases catalyze the conversion of trans-2 (or 3)-enoyl-CoA to (3S)-3-hydroxyacyl-CoA in the β-oxidation pathway. The term "enoyl-CoA hydratase" used herein without an indication of stereospecificity refers to the enzymes under EC 4.2.1.17 that produce (3S)-3-hydroxyacyl-CoA. These enzymes are distinct from the enzymes that produce (3R)-3-hydroxyacyl-CoA and are designated under EC 4.2.1.119, which are referred to herein as "R-specific enoyl-CoA hydratases." Examples of enoyl-CoA hydratase genes in bacteria include fadB (SEQ ID NO:3 (coding sequence) and SEQ ID NO:4 (protein); GenBank NC_000913.2 at 4026805-4028994 (complement)) and fadJ (SEQ ID NO:5 (coding sequence) and SEQ ID NO:6 (protein); GenBank NC_000913.2 at 2455037-2457181 (complement)). Examples of enoyl-CoA hydratase genes in yeast include FOX2 (GenBank NC_001143 at 454352-457054 (complement)) or the enzyme encoded by Kyoto Encyclopedia of Genes and Genomes (KEGG) (www.genome.jp/kegg) entry number NCU06488. An example of enoyl-CoA hydratase genes in filamentous fungal cells includes the enzyme encoded by KEGG entry number AN5916.2. An example of an enoyl-CoA hydratase gene in insect cells is Mfe2 (GenBank NM_132881.2). Examples of enoyl-CoA hydratase genes in mammalian cells include ECHS1 (GenBank NM_004092.3), EHHADH (GenBank NM_001966.3), and HADHA (GenBank. NM_000182.4). Examples of enoyl-CoA hydratase genes in plants include MFP2 (GenBank NM_111566.3) and AIM1 (GenBank NM_119045.4). Homologs of the above-mentioned enoyl-CoA hydratase genes suitable for use in the present invention can be determined by many known methods, one of which is described below. In preferred versions of the invention, the enoyl-CoA hydratase gene product that is functionally deleted has a sequence comprising SEQ ID NO:4 or a sequence homologous thereto, SEQ ID NO:6 or a sequence homologous thereto, or SEQ ID NO:4 and SEQ ID NO:6 or sequences homologous thereto, such as sequences 70%, 75%, 80%, 85%, 90%, 95%, 97%, 98%, 99%, or more identical thereto.

In some versions of the invention, a gene product of a 3-hydroxyacyl-CoA dehydrogenase gene in the recombinant cell is functionally deleted. 3-Hydroxyacyl-CoA dehydrogenases include enzymes classified under EC number 1.1.1.35. 3-Hydroxyacyl-CoA dehydrogenases catalyze the conversion of (3S)-3-hydroxyacyl-CoA to 3-ketoacyl CoA in the β-oxidation pathway. Examples of 3-hydroxyacyl-CoA dehydrogenase genes in bacteria include fadB (SEQ ID NO:3 (coding sequence) and SEQ ID NO:4 (protein); GenBank NC_000913.2 at 4026805-4028994 (complement)) and fadJ (SEQ ID NO:5 (coding sequence) and SEQ ID NO:6 (protein); GenBank NC_000913.2 at 2455037-2457181 (complement)). An example of a 3-hydroxyacyl-CoA dehydrogenase gene in yeast includes FOX2 (GenBank NC_001143 at 454352-457054 (complement)). An example of a 3-hydroxyacyl-CoA dehydrogenase gene in filamentous fungal cells includes the enzyme encoded by KEGG entry number AN7238.2. An example of a 3-hydroxyacyl-CoA dehydrogenase gene in insect cells is Mfe2 (GenBank NM_132881.2). Examples of 3-hydroxyacyl-CoA dehydrogenase genes in mammalian cells include EHHADH (GenBank NM_001966.3), HSD17B10 (GenBank NG_008153.1), HADH (GenBank NM_001184705.2), and HSD17B4 (GenBank NG_008182.1). Examples of 3-hydroxyacyl-CoA dehydrogenase genes in plants include MFP2 (GenBank NM_111566.3) and AIM1 (GenBank NM_119045.4). Homologs of the above-mentioned 3-hydroxyacyl-CoA dehydrogenase genes suitable for use in the present invention can be determined by many known methods, one of which is described below. In preferred versions of the invention, the 3-hydroxyacyl-CoA dehydrogenase gene product that is functionally deleted has a sequence comprising SEQ ID NO:4 or a sequence homologous thereto, SEQ ID NO:6 or a sequence homologous thereto, or SEQ ID NO:4 and SEQ ID NO:6 or sequences homologous thereto, such as sequences 70%, 75%, 80%, 85%, 90%, 95%, 97%, 98%, 99%, or more identical thereto.

In some versions of the invention, a gene product of a 3-ketoacyl-CoA thiolase gene in the recombinant cell is functionally deleted. 3-Ketoacyl-CoA thiolases include enzymes classified under EC number 2.3.1.16. 3-Ketoacyl-CoA thiolases catalyze the conversion of 3-ketoacyl CoA to acetyl-CoA and a shortened acyl-CoA species in the β-oxidation pathway. Examples of 3-ketoacyl-CoA thiolase genes in bacteria include fadA (SEQ ID NO:7 (coding sequence) and SEQ ID NO:8 (protein); GenBank NC_000913.2 at 4025632-4026795 (complement)) and fadI (SEQ ID NO:9 (coding sequence) and SEQ ID NO:10 (protein); GenBank NC_000913.2 at 2457181-2458491 (complement)). An example of a 3-ketoacyl-CoA thiolase gene in yeast includes FOX3 (GenBank NM_001179508.1). Examples of 3-ketoacyl-CoA thiolase genes in filamentous fungal cells include the enzymes encoded by KEGG entry numbers AN5646.2 and AN5698.2. An example of a 3-ketoacyl-CoA thiolase gene in insect cells is gene yip2 (GenBank NM_078804.3). Examples of 3-ketoacyl-CoA thiolase genes in mammalian cells include ACAA1 (GenBank NR_024024.1), ACAA2 (GenBank NM_006111.2), and HADHB (GenBank NG_007294.1). Examples of 3-ketoacyl-CoA thiolase genes in plants include PKT4 (GenBank NM_100351.4), PKT3 (GenBank NM_128874.3), and PKT2 (GenBank NM_180826.3). Homologs of the above-mentioned 3-ketoacyl-CoA thiolase genes suitable for use in the present invention can be determined by many known methods, one of which is described below. In preferred versions of the invention, 3-ketoacyl-CoA thiolase gene product that is functionally deleted has a sequence comprising SEQ ID NO:8 or a sequence homologous thereto, SEQ ID NO:10 or a sequence homologous thereto, or SEQ ID NO:8 and SEQ ID NO:10 or sequences homologous thereto, such as sequences 70%, 75%, 80%, 85%, 90%, 95%, 97%, 98%, 99%, or more identical thereto.

Production of fatty alcohols can be enhanced when the β-oxidation pathway is maximally shut down at a particular step downstream of the acyl-CoA synthetase step. When a cell has more than one enzyme catalyzing a step in the β-oxidation pathway, i.e., enoyl-CoA hydration, (3S)-hydroxyacyl-CoA dehydrogenation, or ketoacyl-CoA thiolation, it is preferred that more than one enzyme catalyzing that step is functionally deleted. It is more preferred that all enzymes catalyzing that step are functionally deleted. In the case of bacteria, for example, it is preferred that products of both fadA and fadI, both fadB, and fadJ, or all of fadA, fadB, fadI, and fadJ are functionally deleted.

In a preferred bacterial cell of the invention, the cell comprises a functional deletion of the fadE gene product. Other versions comprise a functional deletion of products of fadA; fadI; fadB; fadJ; fadA and fadI; fadB and fadJ; or fadA, fadB, fadI, and fadJ. Other versions comprise a functional deletion of products of fadE and fadA; fadE and fadI; fadE and fadB; fadE and fadJ; fadE, fadA, and fadI; fadE, fadB, and fadJ; or fadE, fadA, fadB, fadI, and fadJ. Other versions comprise a functional deletion of products of any combination of fadE, fadA, fadB, fadI, and fadJ.

In various versions of the invention, the cell is genetically modified to comprise a recombinant gene. In most cases, the recombinant gene is configured to be expressed or overexpressed in the cell. If a cell endogenously comprises a particular gene, the gene may be modified to exchange or optimize promoters, exchange or optimize enhancers, or exchange or optimize any other genetic element to result in increased expression of the gene. Alternatively, one or more additional copies of the gene or coding sequence thereof may be introduced to the cell for enhanced expression of the gene product. If a cell does not endogenously comprise a particular gene, the gene or coding sequence thereof may be introduced to the cell for expression of the gene product. The gene or coding sequence may be incorporated into the genome of the cell or may be contained on an extra-chromosomal plasmid. The gene or coding sequence may be introduced to the cell individually or may be included in an operon. Techniques for genetic manipulation are described in further detail below.

In some versions of the invention, the cells are genetically modified to express or overexpress a recombinant acyl-CoA synthetase gene. "Acyl-CoA synthetase gene" refers to a polynucleotide that encodes or expresses an acyl-CoA synthetase (acyl-CoA ligase) or a gene product having acyl-CoA synthetase (acyl-CoA ligase) activity. Acyl-CoA synthetase activity includes the activity characterized by the enzymes classified under EC 6.2.1.-, such as EC 6.2.1.3. An example of acyl-CoA synthetase activity includes the conversion of free fatty acids, coenzyme A, and ATP to fatty acyl CoAs plus AMP (Black et al. 1992, J. Biol. Chem. 267:25513-25520). Examples of suitable acyl-CoA synthetase genes include fadD (SEQ ID NO:11 (coding sequence), which encodes SEQ ID NO:12 (protein); GenBank NC_000913.2 at 1886085-1887770 (complement)) from E. coli (Black et al. 1992, J. Biol. Chem. 267:25513-25520), alkK from Pseudomonas oleovorans (GenBank AJ245436.1 at 13182-14822) (van Beilen et al. 1992, Molecular Microbiology 6:3121-3136), Pfacs1 from Plasmodium falciparum (GenBank AF007828.2) (Matesanz et al. 1999, J. Mol. Biol. 291:59-70), and PP_0763 (KEGG) from P. putida (SEQ ID NO:13 (coding sequence) and SEQ ID NO:14 (protein)), described herein. Methods and materials for identification of other suitable acyl-CoA synthetases are described in U.S. Pat. No. 7,786,355. Homologs of the above-mentioned acyl-CoA synthetase genes suitable for use in the present invention can be determined by many known methods, one of which is described below. In preferred versions of the invention, the cells express or overexpress an acyl-CoA synthetase gene product that has a sequence comprising SEQ ID NO:12 or a sequence homologous thereto, such as sequences 70%, 75%, 80%, 85%, 90%, 95%, 97%, 98%, 99%, or more identical thereto.

In various versions of the invention, the recombinant acyl-CoA synthetase gene is expressed to a level greater than about 1-fold, about 1.25-fold, about 1.5-fold, about 1.75-fold, about 2-fold, about 3-fold, or about 5-fold a level of expression of a native acyl-CoA synthetase gene in a corresponding host but less than about 2,000-fold, about 1,500-fold, about 1,000-fold, about 500-fold, about 250-fold, about 100-fold, about 75-fold, or about 50-fold the level of expression of the native acyl-CoA synthetase gene in the corresponding host. Such levels are preferably generated in a host when the native acyl-CoA synthetase gene in the host is deleted. The levels of expression can be determined, for example, by comparing acyl-CoA synthetase mRNA levels in a host comprising only the recombinant acyl-CoA synthetase gene (i.e., the native (wild-type) acyl-CoA synthetase gene is deleted) with acyl-CoA synthetase mRNA levels in a corresponding host comprising only the native (wild-type) acyl-CoA synthetase gene, as performed in the examples. Other methods, such as measuring protein levels or enzyme activity are known in the art. The levels of expression described above may be determined during exponential phase of growth.

In various versions of the invention, the acyl-CoA synthetase gene is included in the cell in an amount of from about 1 to about 50 copies per copy of genomic DNA, about 1 to about 25 copies per copy of genomic DNA, about 1 to about 10 copies per copy of genomic DNA, about 1 to about 5 copies per copy of genomic DNA, or about 1 to about 2 copies per copy of genomic DNA. A method of determining an amount of copies of a gene per copy of genomic DNA is found in the examples. Other methods are known in the art. The above-mentioned copy numbers of the acyl-CoA synthetase gene may be determined during exponential phase of growth.

In some versions of the invention, the cells are genetically modified to express or overexpress a recombinant acyl-CoA reductase gene. "Acyl-CoA reductase gene" refers to a polynucleotide that encodes or expresses an acyl-CoA reductase or a gene product having acyl-CoA reductase activity. Acyl-CoA reductase activity includes the activity characterized by the enzymes classified under EC 1.2.1.—such as EC 1.2.1.50, EC 1.2.1.80, and EC 1.2.1.84. Some acyl-CoA reductases have acyl-CoA reductase activity, and others have both acyl-CoA reductase activity and aldehyde reductase activity. Particularly suitable acyl-CoA reductases include those that have both acyl-CoA reductase activity and aldehyde reductase activity. Such acyl-CoA reductases may catalyze the reaction of a fatty acyl-CoA, NADPH, and a proton to an acyl primary alcohol, NADP+, and CoA. In some versions of the invention, acyl-CoA reductases that use NADH are preferable to those that use NADPH, due to the abundance of NADH in cells such as E. coli. Examples of suitable acyl-CoA reductase genes include FAR2 from H. sapiens (GenBank NP_060569.3), FAR2 from P. troglodytes (GenBank XP_001141453.1), FAR2 from M. mulatta (Gen- Bank XP_001105259.1), FAR2 from *C. lupus* (GenBank XP_534853.1), FAR2 from *B. Taurus* (GenBank NP_001069490.1), Far2 from *M. musculus* (GenBank NP_848912.1), Far2 from *R. norvegicus* (GenBank XP_575726.2), FAR2 from *G. gallus* (GenBank XP_417235.2), CG5065 from *D. melanogaster* (GenBank NP_001163168.1), AgaP_AGAP009690 from *A. gambiae* (GenBank XP_318748.4), fard-1 from *C. elegans* (GenBank NP_508505.1), FAR5 from *A. thaliana* (GenBank NP_190041.2), FAR4 from *A. thaliana* (GenBank NP_190040.3), FAR1 from *A. thaliana*, (GenBank NP_197642.1), FAR8 from *A. thaliana* (GenBank NP_190042.2), FAR7 from *A. thaliana*, GenBank NP_197634.1), CER4 from *A. thaliana* (GenBank NP_567936.5), Os04g0354400 from *O. sativa* (GenBank NP_001052540.1), Os04g0354600 from *O. sativa* (GenBank NP_001052541.1), Os08g0557800 from *O. sativa*, (GenBank NP_001062488.1), Os09g0567500 from *O. sativa* (GenBank NP_001063962.1), the alcohol-forming fatty acyl-CoA reductase from *Simmondsia chinensis* (GenBank Q9XGY7), the Maqu_2220 hypothetical protein from *Marinobacter aquaeolei* VT8 (GenBank NC_008740.1 at positions 2484020-2485561 (complement)), and the Maqu_2507 short chain dehydrogenase from *Marinobacter aquaeolei* VT8 (GenBank NC_008740.1 at positions 2803788-2805773 (complement). Other examples of suitable acyl-CoA reductases include those described in Cheng et al. *J Biol Chem.* 2004, 279(36):37798-807; Doan et al. *J Plant Physiol.* 2009, 166(8):787-96 (far6); Hofvander et al. *FEBS Lett.* 2011, 585(22):3538-43; Metz et al. *Plant Physiol.* 2000, 122(3):635-44; Reiser et al., *J Bacteriol.* 1997, 179(9):2969-75 (acr1); Schirmer et al. *Science,* 2010, 329(5991):559-62; Steen et al. *Nature,* 2010, 463(7280): 559-62; Tan et al. *Metab Eng.* 2011, 13(2):169-76; Teerawanichpan et al. *Lipids.* 2010, 45(3):263-73; Teerawanichpan et al. *Insect Biochem Mol Biol.* 2010, 40(9):641-9; Wahlen et al. *Appl Environ Microbiol.* 2009, 75(9):2758-64; Willis et al. *Biochemistry.* 2011, 50(48):10550-8; and Zheng et al. *Microb Cell Fact.* 2012, 11:65. A particularly preferred acyl-CoA reductase is that known as MAACR from *Marinobacter aquaeolei* VT8 (SEQ ID NO:15 (coding sequence) and SEQ ID NO:16 (protein). Homologs of the above-mentioned acyl-CoA reductase genes suitable for use in the present invention can be determined by many known methods, one of which is described below. In preferred versions of the invention, the cells express or overexpress an acyl-CoA reductase gene product that has a sequence comprising SEQ ID NO:16 or a sequence homologous thereto, such as sequences 70%, 75%, 80%, 85%, 90%, 95%, 97%, 98%, 99%, or more identical thereto.

In some versions of the invention, the cells are genetically modified to express or overexpress an aldehyde reductase gene. "Aldehyde reductase gene" refers to a polynucleotide that encodes or expresses an aldehyde reductase or a gene product having aldehyde reductase activity. Aldehyde reductase activity includes the activity characterized by the enzymes classified under EC 1.1.1.192. Aldehyde reductase activity includes the reduction of fatty aldehydes to fatty alcohols. Aldehyde reductases are also referred to as long-chain-alcohol dehydrogenases, fatty alcohol oxidoreductases, and long-chain alkyl alcohol dehydrogenases. Examples of suitable acyl-CoA reductase genes include those described in Van Ophem et al. *Eur. J. Biochem.* 1992, 206(2): 511-518; Lee, T. C. *J. Biol. Chem.* 1979, 254(8): 2892-2896; Ueda et al. *Methods Enzymol.* 1990, 188:171-175; Yamada et al. 1980, *Arch. Microbiol.* 128(2):145-51; Ribas de Pouplana et al. *Biochem. J.* 1991, 276:433-438; Nagashima et al. *J. Ferment.* 1996, *Bioeng.* 82:328-333; Eklund et al. *J. Mol. Biol.* 1976, 102:27-59; Luesch et al. *J. Org. Chem.* 2003, 68:83-91; and Liu et al. *Microbiology* 2009, 155:2078-2085. Homologs of the above-mentioned aldehyde reductase genes suitable for use in the present invention can be determined by many known methods, one of which is described below. Cells are preferably genetically modified to express or overexpress a recombinant gene encoding an aldehyde reductase that does not have acyl-CoA reductase activity in combination with recombinant gene encoding the acyl-CoA reductase that does not have aldehyde reductase activity.

In some versions of the invention, the acyl-CoA reductase gene or the aldehyde reductase gene may comprise a gene encoding a polypeptide having acyl-CoA reductase activity fused to a polypeptide having aldehyde reductase activity. Such genes may be obtained by combining a gene encoding a polypeptide having acyl-CoA reductase activity with a gene encoding a polypeptide having aldehyde reductase activity in a single reading frame. In other versions of the invention, the acyl-CoA reductase gene and the aldehyde reductase gene are configured for the resulting acyl-CoA reductase and aldehyde reductase gene products to be complexed via a protein scaffold. See, e.g., Dueber et al. 2009, *Nat. Biotechnol.* 27, 753-9.

In various versions of the invention, the recombinant acyl-CoA reductase gene is included in the cell in an amount of from about 1 to about 100 copies per copy of genomic DNA, about 1 to about 50 copies per copy of genomic DNA, about 1 to about 25 copies per copy of genomic DNA, about 1 to about 10 copies per copy of genomic DNA, about 1 to about 5 copies per copy of genomic DNA, or about 1.1 to about 5 copies per copy of genomic DNA, or about 1.1 to about 3 copies per copy of genomic DNA. The above-mentioned copy numbers of the acyl-CoA reductase gene may be determined during exponential phase of growth.

In various versions of the invention, the recombinant acyl-CoA reductase gene and the recombinant acyl-CoA synthetase gene are included in the recombinant cell at a copy ratio of from about 20:1 to about 1:5, such as about 20:1, about 15:1, about 10:1, about 7.5:1, about 5:1, about 2.5:1, about 2:1, about 1:1, about 1:2, or about 1:5. In some versions of the invention, the recombinant acyl-CoA reductase gene and the recombinant acyl-CoA synthetase gene are included in the recombinant cell at a copy ratio of from about 10:1 to about 1:2, from about 7.5:1 to about 1:2, from about 5:1 to about 1:2, from about 10:1 to about 1:1, from about 7.5:1 to about 1:1, from about 5:1 to about 1:1 or from about 3:1 to about 1:1. The above-mentioned copy ratios may be determined during exponential phase of growth. In some versions, the copy number of the acyl-CoA reductase gene is greater than the copy number of the acyl-CoA synthetase gene. An exemplary ratio is about 2:1 as determined during exponential phase of growth.

In various versions of the invention, the recombinant acyl-CoA reductase gene and the recombinant acyl-CoA synthetase gene each comprises a promoter that confers a level of expression per gene copy within about +/−50% of a level of expression of the other promoter, within about +/−25% of a level of expression of the other promoter, within about +/−20% of a level of expression of the other promoter, within about +/−15% of a level of expression of the other promoter, within about +/−10% of a level of expression of the other promoter, within about +/−5% of a level of expression of the other promoter, within about +/−2.5% of a level of expression of the other promoter, or within about +/−1% of a level of expression of the other promoter. In exemplary versions, the recombinant acyl-CoA reductase gene and the recombinant acyl-CoA synthetase gene comprise promoters that confer about the same level of expression per gene copy when the copy number of the acyl-CoA reductase gene is greater than the copy number of the acyl-CoA synthetase gene, such as with a copy number ratio of about 2:1. The above-mentioned expression levels and copy numbers may be determined during exponential phase of growth.

In various versions of the invention, the recombinant acyl-CoA reductase gene and the recombinant acyl-CoA synthetase gene each comprises a promoter that confers a level of expression per gene copy within about +/−50% of a level of expression from the trc promoter when saturated with inducer, within about +/−25% of a level of expression from the trc promoter when saturated with inducer, within about +/−20% of a level of expression from the trc promoter when saturated with inducer, within about +/−15% of a level of expression from the trc promoter when saturated with inducer, within about +/−10% of a level of expression from the trc promoter when saturated with inducer, within about +/−5% of a level of expression from the trc promoter when saturated with inducer, within about +/−2.5% of a level of expression from the trc promoter when saturated with inducer, or within about +/−1% of a level of expression from the trc promoter when saturated with inducer. The above-mentioned expression levels may be determined during exponential phase of growth.

In some versions of the invention, the relative level of expression of the recombinant acyl-CoA reductase gene with respect to the level of expression of the recombinant acyl-CoA synthetase gene is the same as that obtained by providing the recombinant acyl-CoA reductase gene with respect to the recombinant acyl-CoA synthetase gene in a copy-number ratio of from about 10:1 to about 1:2, from about 7.5:1 to about 1:2, from about 5:1 to about 1:2, from about 10:1 to about 1:1, from about 7.5:1 to about 1:1, from about 5:1 to about 1:1 or from about 3:1 to about 1:1 when the recombinant acyl-CoA reductase gene and the recombinant acyl-CoA synthetase gene each comprises a promoter that confers a level of expression per gene copy within about +/−50% of a level of expression of the other promoter, within about +/−25% of a level of expression of the other promoter, within about +/−20% of a level of expression of the other promoter, within about +/−15% of a level of expression of the other promoter, within about +/−10% of a level of expression of the other promoter, within about +/−5% of a level of expression of the other promoter, within about +/−2.5% of a level of expression of the other promoter, or within about +/−1% of a level of expression of the other promoter. The relative levels of expression conferred by the promoters assume the same or equivalent strength transcriptional enhancers, or other factors affecting expression, if present. The levels of expression can be determined by determining mRNA levels, protein levels, or activity levels. The expression levels and copy numbers may be determined during exponential phase of growth.

Such a relative level of expression of the recombinant acyl-CoA reductase gene with respect to the level of expression of the recombinant acyl-CoA synthetase gene can be obtained by configuring the recombinant acyl-CoA reductase and recombinant acyl-CoA synthetase genes to have approximately the same level of expression per copy number while providing more copies of the recombinant acyl-CoA reductase gene than the recombinant acyl-CoA synthetase gene. Such a relative level of expression can also be obtained by configuring the recombinant acyl-CoA reductase gene to have a greater level of expression per copy number than the recombinant acyl-CoA synthetase gene while providing the recombinant acyl-CoA reductase and recombinant acyl-CoA synthetase genes at approximately the same number of copies. Other configurations are acceptable, provided the appropriate relative level of expression is obtained.

To configure genes to have approximately the same or similar expression levels per copy number, the same or similar strength promoters, transcriptional enhancers, ribosome binding sites, and/or translational enhancers can be provided on the genes. To configure a first gene to have a greater level of expression per copy number than a second gene, stronger promoter, transcriptional enhancers, ribosome binding site, and/or translational enhancers can be provided on the first gene with respect to the second gene. To configure a first gene to approximately the same copy number as a second gene, both genes can be provided on the same chromosome, on the same plasmid, or on different plasmids having the same origin of replication or origins of replication having similar strengths. To configure a first gene to have a greater copy number than a second gene, the first gene can be provided on a plasmid or DNA construct with a more active origin of replication than the second gene. These and other ways of obtaining the relative levels of expression described above are known in the art, some of which are exemplified below.

In some versions of the invention, the cells are genetically modified to express or overexpress a recombinant thioesterase gene. Thioesterases include enzymes classified into EC 3.1.2.1 through EC 3.1.2.27 based on their activities on different substrates, with many remaining unclassified (EC 3.1.2.-). Thioesterases hydrolyze thioester bonds between acyl chains and CoA or between acyl chains and ACP. These enzymes terminate fatty acid synthesis by removing the CoA or ACP from the acyl chain.

Expression or overexpression of a recombinant thioesterase gene can be used to engineer to produce a homogeneous population of fatty acid products to feed into the fatty alcohol synthesis pathway, and thereby produce fatty alcohols having a defined side chain length. To engineer a cell for the production of a homogeneous population of fatty acid products, one or more thioesterases with a specificity for a particular carbon chain length or chain lengths can be expressed. For example, any of the thioesterases shown in the following table can be expressed individually or in combination to increase production of fatty acid products having specific chain lengths.

Thioesterases.

| Gen Bank Accession Number | Source Organism | Gene | Preferential product produced |
|---|---|---|---|
| AAC73596 | E. coli | tesA without leader sequence | $C_8$-$C_{18}$ |
| 041635; V17097; M94159 | Umbelluiaria cohfornico | fatB | $C_{12:0}$ |
| Q39513 | Cuphea hookeriana | fatB2 | $C_{8:0}$-$C_{10:0}$ |
| AAC49269 | Cuphea hookeriana | fatB3 | $C_{14:0}$-$C_{16:0}$ |
| Q39473 | Cinnamonum camphorum | fatB | $C_{14:0}$ |
| CAA85388 | Arabidopsis thaliana | fatB[M141T]* | $C_{16:1}$ |

Thioesterases.

| Gen Bank Accession Number | Source Organism | Gene | Preferential product produced |
|---|---|---|---|
| NP 189147; NP 193041 | Arabidopsis thaliana | fatA | $C_{18:1}$ |
| CAC39106 | Brodyrhilzobium japonicum | fatA | $C_{18:1}$ |
| AAC72883 | Cuphea hookeriana | fatA | $C_{18:1}$ |

*Mayer et al., BMC *Plant Biology* 7:1-11, 2007.

Other thioesterases that can be expressed or overexpressed in the cell include any of the many acyl-acyl carrier protein thioesterases from *Streptococcus pyogenes*, including any having GenBank Accession Numbers AAZ51384.1, AAX71858.1, AAT86926.1, YP_280213.1, YP_060109.1, YP_006932842.1, YP_005411534.1, AFC68003.1, AFC66139.1, YP_006071945.1, YP_600436.1, AEQ24391.1 and ABF37868.1; a palmitoyl-acyl carrier protein thioesterase from *Ricinus communis*, such as those having GenBank Accession Numbers EEF47013.1, XP_002515564.1, EEF51750.1, XP_002511148.1, and EEF36100.1; a myristoyl-acyl carrier protein thioesterase from *Ricinus communis*, such as those having GenBank Accession Numbers EEF44689.1 and XP_002517525.1; an oleoyl-acyl carrier protein thioesterase from *Ricinus communis*, such as those having GenBank Accession Numbers EEF29646.1 and XP_002532744.1; an acyl-acyl carrier protein thioesterase from *Ricinus communis*, such as that having GenBank Accession Number ABV54795.1; an acyl-acyl carrier protein thioesterase from *Jatropha curcus*, such as that described in Zhang, X. et A (201.1) *Metab. Eng.* 13, 713-722; an FabD from *Streptomyces avermitilis*, such as that having GenBank Accession Number NP_826965.1; a FadM acyl-CoA thioesterase from *E. coli*, such as that having GenBank Accession Number NP_414977.1; a TesB thioesterase II (acyl-CoA thioesterase), such as those having GenBank Accession Numbers ZP_12508749.1, EGT66607.1, ZP_03035215.1, and EDV65664.1; and a fatB-type thioesterase specific for C18:1 and C18:0 derived from *Madhuca latifolia*, such as that having the GenBank Accession Number AY835985. These and additional suitable thioesterases that can be expressed or overexpressed in the cell are described in U.S. 2011/0165637 to Pfleger et al.; Lu, X. et A (2008) *Metab. Eng.* 10, 333-339; Liu, T. et al. (2010) *Metab. Eng.* 12, 378-386; Steen, E. J. et al. (2010) *Nature* 463, 559-562; Lennen, R. M. et al. (2010) *Biotechnol. Bioeng.* 106, 193-202; Lennen, K. M. et al. (2011) *Appl. Environ. Microbial.* 77, 8114-8128; Youngquist, J. T. et al. (2012) *Biotechnol. Bioeng.* 109, 1518-1527; Jeon, E. et al. (2011) *Enzyme Microb. Technol.* 49, 44-51; Li, M. et al. (2012) *Metab. Eng.* 14, 380-387; Zhang, X. et al. (2012) *Biotechnol. Prog.* 28, 60-65; Zhang, X. et al. (2011) *Metab. Eng.* 13, 713-722; Liu, H. et al. (2012) *Microb. Cell Fact.* 11, 41; Yu, X. et al. (2011) *Proc. Natl. Acad. Sci. U.S.A.* 108, 18643-18648; Dellomonaco, C. et al. (2011) *Nature* 476, 355-359; Zhang, F. et al. (2012) *Nat. Biotechnol.* 30, 354-359; and Lennen et al, (2012) *Trends in Biotechnology* 30(12), 659-667. Yet other suitable thioesterases can be found in the ThYme: Thioester-active Enzymes database at www.enzyme.cbirc.iastate.edu. Homologs of the thioesterases described herein suitable for the use in the present invention can be determined by many known methods, one of which is described below.

In some versions, one or more endogenous thioesterases having a specificity for carbon chain lengths other than the desired product's carbon chain length can be functionally deleted. For example, C10 fatty acid products can be produced by attenuating a thioesterase specific for C18 (for example, accession numbers AAC73596 and POADA1), and expressing a thioesterase specific for C10 (for example, accession number Q39513). This results in a relatively homogeneous population of fatty acid products that have a carbon chain length of 10. In another example, C14 fatty acid products can be produced by attenuating endogenous thioesterases that produce non-C14 fatty acids and expressing the thioesterase with accession number Q39473, which uses C14-acyl carrier protein (ACP) as a substrate. In yet another example, C12 fatty acid products can be produced by expressing thioesterases that use C12-ACP as a substrate (for example, accession number Q41635) and attenuating thioesterases that produce non-C12 fatty acids.

In a preferred version of the invention, the cell comprises a gene expressing a thioesterase specific for medium chain acyl thioesters, such as a plant thioesterase specific for medium chain acyl thioesters. A particularly preferred version of the invention comprises a gene expressing a codon-optimized thioesterase derived from California Bay Laurel (*Umbellularia californica*) thioesterase (BTE) having the following a nucleic acid coding sequence of SEQ ID NO:17 and amino acid sequence of SEQ ID NO:18. Expression of BTE in the cell generates fatty acid substrates in the cell suitable for production of medium chain length fatty alcohols. Cells in preferred versions of the invention express or overexpress a gene product having a sequence comprising SEQ ID NO:18 or a sequence homologous thereto, such as sequences 70%, 75%, 80%, 85%, 90%, 95%, 97%, 98%, 99%, or more identical thereto.

Fatty alcohols can be produced with the cells described herein by culturing the cells in the presence of a carbon source. The carbon source preferably includes a carbohydrate or non-lipid based carbon source, such as a fermentable sugar, a short-chain organic acid, an amino acid, or other organic molecules. Examples of suitable fermentable sugars include adonitol, arabinose, arabitol, ascorbic acid, chitin, cellubiose, dulcitol, erythrulose, fructose, fucose, galactose, glucose, gluconate, inositol, lactose, lactulose, lyxose, maltitol, maltose, maltotriose, mannitol, mannose, melezitose, melibiose, palatinose, pentaerythritol, raffinose, rhamnose, ribose, sorbitol, sorbose, starch, sucrose, trehalose, xylitol, xylose, and hydrates thereof. Examples of short-chain organic acids include acetate, propionate, lactate, pyruvate, levulinate, and succinate. Examples of amino acids include histidine, alanine, isoleucine, arginine, leucine, asparagine, lysine, aspartic acid, methionine, cysteine, phenylalanine, glutamic acid, threonine, glutamine, tryptophan, glycine, valine, ornithine, proline, serine, and tyrosine.

The carbon sources may also include an exogenous supply of fatty acids in the medium. However, in the certain versions of the invention, the culturing is performed in a medium substantially devoid of fatty acids or fatty acid sources, such as fatty acid-containing lipids, dissolved in the medium. In various versions of the invention, the growth medium preferably includes no more than about 1 g $L^{-1}$ exogenous free fatty acid or salt thereof, no more than about 0.5 g $L^{-1}$ exogenous free fatty acid or salt thereof, no more than about 0.25 g $L^{-1}$ exogenous free fatty acid or salt thereof, no more than about 0.1 g $L^{-1}$ exogenous free fatty acid or salt thereof, no more than about 0.05 g $L^{-1}$ exogenous free fatty acid or salt thereof, no more than about 0.01 g $L^{-1}$ exogenous free fatty acid or salt thereof, no more than about 0.005 g L$^{-1}$ exogenous free fatty acid or salt thereof, or no more than about 0.001 g L$^{-1}$ exogenous free fatty acid or salt thereof dissolved therein.

The carbon source is preferably added to the cells in a fed-batch manner. The carbon source can be added to the cells in a continuous manner or in multiple, discrete additions.

In various versions of the invention, the culturing is performed at least until the cell reaches a titer of fatty alcohol of at least about 0.5 g/L, about 0.75 g/L, about 1 g/L, about 1.25 g/L, about 1.5 g/L, or about 1.6 g/L or more.

The culture is preferably performed with a mixture of aqueous fermentation broth and organic solvent, which ultimately forms a solvent overlayer. The organic solvent is preferably one in which the generated fatty alcohol is readily soluble, readily phase-separates from water, and is non-toxic to the producing microorganism. The organic solvent may comprise a mixture of various organics or a substantially pure solution of a single type of organic. The organic solvent preferably comprises alkanes. In some versions of the invention, the alkanes are medium chain alkanes. A suitable medium chain alkane is dodecane.

The cells of the invention may be genetically altered to functionally delete, express, or overexpress homologs of any of the specific genes or gene products explicitly described herein. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or gene product (amino acid) sequences of any known gene, including the genes or gene products described herein, can be determined by searching any sequence databases known the art using the gene name or accession number as a search term. Common sequence databases include GenBank (www.ncbi.nlm.nih.gov/genbank), ExPASy (www.expasy.org), KEGG (www.genome.jp/kegg), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to the genes or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance.

For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Accession numbers: The accession numbers throughout this description are derived from the NCBI database (National Center for Biotechnology Information, i.e., "Gen-Bank"), maintained by the National Institute of Health, USA, or the KEGG (Kyoto Encyclopedia of Genes and Genomics) database, maintained by the Kyoto Encyclopedia of Genes and Genomics and sponsored in part by the University of Tokyo.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule and a particular cell, "endogenous" refers to a nucleic acid sequence or polypeptide that is in the cell and was not introduced into the cell using recombinant engineering techniques. For example, an endogenous gene is a gene that was present in a cell when the cell was originally isolated from nature.

Exogenous: As used herein with reference to a nucleic acid molecule or polypeptide in a particular cell, "exogenous" refers to any nucleic acid molecule or polypeptide that does not originate from that particular cell as found in nature. Thus, a non-naturally-occurring nucleic acid molecule or protein is considered to be exogenous to a cell once introduced into the cell. A nucleic acid molecule or protein that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a cell as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

Medium chain: When used with reference to medium chain acyl groups refers to a carbon chain length of from 7 to 18 carbons, and such as a carbon chain length of from 7 to 11 carbons.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the cell. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

Recombinant: A recombinant nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially manipulated but contain the same regulatory sequences and coding regions that are found in the organism from which the nucleic acid was isolated, such as an introduced additional copy of a nucleic acid molecule naturally present in the organism. A recombinant cell or microorganism is one that contains an exogenous nucleic acid molecule, such as a recombinant nucleic acid molecule.

Recombinant cell: A cell that comprises a recombinant nucleic acid.

Vector or expression vector: An entity comprising a nucleic acid molecule that is capable of introducing the nucleic acid, or being introduced with the nucleic acid, into a cell for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

Exogenous nucleic acids encoding enzymes involved in a metabolic pathway for producing fatty alcohols can be introduced stably or transiently into a cell using techniques well known in the art, including electroporation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to neomycin, tetracycline, chloramphenicol, or kanamycin, genes that complement auxotrophic deficiencies, and the like. (See below for more detail.)

Various embodiments of the invention use an expression vector that includes a heterologous nucleic acid encoding a protein involved in a metabolic or biosynthetic pathway. Suitable expression vectors include, but are not limited to viral vectors, such as baculovirus vectors or those based on vaccinia virus, polio virus, adenovirus, adeno-associated virus, SV40, herpes simplex virus, and the like; phage vectors, such as bacteriophage vectors; plasmids; phagemids; cosmids; fosmids; bacterial artificial chromosomes; Pl-based artificial chromosomes; yeast plasmids; yeast artificial chromosomes; and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In alternative embodiments, the selectable marker gene is one that encodes dihydrofolate reductase or confers neomycin resistance (for use in eukaryotic cell culture), or one that confers tetracycline or ampicillin resistance (for use in a prokaryotic cell, such as E. coli).

The coding sequence in the expression vector is operably linked to an appropriate expression control sequence (promoters, enhancers, and the like) to direct synthesis of the encoded gene product. Such promoters can be derived from microbial or viral sources, including CMV and SV40. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Suitable promoters for use in prokaryotic cells include but are not limited to: promoters capable of recognizing the T4, T3, Sp6, and T7 polymerases; the $P_R$ and $P_L$ promoters of bacteriophage lambda; the trp, recA, heat shock, and lacZ promoters of *E. coli*; the alpha-amylase and the sigma-specific promoters of *B. subtilis*; the promoters of the bacteriophages of *Bacillus; Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, 3$^{rd}$ ed., Cold Spring Harbor Laboratory Press (2001).

Non-limiting examples of suitable promoters for use within a eukaryotic cell are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); the yeast gal4 gene promoter (Johnston et al. (1982) *PNAS* (USA) 79:6971; Silver et al. (1984) *PNAS* (USA) 81:5951); and the IgG promoter (Orlandi et al. (1989) *PNAS* (USA) 86:3833).

Coding sequences can be operably linked to an inducible promoter. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-I promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

Alternatively, a coding sequence can be operably linked to a repressible promoter. Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, Calif.); and variants thereof.

In some versions, the cell is genetically modified with a heterologous nucleic acid encoding a biosynthetic pathway gene product that is operably linked to a constitutive promoter. Suitable constitutive promoters are known in the art and include constitutive adenovirus major late promoter, a constitutive MPSV promoter, and a constitutive CMV promoter.

The relative strengths of the promoters described herein are well-known in the art.

In some versions, the cell is genetically modified with an exogenous nucleic acid encoding a single protein. In other embodiments, a modified cell is one that is genetically modified with exogenous nucleic acids encoding two or more proteins. Where the cell is genetically modified to express two or more proteins, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the coding sequences in the single expression vector.

When the cell is genetically modified with heterologous nucleic acids encoding two or more proteins, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding enzymes desired to be expressed in a cell may be codon-optimized for that particular type of cell. Codon optimization can be performed for any nucleic acid by "OPTIMUMGENE"-brand gene design system by GenScript (Piscataway, N.J.).

The introduction of a vector into a bacterial cell may be performed by protoplast transformation (Chang and Cohen (1979) *Molecular General Genetics*, 168:111-115), using competent cells (Young and Spizizen (1961) *Journal of Bacteriology*, 81:823-829; Dubnau and Davidoff-Abelson (1971) *Journal of Molecular Biology*, 56: 209-221), electroporation (Shigekawa and Dower (1988) *Biotechniques*, 6:742-751), or conjugation (Koehler and Thorne (1987) *Journal of Bacteriology*, 169:5771-5278). Commercially available vectors for expressing heterologous proteins in bacterial cells include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx, in addition to those described in the following Examples.

Methods for transforming yeast cells with heterologous DNA and producing heterologous polypeptides therefrom are disclosed by Clontech Laboratories, Inc., Palo Alto, Calif., USA (in the product protocol for the "YEASTMAKER"-brand yeast transformation system kit); Reeves et al. (1992) *FEMS Microbiology Letters* 99:193-198; Manivasakam and Schiestl (1993) *Nucleic Acids Research* 21(18): 4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) Bio/Technology 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. No. 4,837, 148; and U.S. Pat. No. 4,929,555); *Saccharomyces cerevisiae* (Hinnen et al. (1978) *Proc. Natl. Acad. Sci. USA* 75:1929 and Ito et al. (1983) *J. Bacteriol.* 153:163); *Schizosaccharomyces pombe* (Beach et al. (1981) *Nature* 300: 706); and *Yarrowia lipolytica* (Davidow et al. (1985) *Curr. Genet.* 10:380-471 and Gaillardin et al. (1985) *Curr. Genet.* 10:49).

Suitable procedures for transformation of *Aspergillus* cells are described in EP 238 023 and U.S. Pat. No. 5,679, 543. Suitable methods for transforming *Fusarium* species are described by Malardier et al., *Gene*, 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology*, 153: 163; and Hinnen et al. (1978) *PNAS USA*, 75:1920.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Summary

The following examples demonstrate an exemplary metabolic engineering strategy for producing fatty alcohols from glucose. To produce a high level of 1-dodecanol and 1-tetradecanol, an acyl-ACP thioesterase (BTE), an acyl-CoA synthetase (acyl-CoA ligase, FadD), and an acyl-CoA/aldehyde reductase (MAACR) were overexpressed in an engineered strain of *Escherichia coli*. Yields were improved by balancing expression levels of each gene, using a fed-batch cultivation strategy, and adding a solvent to the culture for extracting the product from cells. Using these strategies, a titer of over 1.6 g/L fatty alcohol with a yield of over 0.13 g fatty alcohol/g carbon source was achieved.

Materials and Methods

Bacterial Strains and Chromosome Engineering

All bacterial strains used in this study are listed in Table 1. Single gene deletions were transferred P1 transduction of phage lysates from the collection of single gene knockouts from the National BioResource Project (NIG, Japan) (Baba et al. 2006). Chromosomal integration of a BTE expression cassette (acyl-ACP thioesterase from *Umbellularia californica* under the control of the IPTG inducible $P_t$ promoter) was performed as described previously (Youngquist et al. 2012). All deletions and insertions were verified by colony PCR.

TABLE 1

Strains and plasmids

| Strain/Plasmid | Relevant Genotype/Property | Source or Reference |
|---|---|---|
| Strains | | |
| *E. coli* K-12 MG1655 | F− λ− ilvG− rfb-50 rph-1 | ECGSC |
| *E. coli* DH10B | F− mcrA Δ(mrr-hsdRMS-mcrBC) Φ80lacZΔM15 ΔlacX74 recA1 endA1 araD139 Δ(ara, leu)7697 galU galK λ− rpsL nupG | Invitrogen |
| *E. coli* DH5α | F− Φ80lacZΔM15 Δ(lacZYA-argF) U169 recA1 endA1 hsdR17 ($r_k$−, $m_k$+) phoA supE44 λ− thi⁻¹ gyrA96 relA1 | Invitrogen |
| *E. coli* DY330 | F− λ− rph-1 INV(rrnD, rrnE) ΔlacU169 gal490 pglΔ8 λcI857Δ (cro-bioA) | Yu et al., 2000 |
| *Pseudomonas putida* KT240 | Souce for PP_0763 | ATCC 47054 ™ |
| MHS01 | MG1655 ΔaraBAD ΔfadE Φ($P_{Trc}$-fadD) | This work |
| MHS02 | MG1655 ΔaraBAD ΔfadE::trcBTE | This work |
| MHS03 | MG1655 ΔaraBAD ΔfadE::trcBTE Φ($P_{Trc}$-fadD) | This work |
| MHS04 | MG1655 ΔaraBAD ΔfadR ΔfadD | This work |
| DE | MG1655 ΔaraBAD ΔfadE ΔfadD | This work |
| E | MG1655 ΔaraBAD ΔfadE | Agnew et al., 2012 |
| RL08 | MG1655 ΔaraBAD ΔfadD | Lennen et al., 2010 |
| TY19 | MG1655 ΔaraBAD ΔfadR ΔfadE::trcBTE | This work |
| TY27 | MG1655 ΔaraBAD ΔfadD ΔfadE::trcBTE | This work |
| TY30 | MG1655 ΔaraBAD ΔfadE::trcBTE ΔfadAB::trcBTE Φ($P_{Trc}$-fadD) | This work |
| TY31 | MG1655 ΔaraBAD ΔfadE::trcBTE ΔfadAB::trcBTE | This work |
| TY32 | MG1655 ΔaraBAD ΔfadR ΔfadE::trcBTE ΔfadAB::trcBTE | This work |
| TY33 | MG1655 ΔaraBAD ΔfadD ΔfadE::trcBTE ΔfadAB::trcBTE | This work |
| TY34 | MG1655 ΔaraBAD ΔfadE::trcBTE ΔfadAB::trcBTE ΔackApta::trcBTE Φ($P_{Trc}$-fadD) | This work |
| Plasmids | | |
| pBTRKtrc | $P_{trc}$ promoter, pBBR1 origin, Kan$^R$ | This work |
| pUCtrc | $P_{trc}$ promoter, pUC origin, Amp$^R$ | This work |
| pACYCtrc | $P_{trc}$ promoter, pACYC origin, Cm$^R$ | This work |
| pACYC-fadD | pACYCtrc carrying fadD under $P_{trc}$ control, Cm$^R$ | This work |
| pACYC-PP0763 | pACYCtrc carrying PP_0763 (*P. putida*) under Ptrc control, CmR | This work |
| pACYC-fadD6 | pACYCtrc carring fadD6 (*M. tuberculosis*) under $P_{trc}$ control, Cm$^R$ | This work |
| pTrc99A | $P_{Trc}$ promoter, pBR322 origin, Amp$^R$ | Amann et al., 1988 |
| ACR1 | pTrc99A carrying acr1 from *Acinetoacter calCoAceticus* under $P_{trc}$ control, Amp$^R$ | This Work |

TABLE 1-continued

Strains and plasmids

| Strain/Plasmid | Relevant Genotype/Property | Source or Reference |
|---|---|---|
| FAR6 | pTrc99A carrying far6 from *Arabidopsis thaliana* under $P_{trc}$ control, $Amp^R$ | This work |
| ptrc99a-MAACR | pTrc99A carrying MAACR from *Marinobacter aquaeolei* under Ptrc control and fused to a maltose binding protein, $Amp^R$ | This work |
| pBTRK-MAACR | pBTRKtrc containing MAACR | This work |
| pACYC-MAACR | PACYCtrc containing MAACR | This work |
| pUCtrc-MAACR | pUCtrc containing MAACR | This work |

Reagents and Media

Enzymes were purchased from New England Biolabs (Ipswich, Mass.). Nucleic acid purification materials were purchased from Qiagen (Venlo, Netherlands), Promega (Madison, Wis.), or Thermo Scientific (Waltham, Mass.). Chemicals were purchased from Sigma-Aldrich (St. Louis, Mo.) or Fisher Scientific (Hampton, NH) unless otherwise specified. Oligonucleotides (sequences are listed in Table 2) were purchased from Integrated DNA Technologies (Coralville, Iowa). For all growth experiments, single colonies obtained from freezer stocks were used to inoculate 5 mL LB starter cultures grown overnight prior to the inoculation of experimental cultures. All shake flask growth experiments were performed at 30° C. in a rotary shaker (250 rpm). Cultures were supplemented with appropriate antibiotics (100 µg mL$^{-1}$ ampicillin and/or 50 µg mL$^{-1}$ kanamycin and/or 34 µg mL$^{-1}$ chloramphenicol) where necessary.

Plasmid Construction

All plasmids used in this study are listed in Table 1. Enzyme encoding genes were cloned from native sources if each had been successfully expressed in *E. coli* at 30° C. If not, codon-optimized variants were custom synthesized. *E. coli* acyl-CoA synthetase fadD was amplified by PCR from genomic DNA isolated from *E. coli* MG1655. Codon optimized versions of the acyl-CoA synthetase fadD6 (Accession number: WP_003900292), acyl-CoA reductase acr1 (Accession number: P94129), and acyl-CoA reductase far6 (Accession number: B9TSP7) were custom synthesized by Life Technologies (Carlsbad, Calif.). *P. putida* KT2440 genomic DNA was used as a template to PCR amplify PP_0763 (Accession number: NP_742924). MAACR (Accession number: A1U3L3) was amplified by PCR from a plasmid containing the *Marinobacter aquaeolei* acyl-CoA reductase generously donated by Dr. Brett Barney (Univer-

TABLE 2

Oligonucleotide primers

| Primer Name | Sequence (5' to 3') |
|---|---|
| 1. Forward rrnb | gaaaggttttgcaccattcgatggtgtCggtgcctaatgagtgagctaac (SEQ ID NO:23) |
| 2. Reverse before lacI | gaaaggttttgcaccattcgatggtgtCggtgcctaatgagtgagctaac (SEQ ID NO:24) |
| 3. Forward before lacI | atcgaatggtgcaaaaccttc (SEQ ID NO:25) |
| 4. Reverse from rrnb to get MCS, ptrc, and lacI | gaaacgcaaaaaggccatcc (SEQ ID NO:26) |
| 5. Gibson MAACR fwd (MAACR gib F) | acacaggaaacagaccatCACCAACAAGGACCATAGC (SEQ ID NO:27) |
| 6. Gibson MAACR rev (MAACR gib R) | tcatccgccaaaacagcTTATCAGTGATGGTGATGATGG (SEQ ID NO:28) |
| 7. fadD fwd | gaaaagagctcggtaccAGGAGGTATAAGAAttgaagaaggtttggcttaacc (SEQ ID NO:29) |
| 8. fadD rev | gaaaagtcgactctagattaTCAGGCTTTATTGTCCACTTTGC (SEQ ID NO:30) |
| 9. BTEack-pta_int_F | atgttaatcataaatgtcggtgtcatcatgcgctacgctcGGCATGCGTTCCTAT TCCGAAGTTCC (SEQ ID NO:31) |
| 10. BTEack-pta_int_R | agcgcaaagctgcggatgatgacgagattactgctgctgtTACATCCGCCAAA ACAGCCAAG (SEQ ID NO:32) |
| 11. PP0763 fwd | GAGAAAgagctcggtaccAGGAGGTAAAATAATGTTGCAGAC ACGCATCATC (SEQ ID NO:33) |
| 12. PP0763 rev | GAAAAGcctgcaggtctagaTTAGTGATGGTGATGGTGATGCA ACGTGGAAAGGAACGC (SEQ ID NO:34) |
| 13. rev from start of MCS (ptrc gib R) | atggtctgtttcctgtgtg (SEQ ID NO:35) |
| 14. fwd from end of MCS (ptrc gib F) | gctgttttggcggatgag (SEQ ID NO:36) |
| 15. MAACR qPCR fwd | ctatgtctcctcgaaatc (SEQ ID NO:37) |
| 16. MAACR qPCR rev | gaatcgtagatcttggtg (SEQ ID NO:38) |
| 17. ompA qPCR fwd | tgttgagtacgcgatcactc (SEQ ID NO:39) |
| 18. ompA qPCR rev | gttgtccggacgagtgc (SEQ ID NO:40) | sity of Minnesota). Base plasmids pBTRKtrc, pACYCtrc, and pUCtrc were constructed by generating PCR products using primers 1 and 2 to amplify the antibiotic resistance marker and origin of replication from plasmids pBAD35, pBAD33, and pBAD34 (Lennen et al., 2010) respectively. Primers 3 and 4 were then used to amplify the multi-cloning site, $P_{trc}$ promoter, and $lacI^q$ region from pTrc99a. The PCR products were combined using the Gibson assembly method (Gibson et al. 2009). To construct each of the individual expression plasmids, pBTRKtrc, pACYCtrc, pTrc99a, and pUCtrc were amplified with primers 13 and 14, and MAACR was amplified with primers 5 and 6. These PCR products were then combined using the Gibson assembly method to generate the constructs listed in Table 1. For the codon optimized genes acr1 and far6, pTrc99a and the vectors containing the genes were digested with Kpn I and Hind III, ligated with an analogous digest of pTrc99a using T4 DNA ligase. The same procedure was used with the codon optimized fadD6 and pACYCtrc. For the other CoA synthetases, the PCR products from fadD (7 and 8) and PP_0763 (11 and 12) were digested with Kpn I and Xba I, and ligated with digested pACYCtrc. All constructs were confirmed by DNA sequencing.

Culturing Conditions

Figure 2:
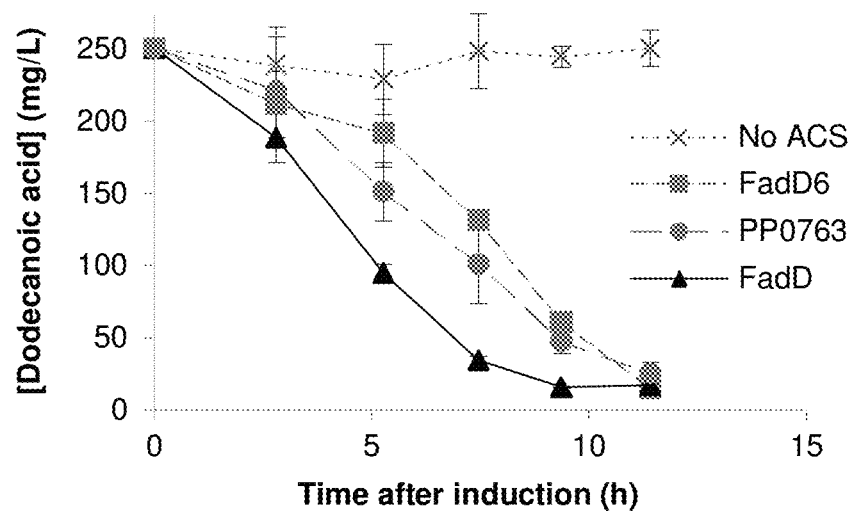
FIG. 2 shows a comparison of dodecanoic acid consumption by E. coli expressing various acyl-CoA synthetases. E. coli MHS04 (ΔfadR ΔfadD) harboring one of four acyl-CoA synthetase expression plasmids (medium copy, P$_{trc}$) was fed dodecanoic acid. The rate of consumption was fastest for the strain expressing FadD. The control strain carried the empty pACYCtrc plasmid. The error bars represent standard deviations from biological triplicate shake flask cultures.
Figure 3A:
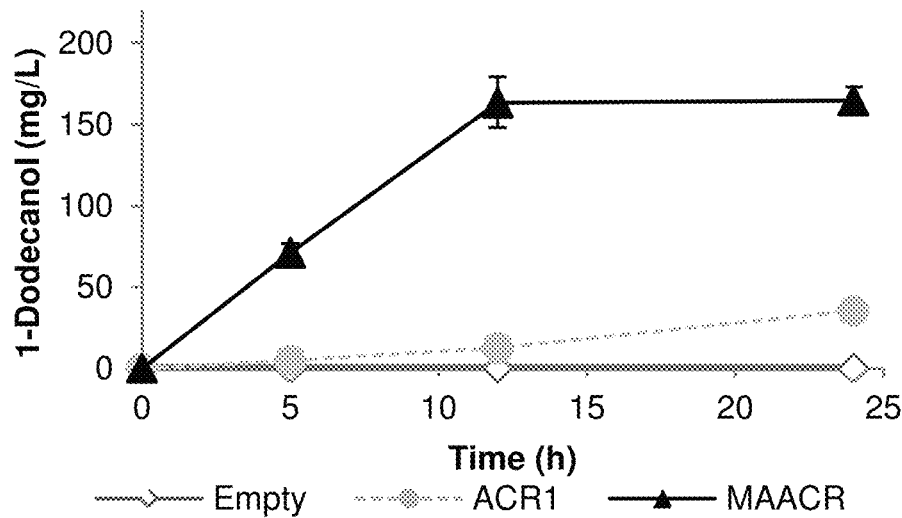
FIGS. 3A and 3B show a comparison of 1-dodecanol production (FIG. 3A) and dodecanoic acid consumption (FIG. 3B) by E. coli expressing various acyl-CoA reductases. Dodecanoic acid was exogenously supplied in media to E. coli MHS01 (ΔfadE Φ[P$_{trc}$-fadD]) harboring one of three plasmids—pTRC99A, pTRC99A-ACR1, or pTRC99A-MAACR. The error bars represent standard deviations from biological triplicate shake flask cultures.
Figure 3B:
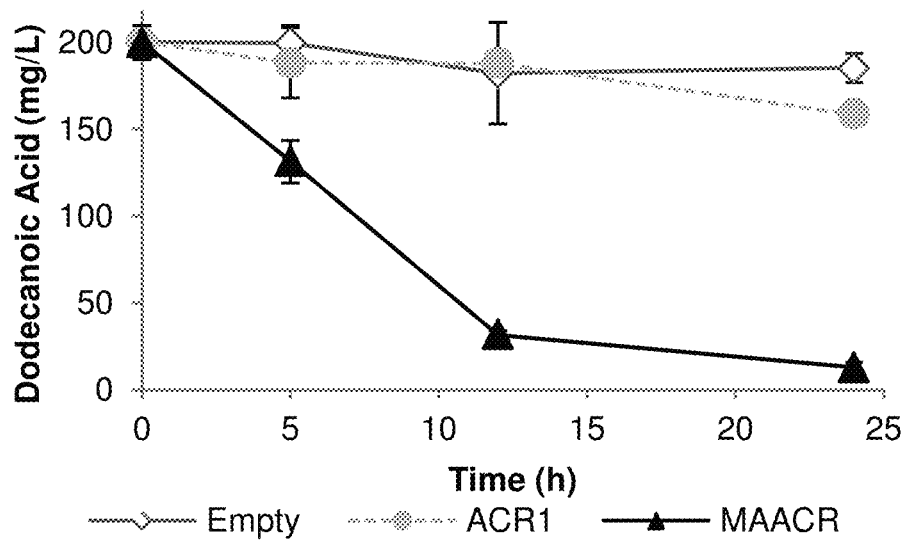

For experiments where dodecanoic acid was supplied exogenously (FIGS. 1, 2, and 3), each strain was cultured in 50 mL LB starting with an inoculum at optical density ($OD_{600}$) of 0.02. At $O_{D600}$ 0.2, cultures were induced with 1 mM isopropyl β-D-thiogalactopyranoside (IPTG) and supplemented with either 40 (for alcohol production studies) or 50 μL (for dodecanoic acid consumption studies) of a 250 mg/mL solution of dodecanoic acid in ethanol (initial [dodecanoic acid]=200 or 250 mg/L). After induction, cultures were incubated at 30° C. with shaking and 2.5-mL culture samples were taken at either 2.5, 7, 9, and 11 or 4, 8, 12, and 24 hours after induction for dodecanoic acid consumption and alcohol production studies, respectively. Culture samples were processed for FAME analysis as described previously (Agnew et al. 2012).

For fatty alcohol production experiments (FIGS. 4 and 5), each strain was inoculated to an $OD_{600}$ of 0.02 in 50 mL LB+0.4% glycerol and induced with 1 mM IPTG at an $OD_{600}$ of 0.2. Following induction, cultures were incubated with shaking at 30° C. for 48 hours. Culture samples of 2.5 mL were taken at 24 and 48 hours for fatty alcohol and FAME analysis. To determine the fraction of fatty alcohol associated with cells, an additional 10 mL sample from the 48 hour timepoint was centrifuged at 4000×g for 10 min and the resulting cell pellet was resuspended to 10 mL in 1×PBS. After repeating the process, 2.5 mL of the resuspended cell pellet was taken for fatty alcohol and FAME analysis.

Bioreactor experiments (FIG. 6) were performed in a 3-L stirred bioreactor (Applikon Biotechnology, Inc., Schiedam, Netherlands), using a 1 L working volume. Temperature was maintained at 30° C. using a heat blanket (Applikon, model number M3414) and cooling water. Reactor temperature, pH and dissolved oxygen ($DO_2$) were monitored using specific probes (Applikon). Carbon dioxide and oxygen off-gas levels were monitored using a Blusens BlueInOne Ferm (Blusens, Herten, Germany). Reactor pH was maintained at 7.00±0.01 by the addition of 10% (v/v) $NH_4OH$ or 1 M HCl solutions. Agitation was provided by a single impeller with the stir speed set between 240-320 rpm. Stirrer speed was varied to ensure the $DO_2$ content did not decrease below 40% saturation in order to maintain an aerobic environment (Becker et al., 1997; Tseng et al., 1996). The air inflow rate was maintained at 1.0 L/min.

Bioreactor experiments (FIG. 6) were performed using a phosphate limited MOPS minimal media recipe (Youngquist et al., 2013). Cultures were inoculated to an $OD_{600}$ of 0.04 using a culture of *E. coli* MHS03, TY30, or TY34 containing pBTRK-MAACR grown to an OD600 >2 in MOPS minimal media (Neidhardt et al., 1974) supplemented with 0.7% glucose overnight. Bioreactor starting media was MOPS minimal media supplemented with 0.7% glucose, 0.276 mM potassium sulfate, and 9.5 mM ammonium chloride but containing only 370 μM $K_2HPO_4$. Cultures were induced with 1 mM IPTG at $OD_{600}$ 0.2. Each experiment was performed using a discontinuous fed-batch where a bolus of 2 g glucose (10 mL of a 20% (w/v) glucose solution) was added at 18, 24, 30, 42, and 48 hours post-induction. In three experiments, 20 mL dodecane was added to the culture 6 hours after induction to provide a sink for fatty alcohols. For all experiments, $CO_2$ off-gas levels and pH were measured continuously and culture samples (10 mL) were taken periodically prior to glucose additions to determine $OD_{600}$, as well as the concentrations of glucose, acetate, fatty alcohols, and fatty acids.

Fatty Acid and Fatty Alcohol Extraction and Characterization

FAME analysis was performed on 2.5 mL of culture, supernatant, or resuspended washed cell pellet as described previously (Lennen et al., 2010). Analysis of fatty alcohols followed the same procedure except 20 μL of 10 mg/mL pentadecanol in ethanol was added to the chloroform methanol mix as an internal standard in addition to the fatty acid internal standards.

Quantitative-PCR

To quantify plasmid copy number (FIG. 4C), cells were collected (500 μm) at $OD_{600}$ 0.4 as well as at 24 hours post-induction. Collected cells were centrifuged at 16,000×g for 1 minute, snap frozen in liquid nitrogen, and stored at −80° C. In preparation for quantitative PCR, cell pellets were resuspended in 50 μl of nuclease-free water for the 0.4 $OD_{600}$ samples and 500 μl of water for the 24 hour samples. One microliter of cell suspension was used directly in a quantitative PCR reaction using Bio-Rad iQ SYBR green supermix (Bio-Rad, Hercules, Calif.). Primers were used for amplifying plasmid based MAACR and chromosomal ompA. SYBR green fluorescence was measured over time with a CFX real-time thermocycler (Bio-Rad). Threshold cycle ($C_t$) values were calculated by regression analysis using Bio-Rad CFX manager software. Plasmid copy numbers of experimental samples were determined by establishing a standard curve for both the MAACR and ompA genes using purified pUC19-MAACR and TY30 genomic DNA, respectively.

For RNA samples, 1 mL of culture at an $OD_{600}$ of 0.8 was centrifuged at 8000×g for 3 minutes at 4° C. The supernatant was quickly removed and then the cell pellet was snap frozen in a dry ice ethanol bath for 5 minutes before storing the samples at −80° C. until further processing. RNA was isolated using an RNeasy mini kit (QIAgen). Residual DNA was digested using the Ambion DNA-Free™ Kit (Applied Biosystems). The corresponding cDNA was synthesized using the GoScript™ Reverse Transcription System (Promega) following manufacturer's instructions. To run the qPCR, the Maxima SYBR Green/Fluorescein qPCR Master Mix (Thermo Scientific) was used. Primers were designed for amplifying both a 100 bp region of fadD and a 100 bp region of rrsA to act as a reference for normalization of samples (Kobayashi et al., 2006).

Results
Establishing Production of 1-Dodecanol in E. coli
Fatty alcohol production was established in E. coli by heterologous expression of enzymes that catalyze reduction of acyl-thioesters and the resulting fatty aldehydes. In addition, two modifications of the E. coli MG1655 chromosome were introduced to produce 1-dodecanol from exogenously fed dodecanoic acid (FIG. 1A). First, β-oxidation was blocked to prevent consumption of the exogenously fed free fatty acid. Small amounts of 1-dodecanol was produced when this objective was accomplished by deleting fadE (encoding acyl-CoA dehydrogenase/enoyl-CoA reductase). Second, enhanced acyl-CoA synthetase (FadD) activity was generated for converting the exogenous lauric acid to the corresponding acyl-CoA thioester, a substrate for the heterologously expressed acyl-CoA/ACP reductase (i.e. MAACR from Marinobacter aquaeolei VT8 in FIG. 1B). Unexpectedly, the ΔfadE strain only converted 18% of the lauric acid fed to the culture. The fractional conversion of lauric acid to 1-dodecanol was increased when the levels of FadD were elevated by replacing the native $P_{fadD}$ with the strong, IPTG inducible $P_{trc}$ promoter. In all strains, small amounts of 1-hexadecanol (15-20% of the endogenous hexadecanoic acid content) were produced (FIG. 1C), demonstrating the activity of MAACR towards both native $C_{16}$ acyl-ACPs and $C_{12}$-acyl-CoAs derived from exogenous lauric acid.

Impact of Various Acyl-CoA Synthetase on Consumption of Lauric Acid
Given the dependence of 1-dodecanol conversion on acyl-CoA synthetase activity, the impact of three candidate synthetases on dodecanol production was examined by determining the rates of lauric acid consumption in E. coli MHS04 (ΔfadD, ΔfadR). Deletion of fadR removed repression of enzymes involved in β-oxidation (Dirusso et al., 1992) and increased the likelihood that acyl-CoA synthesis was the rate limiting step in lauric acid consumption. FadD and two alternative acyl-CoA synthetases were cloned into a medium copy plasmid and expressed from the $P_{trc}$ promoter. The second acyl-CoA synthetase gene, fadD6 from M. Tuberculosis, was chosen because it has high activity toward $C_{12}$ fatty acids and is soluble even when highly expressed (Arora et al., 2005). A third acyl-CoA synthetase, PP_0763 from Pseudomonas putida, was selected because of its ability to activate $C_{12}$ fatty acids and enhance medium chain length PHA production (Agnew et al., 2012; Wang et al., 2012). While each of the CoA synthetases conferred the ability to consume 250 mg/L lauric acid within 12 hours (FIG. 2), the strain expressing fadD was able to consume over 90% of the fed fatty acid within 8 hours. Each of the other ligases took at least 11 hours to reach the same mark. Based on this data, FadD was selected as the preferred acyl-CoA synthase for the fatty alcohol production pathway.

Selection of Acyl-CoA Reductase
Once fadD was selected as the preferred acyl-CoA synthetase (acyl-CoA ligase), the acyl-CoA reductase well-suited for the conversion of $C_{12}$ acyl-CoAs into fatty alcohols was determined. Genes coding for three different types of acyl-CoA reductases (acr1 from Acinetobacter calcoaceticus (Reiser and Somerville 1997), far6 from Arabidopsis thaliana (Doan et al. 2009), and MAACR from Marinobacter aquaeolei VT8 (Willis et al., 2011)) were tested to see which allowed for the highest conversion of free fatty acids to fatty alcohols. Heterologous expression of a codon-optimized variant of far6 failed to produce 1-dodecanol when cultures were fed dodecanoic acid (data not shown). Conversely, heterologous expression of both acr1 and MAACR resulted in conversion of exogenous dodecanoic acid to 1-dodecanol. In these experiments, acyl-CoA reductases were expressed from medium copy plasmids harboring the IPTG inducible $P_{trc}$ promoter in strain MHS01 (ΔfadE Φ[$P_{Trc}$-fadD]). MAACR facilitated the fastest conversion of dodecanoic acid to 1-dodecanol (FIG. 3), with 80% of the initial fed dodecanoic acid being converted to dodecanol within 12 hours after induction. One advantage of MAACR is its ability to also reduce dodecanaldehyde, by-passing endogenous aldehyde reductase activity and minimizing production of potentially toxic intermediates. Thus, MAACR was chosen as the preferred acyl-CoA reductase for future alcohol production experiments.

Determining Optimal Expression Levels of Acyl-CoA Synthesis and Reduction Under Conditions of Endogenous Fatty Acid Production
In order to use sugars as a feedstock for alcohol production, the medium chain length thioesterase (BTE) from Umbellularia californica (Voelker and Davies 1994) was heterologously expressed in E. coli to endogenously produce $C_{12}$ and $C_{14}$ free fatty acids for subsequent conversion to the corresponding alcohols. A family of fatty acid producing strains were constructed by inserting a DNA cassette containing BTE under the control of the IPTG inducible $P_{trc}$ promoter into various genomic loci (fadE, fadAB, and ackA-pta). Increasing BTE copy number (up to 3 copies) has been shown to increase free fatty acid titers (Youngquist et al. 2012). In an effort to balance the expression of the downstream reductive activities with fatty acid production, the acyl-CoA reductase from M. aquaeolei, MAACR, was cloned onto a series of plasmids (origins of replication: pBBr1, pACYC, pBR322, and pUC) that were determined to have copy numbers of 1.74±0.12, 7.26±1.33, 14.52±1.93, and 56.37±19.94 (relative to ompA) at $OD_{600}$ of 0.4. Each MAACR plasmid was expressed in either MHS03 (1×BTE) or TY30 (2×BTE) to identify the optimal level of gene expression for each activity. Each strain contained elevated acyl-CoA synthetase activity in the form of a Ptrc-fadD chromosomal cassette.

Strains expressing MAACR from the low copy number pBBr1 origin plasmid produced the most fatty alcohols (FIGS. 4A-C), while strains with the high copy number pUC origin plasmid produced the least. Additionally, the strains containing the pUC origin plasmid displayed significantly impaired growth compared to the other strains (data not shown), suggesting a high metabolic burden associated with over-expression of MAACR. Surprisingly, there was small difference in final fatty alcohol titer between the same plasmid expressed in either the MHS03 or TY30 strain.

Figure 5A:
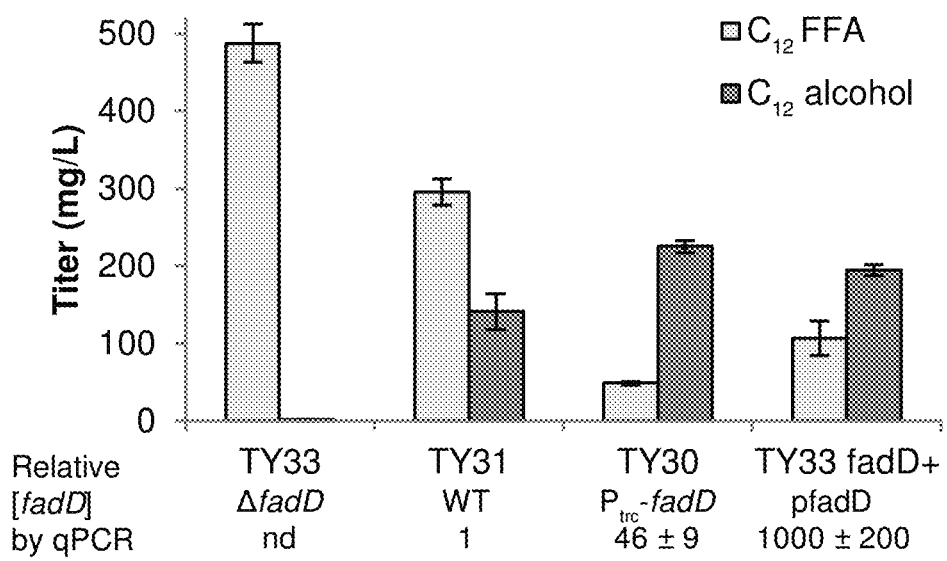
FIGS. 5A and B show dodecanol (FIG. 5A) and tetradecanol (FIG. 5B) production as a function of the relative expression level of acyl-CoA synthetase (fadD) in *E. coli* strains harboring pBTRK-MAACR compared to native expression (TY31). Error bars represent standard deviation from biological triplicate shake flask cultures.
Figure 5B:
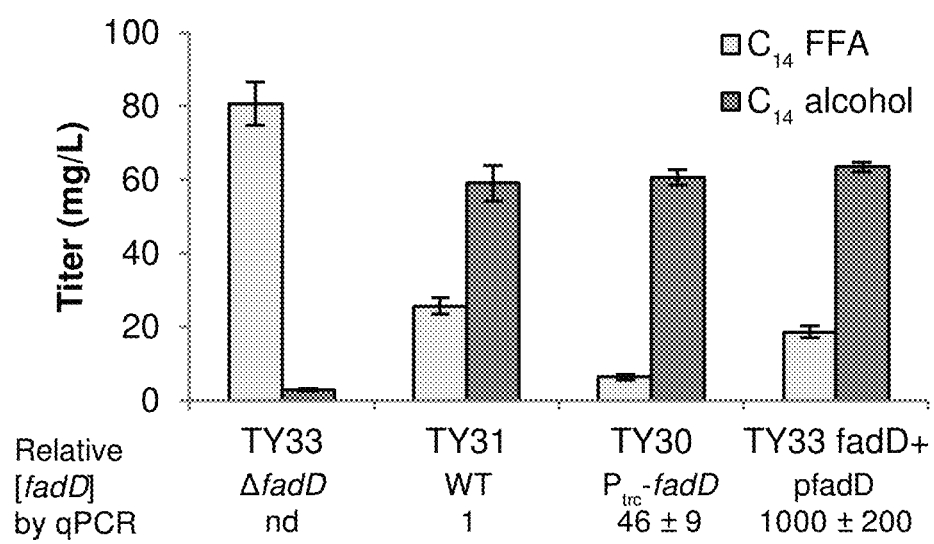

To optimize the level of acyl-CoA synthetase activity, a family of strains was constructed to vary fadD expression. E. coli TY33 (ΔfadD), TY31 (native fadD), and TY30 (ΦP$_{trc}$-fadD), were transformed with pBTRK-MAACR and either pACYCtrc or pACYC-fadD. Expression of fadD was quantified by qPCR using RNA samples isolated at an $OD_{600}$ of 0.8. The fadD promoter replacement resulted in the maximum production of both 1-dodecanol (FIG. 5A) and 1-tetradecanol (FIG. 5B). The promoter replacement increased fadD levels by 46±10 fold while expression from a medium copy plasmid increased expression by 1000±200 fold relative to fadD under its native promoter on the chromosome.

Endogenous Production of Dodecanol and Tetradecanol from Glucose
To determine fatty alcohol yield, strains MHS03 (1×BTE), TY30 (2×BTE), and TY34 (3×BTE) each containing pBTRK-MAACR were cultivated in MOPS minimal media using glucose as a carbon source in controlled bioreactors. To simulate a fed batch, a bolus of 2 g glucose was added on five separate occasions. After 120 hours the final fatty alcohol titer was 280, 470, and 1185 mg/L for the MHS03, TY30, and TY34 versions, respectively, with over 90% coming from 1-dodecanol and 1-tetradecanol (FIG. 6). Based on the amount of glucose consumed by these cultures, the resulting yields were 0.031, 0.040, and 0.097 g fatty alcohol per g glucose consumed for the MHS03, TY30, and TY34 strains expressing MAACR, respectively.

In each experiment, a slight white sludgy material (assumed to be fatty alcohol) was deposited on the bioreactor wall. This material prevented an accurate timecourse of fatty alcohol production from being taken. To bypass the problem, 20 mL of dodecane was added to the fermentation 6 h after induction. Three replicates of TY34 containing pBTRK-MAACR were run in controlled bioreactor fermentations with the dodecane emulsion. The addition of dodecane allowed for an accurate timecourse of fatty alcohol production to be taken and increased the final fatty alcohol titers to 1.65 g/L (0.134 g alcohol/g glucose consumed, FIG. 6A). Samples were taken to monitor biomass, $CO_2$, acetate, free fatty acids, and other excreted metabolites (FIGS. 6B, 6C, 6D, and 6F). Analysis of these samples led to a carbon balance accounting for 86% of the carbon, with elevated levels of acetate and $CO_2$ being produced.

Figure 6A:
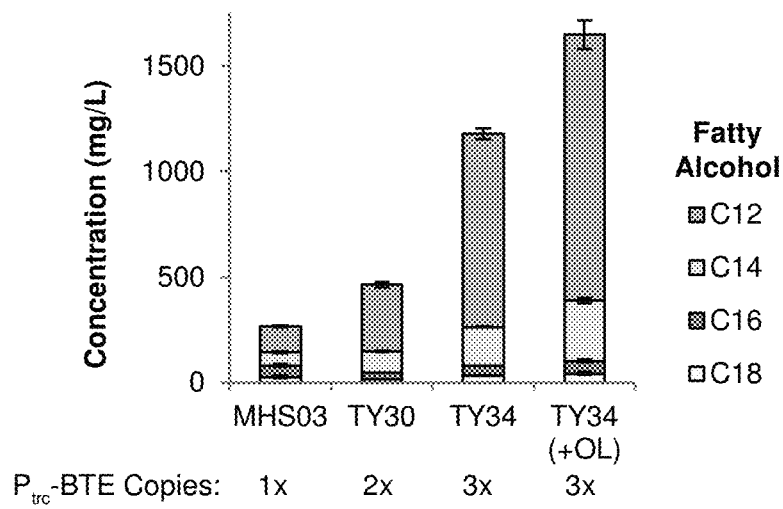
FIG. 6A shows the final observed fatty alcohol titer breakdown in strains MHS03 (1 copy of BTE), TY30 (2 copies of BTE), and TY34 (3 copies of BTE) harboring pBTRK-MAACR after being run in a stirred bioreactor. "OL" refers to the presence of a dodecane overlayer added during fermentations.
Figure 6B:
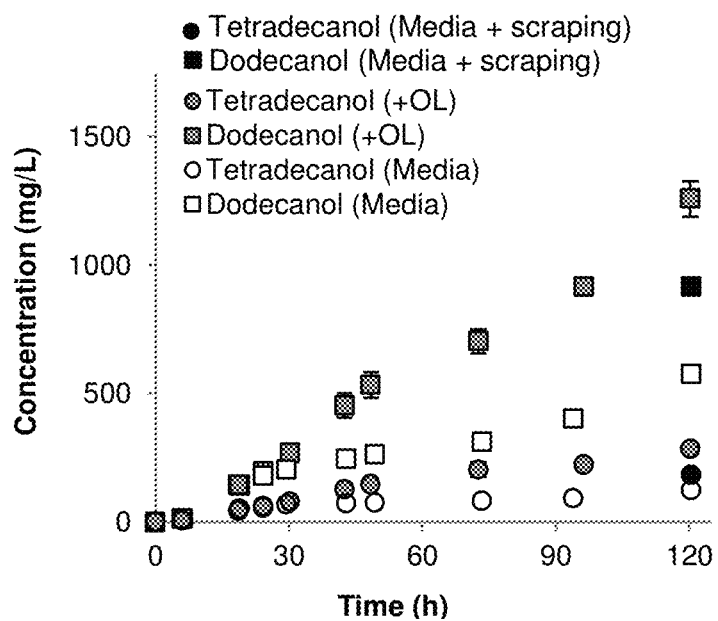
FIGS. 6B-E show data from fed-batch cultivations of *E. coli* TY34 pBTRK-MAACR.
Figure 6C:
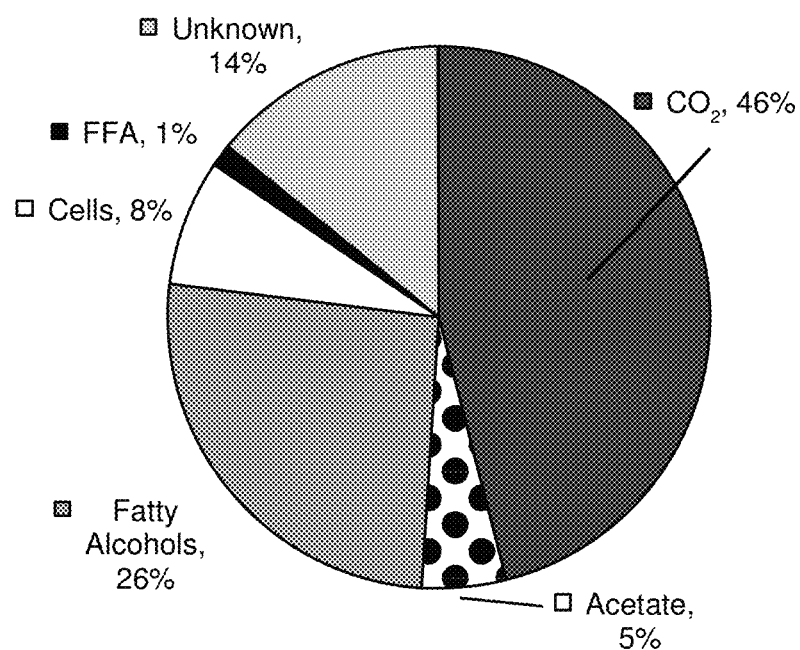
Figure 6D:
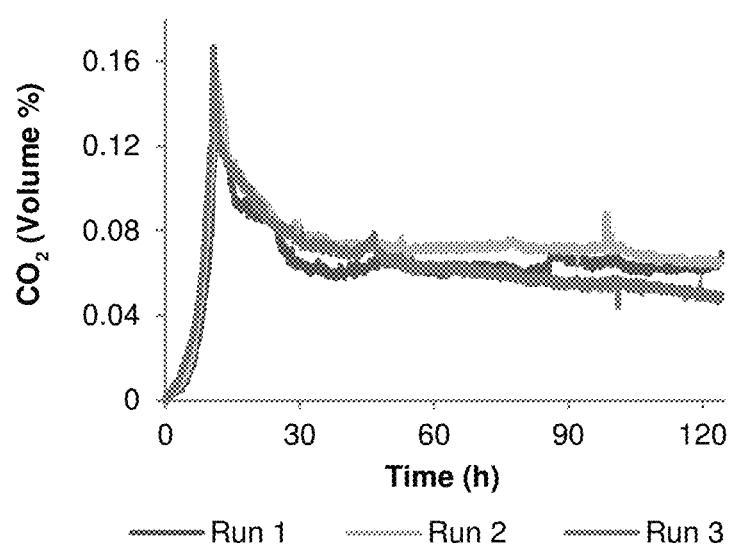
Figure 6E:
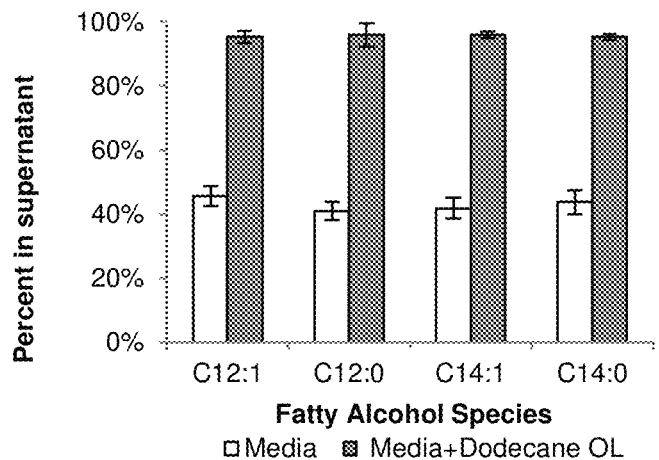
Figure 6F:
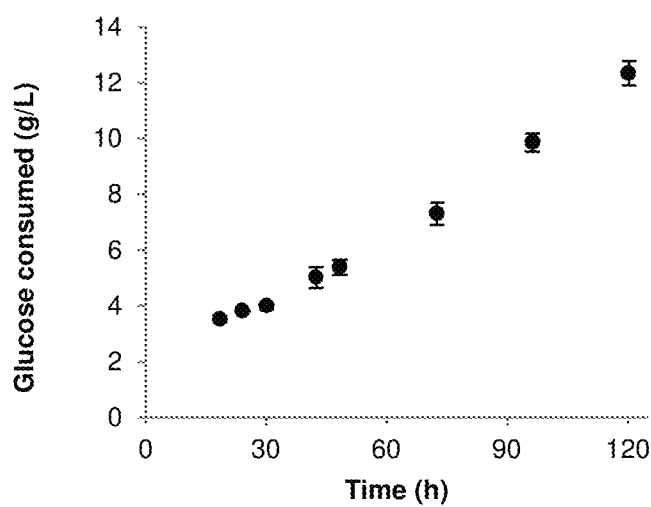
FIG. 6F depicts glucose consumed as a function of time and shows that glucose consumption was nearly linear over the fed-batch portion of the culture.

Separate samples for the supernatant and cell pellet were taken at the last time point of each bioreactor run to determine if the addition of dodecane allowed for an increased transport of fatty alcohols to the extracellular medium. Less than 5% of the free fatty acids and fatty alcohols were found in the cell pellet fraction from cultures grown in co-culture with dodecane (FIG. 6E). In contrast, approximately 60% of the fatty alcohol species were found in the cell pellet fraction in cultures grown without dodecane (FIG. 6E).

Discussion
Selection of Acyl-CoA Reductases

The selection of an acyl-CoA reductase influences fatty alcohol production in multiple ways. Biosynthesis of specific chain length fatty alcohols requires cleavage and reduction of the corresponding acyl-thioester (-CoA or -ACP) to a fatty aldehyde. The distribution of chain lengths for most fatty alcohol producers matches the strain's fatty acid profile, indicating that the reductase activity/affinity is not strong (or at least weaker than that of fatty acid elongation) for shorter chain substrates. Conversely, thioesterases are known to have high activity on a wide range of acyl-thioester chain lengths depending on the specific enzyme. The disadvantage of utilizing thioesterases for fatty alcohol production is the need to reactivate the acyl-chain for reduction. If acyl-ACP reductases could be engineered to have stronger activities towards specific acyl-ACPs, higher yields could be achieved. Similar efforts to engineer chain length specificity in thioesterases has been reported in the patent literature (Yuan et al., 1999) and could guide acyl-ACP reductase engineering.

Here, expression of the dual-activity acyl-CoA reductase, MAACR, led to the highest fatty alcohol productivity. It is likely that substrate channeling between the acyl-ACP and fatty aldehyde reduction domains prevented release of the reactive, potentially toxic, aldehyde intermediate. If novel, high-activity acyl-CoA reductases are identified, fusion (or incorporation into a complex via a protein scaffold) of aldehyde reductases could have similar benefits (Dueber et al. 2009). Alternatively, separate enzymes could be targeted to microcompartments to sequester the aldehydes from the cytoplasm. Many bacteria use this strategy to avoid the toxicity of aldehyde intermediates and/or increase the local concentration of substrates when enzymes have weak activity (Sampson and Bobik 2008; Frank et al., 2013). While this strategy is promising, the microcompartments would need to be engineered to transport the substrates (e.g. acyl-ACP) and products.

Balancing Expression of CoA Synthetase and Acyl-CoA Reductase

One of the metabolic engineering objectives in this study was to tailor the expression levels of the acyl-CoA synthetase and acyl-CoA reductase to balance the overall conversion between fatty acid and fatty alcohol. The optimal levels of acyl-CoA synthetase and acyl-CoA reductase that maintain balanced activity could be determined from knowledge of the in vivo kinetic parameters ($k_{cat}$, $K_m$), if known. Based on in vitro experiments, the specific activity and $K_m$ for fadD conversion of lauric acid to lauryl-CoA are 2,630 nmol/min/mg protein and 1.6 µM, respectively (Kamedas and Nunn 1981). For the conversion of lauryl-CoA to the aldehyde intermediate, the specific activity of MAACR in vitro is 34 nmol/min/mg enzyme and the $K_m$ is 4 µM (the specific activity for the second step, aldehyde to alcohol, is two orders of magnitude higher) (Willis et al., 2011). These values suggest that the $k_{cat}/K_m$ ratio is about 100 fold higher for the acyl-CoA synthetase step than the reductase step. Optimal production of fatty alcohols occurred with MAACR on a low copy (~2:1 ratio to genomic DNA) plasmid using the same promoter as the chromosomal $P_{trc}$-fadD cassette (Lennen et al., 2010). High overexpression of MAACR decreased fatty alcohol titer, placing an upper limit on acyl-CoA reductase activity. This observation could be attributed to metabolic burden of protein overexpression or improper folding of MAACR expressed at a high level. Prior studies have shown that soluble overexpression of MAACR is problematic without addition of an N-terminal maltose binding protein (Willis et al., 2011), which was used in this study. FIGS. 5A and B shows that a 45 fold decrease in fadD transcript levels, between that controlled by $P_{trc}$ promoter and the native promoter, resulted in only a 50% decrease in fatty alcohol titer. This result suggests that further strain optimization could be achieved by decreasing fadD expression. This strategy is consistent with the optimal ratio of MAACR and FadD levels predicted by their relative in vitro kinetics.

Improving Fatty Alcohol Yield

Implementation of the metabolic engineering strategy described above generated a strain that produced the highest reported yield (0.134 g/g) and titer of fatty alcohols (1.65 g/L fatty alcohols, with 77% and 17% being C12 and C14 species, respectively) from glucose. Previous studies that leveraged native fatty acid biosynthesis pathways produced fatty alcohol titers of up to ~450 mg/L C12-14 fatty alcohols with yields less than 0.01 g fatty alcohol/g carbon source (Steen et al. 2010; Zheng et al. 2012). Alternative pathways in E. coli have yielded up to ~350 mg/L fatty alcohols and yields up to 0.05 g fatty alcohol/g carbon source (Akhtar et al., 2013; Dellomonaco et al., 2011). Based on theoretical yields, E. coli is capable of producing 0.32 g 1-dodecanol per g glucose fed. As current yields are much less than theoretical, further optimization and metabolic engineering efforts are needed to improve yield. However, current yields of combined C12-14 fatty acids and fatty alcohols are similar to that seen in a corresponding FFA producing strain (Youngquist et al., 2013), indicating that efforts should focus on redirecting carbon flux toward fatty acid biosynthesis (Lennen and Pfleger 2012) rather than the conversion to fatty alcohol. The carbon balance on the bioreactor (FIGS. 6C and D) indicate that a significant amount of fed carbon is going to carbon dioxide production. Therefore, decreasing flux to $CO_2$ production could lead to improved fatty alcohol titers. Similarly, a small percentage of carbon flux ended in the secretion of acetate (FIG. 6C). Given that TY34 is ΔackAΔpta, it is likely that the observed acetate was generated by the pyruvate oxidation pathway that concurrently generates proton motive force, as it is coupled to the electron transport chain (Abdel-Hamid et al., 2001). Deletion of poxB would eliminate acetate production through this pathway and potentially increase fatty alcohol yields (Zha et al. 2009; Peng Xu et al. 2013). Other studies have successfully achieved higher yields of fatty acids by overexpressing genes fabZ (Ranganathan et al. 2012) (SEQ ID NOS:20 (coding sequence) and 21 (protein)) or fadR (Zhang et al. 2012) (SEQ ID NOS:21 (coding sequence) and 22 (protein)). These or similar manipulations employed in conjunction with this metabolic engineering strategy could lead to fatty alcohol production at yields closer to the theoretical limit and are encompassed by the present invention.

The high yield and titer reported above was achieved by cultivating strain E. coli TY34 pBTRK-MAACR in a 1-L working volume using a fed-batch strategy. One interesting observation from this experiment was the consistent production of fatty alcohols and consumption of glucose (FIG. 6) during a prolonged stationary phase (>96 hours). Such a result may be expected due to the unique qualities of phosphate starvation, in which metabolic activity in the cell remains high despite no further cell growth (Ballesteros et al., 2001). During stationary phase a specific productivity of 0.016 g fatty alcohol/gDCW/h was observed and a glucose consumption rate of 0.11 g glucose/gDCW/h. A better understanding of metabolism and regulation under these conditions will help guide efforts to maintain the stability of producing strains and maximize the time strains can spend in the production phase.

CONCLUSIONS

*Escherichia coli* was engineered to produce 1-dodecanol and 1-tetradecanol from glucose. Cultivation of the strain in a bioreactor with 10% dodecane achieved the highest reported titer (1.65 g/L) and yield (0.134 g fatty alcohol/g glucose) from a minimal glucose based media to date. The key steps to optimize this fatty alcohol producing strain were selection of FadD from *E. coli* as the acyl-CoA synthetase and MAACR from *M. aquaeolei* VT8 as the acyl-CoA reductase. In addition, high overexpression of these two enzymes was found to be detrimental to fatty alcohol productivity. The optimal expression levels were found by replacing the native $P_{fadD}$ promoter with a stronger inducible promoter ($P_{trc}$) and expressing MAACR from a low copy vector. The yields observed were nearly equivalent to the yield of free fatty acids in past work (Youngquist et al, 2013), suggesting that the strain may be capable of higher yields if free fatty acid production could be increased.

REFERENCES

Abdel-Hamid, a M., Attwood, M. M., Guest, J. R., 2001. Pyruvate oxidase contributes to the aerobic growth efficiency of *Escherichia coli*. *Microbiology* (Reading, England) 147, 1483-98.

Agnew, D. E., Stevermer, A. K., Youngquist, J. T., Pfleger, B. F., 2012. Engineering *Escherichia coli* for production of C12-C14 polyhydroxyalkanoate from glucose. *Metab. Eng.* 14, 705-13.

Akhtar, M. K., Turner, N. J., Jones, P. R., 2013. Carboxylic acid reductase is a versatile enzyme for the conversion of fatty acids into fuels and chemical commodities. *Proc. Natl. Acad. Sci. U.S.A.* 110, 87-92.

Amann, E., Ochs, B., Abel, K., 1988. Tightly regulated tac promoter vectors useful for the expression of unfused and fused proteins in *Escherichia coli*. *Gene*, 69, 301-315.

Arora, P., Vats, A., Saxena, P., Mohanty, D., Gokhale, R. S., 2005. Promiscuous fatty acyl CoA ligases produce acyl-CoA and acyl-SNAC precursors for polyketide biosynthesis. *J. Am. Chem. Soc.* 127, 9388-9.

Baba, T., Ara, T., Hasegawa, M., Takai, Y., Okumura, Y., Baba., M., Datsenko, K. A., Tomita, M., Wanner, B. L., Mori, H., 2006. Construction of *Escherichia coli* K-12 in-frame, single-gene knockout mutants: the Keio collection. *Mol. Syst. Biol.* 2, 2006.0008.

Ballesteros, M., Fredriksson, Å., Henriksson, J., Nyström, T., 2001. Bacterial senescence: protein oxidation in non-proliferating cells is dictated by the accuracy of the ribosomes. *The Eur. Mol. Biol. Organ. J.* 20, 5280-5289.

Becker, S., Vlad, D., Schuster, S., Pfeiffer, P., Unden, G., 1997. Regulatory 02 tensions for the synthesis of fermentation products in *Escherichia coli* and relation to aerobic respiration. *Arch. Microbiol.* 168, 290-296.

Cheng, J. B., Russell, D. W., 2004. Mammalian wax biosynthesis. I. Identification of two fatty acyl-Coenzyme A reductases with different substrate specificities and tissue distributions. *J. Biol. Chem.* 279, 37789-97.

Dellomonaco, C., Clomburg, J. M., Miller, E. N., Gonzalez, R., 2011. Engineered reversal of the β-oxidation cycle for the synthesis of fuels and chemicals. *Nature* 476, 355-9.

Dellomonaco, C., Fava, F., Gonzalez, R., 2010. The path to next generation biofuels: successes and challenges in the era of synthetic biology. *Microb. Cell Fact.* 9, 3.

Dirusso, C. C., Heimert, T. L., Metzger, A. K., 1992. Characterization of FadR, a Global Transcriptional Regulator of Fatty Acid Metabolism in *Escherichia coli*. *J. Biol. Chem.* 267, 8685-8691.

Doan, T. T. P., Carlsson, A. S., Hamberg, M., Bülow, L., Stymne, S., Olsson, P., 2009. Functional expression of five *Arabidopsis* fatty acyl-CoA reductase genes in *Escherichia coli*. *J. Plant Physiol.* 166, 787-796.

Dueber, J. E., Wu, G. C., Malmirchegini, G. R., Moon, T. S., Petzold, C. J., Ullal, A. V, Prather, K. L. J., Keasling, J. D., 2009. Synthetic protein scaffolds provide modular control over metabolic flux. *Nat. Biotechnol.* 27, 753-9.

Frank, S., Lawrence, A. D., Prentice, M. B., Warren, M. J., 2013. Bacterial microcompartments moving into a synthetic biological world. *J. Biotechnol.* 163, 273-9.

Gibson, D. G., Young, L., Chuang, R.-Y., Venter, J. C., Hutchison, C. A., Smith, H. O., 2009. Enzymatic assembly of DNA molecules up to several hundred kilobases. *Nat. Methods* 6, 343-345.

Hellenbrand, J., Biester, E.-M., Gruber, J., Hamberg, M., Frentzen, M., 2011. Fatty acyl-CoA reductases of birds. *BMC Biochem.* 12,64.

Hofvander, P., Doan, T. T. P., Hamberg, M., 2011. A prokaryotic acyl-CoA reductase performing reduction of fatty acyl-CoA to fatty alcohol. *FEBS Lett.* 585, 3538-43.

Kamedas, K., Nunn, W. D., 1981. Purification and Characterization of Acyl Coenzyme A Synthetase from *Escherichia coli*. *J. Biol. Chem.* 256, 5702-5707.

Keasling, J. D., 2012. Synthetic biology and the development of tools for metabolic engineering. *Metab. Eng.* 14, 189-95.

Kobayashi, A., Hirakawa, H., Hirata, T., Nishino, K., Yamaguchi, A., 2006. Growth phase-dependent expression of drug exporters in *Escherichia coli* and its contribution to drug tolerance. *J. Bacteriol.* 188, 5693-703.

Lennen, R. M., Braden, D. J., West, R. A., Dumesic, J. A., Pfleger, B. F., 2010. A process for microbial hydrocarbon synthesis: Overproduction of fatty acids in *Escherichia coli* and catalytic conversion to alkanes. *Biotechnol. Bioeng.* 106, 193-202.

Lennen, R. M., Pfleger, B. F., 2012. Engineering *Escherichia coli* to synthesize free fatty acids. *Trends Biotechnol.* 30, 659-67.

Lennen, R. M., Pfleger, B. F., 2013. Microbial production of fatty acid-derived fuels and chemicals. *Curr. Opin. Biotechnol.* 1-10.

Liénard, M. A., Hagström, A. K., Lassance, J.-M., Löfstedt, C., 2010. Evolution of multicomponent pheromone signals in small ermine moths involves a single fatty-acyl reductase gene. *Proc. Natl. Acad. Sci.* U.S.A. 107, 10955-60.

Matheson, K. L., 1996. Surfactants raw materials: classification, synthesis, and uses. In: Spitz, L. (Ed.), Soaps and Detergents: A Theoretical and Practical Review, AOCS, Champaign, Ill., pp. 288-303.

Mudge, S. M., Belanger, S. E., Nielsen, A. M., 2008. Fatty Alcohols: Anthropogenic and Natural Occurrence in the Environment. The Royal Society of Chemistry, Cambridge, UK.

Neidhardt, F. C., Bloch, P. L., Smith, D. F., 1974. Culture Medium for Enterobacteria. *J. Bacteriol.* 119, 736-747.

Ranganathan, S., Tee, T. W., Chowdhury, A., Zomorrodi, A. R., Yoon, J. M., Fu, Y., Shanks, J. V, Maranas, C. D., 2012. An integrated computational and experimental study for overproducing fatty acids in *Escherichia coli*. *Metab. Eng.* 14, 687-704.

Reiser, S., Somerville, C., 1997. Isolation of mutants of *Acinetobacter calcoaceticus* deficient in wax ester synthesis and complementation of one mutation with a gene encoding a fatty acyl coenzyme A reductase. *J. Bacteriol.* 179, 2969-2975.

Rowland, O., Domergue, F., 2012. Plant fatty acyl reductases: enzymes generating fatty alcohols for protective layers with potential for industrial applications. *Plant Science* 193-194, 28-38.

Rupilius, W., Ahmad, S., 2006. The Changing World of Oleochemicals. *Palm Oil Developments* 44, 15-28.

Sampson, E. M., Bobik, T. A., 2008. Microcompartments for B12-dependent 1,2-propanediol degradation provide protection from DNA and cellular damage by a reactive metabolic intermediate. *J. Bacteriol.* 190, 2966-71.

Steen, E. J., Kang, Y., Bokinsky, G., Hu, Z., Schirmer, A., McClure, A., Del Cardayre, S. B., Keasling, J. D., 2010. Microbial production of fatty-acid-derived fuels and chemicals from plant biomass. *Nature* 463, 559-562.

Teerawanichpan, P., Qiu, X., 2010. Fatty acyl-CoA reductase and wax synthase from *Euglena gracilis* in the biosynthesis of medium-chain wax esters. *Lipids* 45, 263-273.

Tseng, C., Albrecht, J., Gunsalus, R. P., 1996. Effect of Microaerophilic Cell Growth Conditions on Expression of the Aerobic (cyoABCDE and cydAB) and Anaerobic Pathway Genes in *Escherichia coli*. *Microbiology* 178, 1094-1098.

Voelker, T. A., Davies, H. M., 1994. Alteration of the specificity and regulation of Alteration of the Specificity and Regulation of Fatty Acid Synthesis of *Escherichia coli* by Expression of a Plant Medium—Chain Acyl-Acyl Carrier Protein Thioesterase. *J. Bacteriol.* 176(23), 7320-7327.

Wang, Q., Tappel, R. C., Zhu, C., Nomura, C. T., 2012. Development of a new strategy for production of medium-chain-length polyhydroxyalkanoates by recombinant *Escherichia coli* via inexpensive non-fatty acid feedstocks. *Appl. Environ. Microbiol.* 78, 519-27.

Willis, R. M., Wahlen, B. D., Seefeldt, L. C., Barney, B. M., 2011. Characterization of a fatty acyl-CoA reductase from *Marinobacter aquaeolei* VT8: a bacterial enzyme catalyzing the reduction of fatty acyl-CoA to fatty alcohol. *Biochemistry* 50, 10550-8.

Xu, P., Gu, Q., Wang, W., Wong, L., Bower, A. G. W., Collins, C. H., Koffas, M. A. G., 2013. Modular optimization of multi-gene pathways for fatty acids production in *E. coli*. *Nat. Commun.* 4, 1409.

Youngquist, J. T., Lennen, R. M., Ranatunga, D. R., Bothfeld, W. H., Marner, W. D., Pfleger, B. F., 2012. Kinetic modeling of free fatty acid production in *Escherichia coli* based on continuous cultivation of a plasmid free strain. *Biotechnol. Bioeng.* 109, 1518-27.

Youngquist, J. T., Rose, J. P., Pfleger, B. F., 2013. Free fatty acid production in *Escherichia coli* under phosphate-limited conditions. *Appl. Microbiol. Biotechnol.* 97(11): 5149-59.

Youngquist J T, Schumacher M H, Rose J P, Raines T C, Politz M C, Copeland M F, Pfleger B F. Production of medium chain length fatty alcohols from glucose in *Escherichia coli*. *Metab Eng.* 2013, 20:177-86.

Yu, D., Ellis, H. M., Lee, E.-C., Jenkins, N. A., Copeland, N. G., Court, D. L., 2000. An efficient recombination system for chromosome engineering in *Escherichia coli*. *Proc. Natl. Acad. Sci.* U.S.A. 97, 5978-5983.

Yuan, L., Dehesh, K., Kridl, J., Knauf, V., 1999. Engineering plant thioesterases for altered substrate specificity. U.S. Pat. No. 5,955,329.

Zha, W., Rubin-Pitel, S. B., Shao, Z., Zhao, H., 2009. Improving cellular malonyl-CoA level in *Escherichia coli* via metabolic engineering. *Metab. Eng.* 11, 192-198.

Zhang, F., Ouellet, M., Batth, T. S., Adams, P. D., Petzold, C. J., Mukhopadhyay, A., Keasling, J. D., 2012. Enhancing fatty acid production by the expression of the regulatory transcription factor FadR. *Metab. Eng.* 14, 653-60.

Zheng, Y.-N., Li, L., Liu, Q., Yang, J., Wang, X., Liu, W., Xu, X., Liu, H., Zhao, G., Xian, M., 2012. Optimization of fatty alcohol biosynthesis pathway for selectively enhanced production of C12/14 and C16/18 fatty alcohols in engineered *Escherichia coli*. *Microb. Cell Fact.* 11, 65.

What is claimed is:

1. A recombinant cell for producing a fatty alcohol comprising a recombinant thioesterase gene, a recombinant acyl-CoA synthetase gene, and a recombinant acyl-CoA reductase gene, wherein the acyl-CoA reductase gene is configured to be present in the cell in exponential phase at a copy number of from 1 to 5 copies per copy of genomic DNA, wherein a gene in the cell selected from the group consisting of an acyl-CoA dehydrogenase gene, an enoyl-CoA hydratase gene, a 3-hydroxyacyl-CoA dehydrogenase gene, and a 3-ketoacyl-CoA thiolase gene is deleted, and wherein the recombinant cell is capable of producing a fatty alcohol.

2. The recombinant cell of claim 1, wherein the acyl-CoA synthetase gene encodes a protein comprising the amino acid sequence of SEQ ID NO: 12 or an amino acid sequence at least 90% identical to SEQ ID NO: 12.

3. The recombinant cell of claim 1, wherein the acyl-CoA synthetase gene is expressed in the recombinant cell at a level greater than 2-fold and less than 75-fold the endogenous expression level of a native acyl-CoA synthetase gene in the corresponding non-recombinant cell.

4. The recombinant cell of claim 1, wherein the recombinant acyl-CoA reductase gene encodes an enzyme having both acyl-CoA reductase activity and aldehyde reductase activity.

5. The recombinant cell of claim 1, further comprising a recombinant aldehyde reductase gene.

6. The recombinant cell of claim 1, wherein the acyl-CoA reductase gene encodes a protein comprising the amino acid sequence of SEQ ID NO: 16 or an amino acid sequence at least 90% identical to SEQ ID NO: 16.

7. The recombinant cell of claim 1, wherein the acyl-CoA reductase gene and the acyl-CoA synthetase gene are included in the cell at a copy ratio of from about 5:1 (acyl-CoA reductase gene:acyl-CoA synthetase gene) to about 1:1 (acyl-CoA reductase gene:acyl-CoA synthetase gene).

8. The recombinant cell of claim 1, wherein the relative level of expression of the recombinant acyl-CoA reductase gene as determined by quantitative PCR (qPCR) with respect to the level of expression of the recombinant acyl-CoA synthetase gene as determined by qPCR is the same as that obtained when the recombinant acyl-CoA reductase gene and the recombinant acyl-CoA synthetase gene are present in a copy ratio of about 5:1 (recombinant acyl-CoA reductase gene:recombinant acyl-CoA synthetase gene) to about 1:1 (recombinant acyl-CoA reductase gene:recombinant acyl-CoA synthetase gene) and the recombinant acyl-CoA reductase gene and the recombinant acyl-CoA synthetase gene each comprises the same promoter.

9. The recombinant cell of claim 1, wherein the acyl-CoA dehydrogenase gene is deleted.

10. The recombinant cell of claim 1, wherein the recombinant cell is *E. coli* and the gene fadE is deleted.

11. The recombinant cell of claim 1, wherein a gene selected from the group consisting of the enoyl-CoA hydratase gene, the 3-hydroxyacyl-CoA dehydrogenase gene, and the 3-ketoacyl-CoA thiolase gene is deleted.

12. The recombinant cell of claim 1, wherein the recombinant cell is *E. coli* and the genes fadA and fadI; fadB and fadJ; or fadA, fadI, fadB and fadJ are deleted.

13. The recombinant cell of claim 1, wherein the thioesterase gene encodes a protein comprising the amino acid sequence of SEQ ID NO: 18 or an amino acid sequence at least 90% identical to SEQ ID NO: 18.

14. The recombinant cell of claim 1, wherein the recombinant cell is a microbial cell.

15. The recombinant cell of claim 1, wherein the recombinant cell is a bacterial cell.

16. A method of producing a fatty alcohol comprising culturing the recombinant cell as recited in claim 1 under conditions effective to produce the fatty alcohol.

17. The method of claim 16, comprising culturing the recombinant cell in a medium comprising a carbohydrate and no more than about 1 g $L^{-1}$ dissolved, exogenous free fatty acid or salt thereof.

* * * * *

UNITED STATES PATENT AND TRADEMARK OFFICE
CERTIFICATE OF CORRECTION

| | | |
|---|---|---|
| PATENT NO. | : 9,708,630 B1 | Page 1 of 1 |
| APPLICATION NO. | : 14/509408 | |
| DATED | : July 18, 2017 | |
| INVENTOR(S) | : Brian F. Pfleger and J. Tyler Youngquist | |

It is certified that error appears in the above-identified patent and that said Letters Patent is hereby corrected as shown below:

In the Claims

In Claim 13, Column 94, Line 34, "90%" should read --80%--.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*